US008221778B2

(12) United States Patent
Siegel et al.

(10) Patent No.: US 8,221,778 B2

(45) **Date of Patent: *Jul. 17, 2012**

(54) DRUG-CONTAINING IMPLANTS AND METHODS OF USE THEREOF

(75) Inventors: Steven Siegel, Berwyn, PA (US); Karen Winey, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1034 days.

This patent is subject to a terminal disclaimer.

(21) Appl. No.: 11/183,232

(22) Filed: Jul. 18, 2005

(65) Prior Publication Data

US 2006/0153895 A1 Jul. 13, 2006

Related U.S. Application Data

(63) Continuation-in-part of application No. PCT/US2005/000884, filed on Jan. 12, 2005.

(51) Int. Cl.

*A61F 13/00* (2006.01)
*A61F 2/10* (2006.01)
*A61B 19/00* (2006.01)

(52) U.S. Cl. ......... 424/423; 424/422; 424/426; 424/428

(58) Field of Classification Search ........................ None
See application file for complete search history.

(56) References Cited

U.S. PATENT DOCUMENTS

| | | | | |
|---|---|---|---|---|
| 4,351,337 | A | 9/1982 | Sidman | |
| 4,874,612 | A | 10/1989 | Deasy | |
| 4,883,666 | A | 11/1989 | Sabel et al. | |
| 5,601,835 | A | 2/1997 | Sabel et al. | |
| 5,629,008 | A | 5/1997 | Lee | |
| 5,654,008 | A | 8/1997 | Herbert et al. | |
| 5,665,428 | A | 9/1997 | Cha et al. | |
| 5,770,231 | A | 6/1998 | Mesens | |
| 5,792,477 | A | 8/1998 | Rickey et al. | |
| 5,817,343 | A | 10/1998 | Burke | |
| 5,871,778 | A * | 2/1999 | Kino et al. | 424/489 |
| 5,965,168 | A | 10/1999 | Mesens | |
| 5,989,463 | A | 11/1999 | Tracy et al. | |
| 6,004,573 | A | 12/1999 | Rathi et al. | |
| 6,077,843 | A | 6/2000 | Francois et al. | |
| 6,086,908 | A | 7/2000 | Gopferich | |
| 6,110,921 | A | 8/2000 | Mesens | |
| 6,117,949 | A | 9/2000 | Rathi et al. | |
| 6,130,200 | A | 10/2000 | Brodbeck et al. | |
| 6,143,314 | A | 11/2000 | Chandrashekar | |
| 6,166,173 | A | 12/2000 | Mao et al. | |
| 6,201,072 | B1 | 3/2001 | Rathi et al. | |
| 6,319,512 | B1 | 11/2001 | Rothen-Weinhold et al. | |
| 6,322,797 | B1 | 11/2001 | Mao et al. | |
| 6,368,362 | B1 | 4/2002 | Pedemonte et al. | |
| 6,368,632 | B1 * | 4/2002 | Mesens et al. | 424/489 |
| 6,544,559 | B2 | 4/2003 | Mesens | |
| 6,750,341 | B2 * | 6/2004 | Krochmal et al. | 544/282 |
| 6,803,055 | B2 | 10/2004 | Mesens | |
| 2001/0005719 | A1 | 6/2001 | Borstel | |
| 2002/0179096 | A1 * | 12/2002 | Siegel et al. | 128/898 |
| 2006/0029637 | A1 * | 2/2006 | Tice et al. | 424/423 |
| 2006/0159721 | A1 * | 7/2006 | Siegel et al. | 424/426 |
| 2008/0305140 | A1 * | 12/2008 | Siegel et al. | 424/423 |
| 2009/0297572 | A1 * | 12/2009 | Siegel et al. | 424/422 |

FOREIGN PATENT DOCUMENTS

| | | |
|---|---|---|
| EP | 669128 | 1/2000 |
| WO | WO 94/10982 | 5/1994 |
| WO | WO 95/13814 | 5/1995 |
| WO | WO 01/89482 | 11/2001 |
| WO | WO 02/00137 | 1/2002 |
| WO | WO 03/000156 | 1/2003 |
| WO | WO 03/020245 | 3/2003 |
| WO | WO 2005/070332 | 8/2005 |

OTHER PUBLICATIONS

Adams et al. (2001) Systematic meta-review of depot antipsychotic drugs for people with schizophrenia. Br J Psychiatry 179:290-299.
Anderson, et al. (1997) Biodegradation and biocompatibility of PLA and PLGA microspheres. Adv Drug Delivery Rev 28:5-24.
Ayuso-Gutierrez, et al. (1997) Factors influencing relapse in the long-term course of schizophrenia. Schizophr Res 28:199-206.
Benelli, et al. (1998) Clonazepam microencapsulation in poly-D, L-lactide-co-glycolide microspeheres. J. Micorenscapsulation 15(4):431-443.
Boccuzzi et al. (2001) Utilization of oral hypoglycemic agents in a drug-insured U.S. population. Diabetes Care. Aug;24(8):1411-5.
Buckland, et al. (1993) Both splicing variants of the dopamine D2 receptor mRNA are up-regulated by antipsychotic drugs. Neurosci Lett 150:25-28.
Chen, et al. (2005) Microarray analysis of differentially expressed genes in rat frontal cortex under chronic risperidone treatment. Neuropsychopharmacology 30:268-277.

(Continued)

*Primary Examiner* — Robert A Wax
*Assistant Examiner* — Olga V Tcherkasskaya
(74) *Attorney, Agent, or Firm* — Mark S. Cohen; Pearl Cohen Zedek Latzer, LLP

(57) ABSTRACT

The present invention provides implants comprising a therapeutic drug and a polymer containing polylactic acid (PLA) and optionally polyglycolic acid (PGA). The present invention also provides methods of maintaining a therapeutic level of a drug in a subject, releasing a therapeutic drug at a substantially linear rate, and treating schizophrenia and other diseases and disorders, utilizing implants of the present invention.

10 Claims, 19 Drawing Sheets

OTHER PUBLICATIONS

Cheng, et al. (1998) A poly (D,L-lactide-co-glycolide) microsphere depot system for delivery of haloperidol. J. Controlled Release 55(2-3):203-212.
Cheng, et al. (2000) Schizophrenia and Drug Delivery Systems. J Drug Targeting 8(2):107-117.
Chui et al. (2003) Association between adherence to diuretic therapy and health care utilization in patients with heart failure. Pharmacotherapy. Mar;23(3):326-32.
Corriss, et al. (1999) Interactive risk factors for treatment adherence in a chronic psychotic disorders population. Psychiatry Res 89:269-274.
Csernansky (2003) Treatment of schizophrenia: preventing the progression of disease. Psychiatr Clin North Am 26:367-379.
Dash, et al. (1998) Therapeutic applications of implantable drug delivery systems. J Pharmacol Toxicol Methods 40:1-12.
Davis, et al. (2003) A meta-analysis of the efficacy of second-generation antipsychotics. Arch Gen Psychiatry 60:553-564.
Dorph-Petersen, et al. (2004) Stereological analysis of the mediodorsal thalamic nucleus in schizophrenia: volume, neuron number, and cell types. J Comp Neurol 472:449-462.
Elmer, et al. (1996) Cocaine cross-sensitization to dopamine uptake inhibitors: unique effects of GBR12909. Pharmacol Biochem Behav 53:911-918.
Fischel-Ghodsian, et al. (1993) Analysis of drug release kinetics from degradable polymeric devices. J Drug Target. 1(1):51-57.
Foss, et al. (2004) Development of acrylic-based copolymers for oral insulin delivery. Eur J Pharm Biopharm 57:163-169.
Foster and Goa (1998) Risperidone. A pharmacoeconomic review of its use in schizophrenia.Pharmacoeconomics. Jul;14(1):97-133.
Frank, et al. (2005) Controlled release from bioerodible polymers: effect of drug type and polymer composition. J Controlled Release 102:333-344.
Freiberg and Zhu (2004) Polymer microspheres for controlled drug release. Int J Pharm. Sep. 10;282(1-2):1-18.
Gander, et al. (2001) Polymers as a platform for drug delivery: Reviewing our current portfolio on poly(lactide-co-glycolide) (PLGA) microspheres. CHIMIA 55:212-217.
Geddes, et al. (2000) Atypical antipsychotics in the treatment of schizophrenia: systematic overview and meta-regression analysis. BMJ 321:1371-1376.
Goss, et al. (1991) Haloperidol treatment increases D2 dopamine receptor protein independently of RNA levels in mice. Life Sci 48:1015-1022.
Grayson, et al. (2005) Size and temperature effects on poly(lactic-co-glycolic acid) degradation and microreservoir device performance, Biomaterials 26:2137-2145.
Harrison and Goa (2004) Long-acting risperidone: a review of its use in schizophrenia. CNS Drugs.; 18(2):113-32.
Heller, (1979) Controlled drug release by polymer dissolution. II: Enzyme-mediated delivery device. J Pharm Sci. 68(7):919-21.
Higuchi (1961) Rate of release of medicaments from ointment bases containing drugs in suspensions. J. Pharm. Sci. 50:874-875.
Holy, et al. (2001) Optimizing the sterilization of PLGA scaffolds for use in tissue engineering. Biomaterials 22:25-31.
Hussain (2001) Fluorometric method for the simultaneous quantitation of differently-sized nanoparticles in rodent tissue. Int J Pharm 214:55-61.
Irani, et al. (2004) Patient attitudes towards surgically implantable, long-term delivery of psychiatric medicine. Neuropsychopharmacology 29:960-968.
Jain, et al. (2000) Controlled delivery of drugs from a novel injectable in situ formed biodegradable PLGA microsphere system. J Microencapsulation 17(3):343-62.
Jeong, et al. (2003) Preparation of poly(DL-lactide-co-glycolide) microspheres encapsulating all-trans retinoic acid. Int J Pharm 259:79-91.
Kane (1999) Olanzapine in the long-term treatment of schizophrenia. Br J Psychiatry Suppl: (37) 26-29.
Kane, et al. (1998) Guidelines for depot antipsychotic treatment in schizophrenia. European Neuropsychopharmacology Consensus Conference in Siena, Italy. Eur Neuropsychopharmacol 8:55-66.
Kane, et al. (2002) Efficacy and safety of aripiprazole and haloperidol versus placebo in patients with schizophrenia and schizoaffective disorder. J Clin Psychiatry 63:763-771.
Karow, et al. (2002) Subjective well-being and quality of life under atypical antipsychotic treatment. Psychopharmacology (Berl) 162:3-10.
Keefe, et al. (2004) Comparative effect of atypical and conventional antipsychotic drugs on neurocognition in first-episode psychosis: a randomized, double-blind trial of olanzapine versus low doses of haloperidol. Am J Psychiatry 161:985-995.
Keith, et al. (2003) Partial compliance and patient consequences in schizophrenia: our patients can do better. J Clin Psychiatry 64:1308-1315.
Kitchell, et al. (1985) Poly (lactic/glycolic acid) biodegradable drug-polymer matrix systems. Methods Enzymol. 112:436-48.
Klavon, et al. (1990) Insertion site complications during the first year of NORPLANT use. Contraception 41:27-37.
Knable, et al. (1997) Extrapyramidal side effects with risperidone and haloperidol at comparable D2 receptor occupancy levels. Psychiatry Res 75:91-101.
Knegtering, et al. (2005) Predominant role of the 9-hydroxy metabolite of risperidone in elevating blood prolactin levels. Am J Psychiatry 162:1010-1012.
Kohler, et al. (1994) A new animal model of dopamine supersensitivity using s.c. implantation of haloperidol releasing polymers. Neuroscience Letters 170(1):99-102.
Kulkarni, et al. (1971) Biodegradable poly(lactic acid) polymers. 5(3):169-81.
Kusumi, et al. (2000) Differential effects of subchronic treatments with atypical antipsychotic drugs on dopamine D2 and serotonin 5-HT2A receptors in the rat brain. J Neural Transm 107:295-302.
Lambert, et al. (2003) Pharmacological approaches to the management of schizophrenia. Med J Aust 178 Suppl: S57-61.
Larobina, et al. (2002) Mechanistic understanding of degradation in bioerodible polymers for drug delivery. AICHE J 48:2960-2970.
Lelas, et al. (2004) Anxiolytic-like effects of the corticotropin-releasing factorl (CRF1) antagonist DMP904 [4-(3-pentylamino)-2,7-dimethyl-8-(2-methy1-4-methoxyphenyl)-pyrazolo-[1,5-a]-pyrimidine] administered acutely or chronically at doses occupying central CRF1 receptors in rats. J Pharmacol Exp Ther 309:293-302.
Lewis, et al. (2001a) Lamina-specific deficits in parvalbumin-immunoreactive varicosities in the prefrontal cortex of subjects with schizophrenia: evidence for fewer projections from the thalamus. Am J Psychiatry 158:1411-1422.
Lewis, et al. (2001b) Service use and costs of treating schizophrenia with atypical antipsychotics. J Clin Psychiatry 62:749-756.
Leysen, et al. (1994) Risperidone: a novel antipsychotic with balanced serotonin-dopamine antagonism, receptor occupancy profile, and pharmacologic activity. J Clin Psychiatry 55 Suppl:5-12.
Li, et al. (1996) Hydrolytic degradation of poly (D,L-lactic acid) in the presence of caffeine base. J. Control. Release 40:41-53.
Lilly, et al. (1998) A physiologically based pharmacokinetic description of the oral uptake, tissue dosimetry, and rates of metabolism of bromodichloromethane in the male rat. Toxicol Appl Pharmacol 150:205-217.
Linhardt (1989) "Biodegradable Polymers for Controlled Release of Drugs" Controlled Release of Drugs, Rosoff, Ed., New York: VCH Publishers, Chapter 2, p. 53-83.
Lu et al. (2000) In vitro and in vivo degradation of porous poly(DL-lactic-co-glycolic acid) foams. Biomaterials. Sep; 21(18):1837-45.
Martin, et al. (2003) Clinical experience with the long-acting injectable formulation of the atypical antipsychotic, risperidone. Curr Med Res Opin 19:298-305.
McCombs, et al. (1999) Use patterns for antipsychotic medications in medicaid patients with schizophrenia. J Clin Psychiatry 60 Suppl 19:5-11; discussion 12-13.
McQuade, et al. (2004) A comparison of weight change during treatment with olanzapine or aripiprazole: results from a randomized, double-blind study. J Clin Psychiatry 65 Suppl 18:47-56.
Meltzer (1995) The role of serotonin in schizophrenia and the place of serotonin-dopamine antagonist antipsychotics. J Clin Psychopharmacol 15:2S-3S.

Menzin, et al. (2003) Treatment adherence associated with conventional and atypical antipsychotics in a large state medicaid program. Psychiatr Serv 54:719-723.
Metzger, et al. (2007) "Pharmacokinetic and behavioral characterization of a long-term antipsychotic delivery system in rodents and rabbits" Psychopharmacology Psychopharmacology (Berl). Feb; 190(2):201-11.
Miller-Chou, et al. (2003) A reviews of polymer dissolution. Progress Pol Sci 28:1223-1270.
Narasimhan, et al. (1997) Molecular analysis of drug delivery systems controlled by dissolution of the polymer carrier. J Pharma Sci 86:297-304.
Nasrallah, et al. (2002) Efficacy, safety, and tolerability of quetiapine in patients with schizophrenia. J Clin Psychiatry 63 Suppl 13:12-20.
Nasrallah, et al. (2004) Atypical antipsychotics and metabolic dysregulation: evaluating the risk/benefit equation and improving the standard of care. J Clin Psychopharmacol 24:S7-14.
Natsugoe, et al. (1960) Controlled Release of Cisplatin Incorporated into Biodegradable Poly-D, L-Lactic Acid. Anticancer Research 17(3C):1957-60.
Nyberg, et al. (1996) Positron emission tomography of in-vivo binding characteristics of atypical antipsychotic drugs. Review of D2 and 5-HT2 receptor occupancy studies and clinical response. Br J Psychiatry Suppl:40-44.
Okada, et al. (1995) Biodegradable microspheres in drug delivery. Crit Rev Ther Drug Carrier Syst 12:1-99.
Panyam, et al. (2003) Biodegradable nanoparticles for drug and gene delivery to cells and tissue. Adv Drug Delivery Rev 55:329-347.
Ramaswamy, et al. (2004) Aripiprazole possibly worsens psychosis. Int Clin Psychopharmacol 19:45-48.
Reeves, et al. (2004) Worsening schizoaffective disorder with aripiprazole. Am J Psychiatry 161:1308.
Reuss, et al. (2001) Atypical neuroleptic drugs downregulate dopamine sensitivity in rat cortical and striatal astrocytes. Mol Cell Neurosci 18:197-209.
Robinson, et al. (2002) Predictors of medication discontinuation by patients with first-episode schizophrenia and schizoaffective disorder. Schizophr Res 57:209-219.
Ron, et al. (1991) "Erodible Systems" *Treatise on Cont. Drug Del.* 199-217.
Roskos, et al. (1997) "Degradable controlled release systems useful for protein delivery" in Protein Delivery: Physical Systems, Sanders and Hendren eds., Plenum press, New York, Chapter 2, 45-92.
Sabel, et al. (1990) Levodopa delivery from controlled-release polymer matrix: delivery of more than 600 days in vitro and 225 days of elevated plasma levels after subcutaneous implantation in rats. J Pharmacol Exp Ther 255:914-922.
Sarma, et al. (1995) Neurovascular injury during removal of levonorgestrel implants. Am J Obstet Gynecol 172:120-121.
Schotte, et al. (1996) Risperidone compared with new and reference antipsychotic drugs: in vitro and in vivo receptor binding. Psychopharmacology (Berl) 124:57-73.
Seeman (2001) Clinical trials in psychiatry: do results apply to practice? Can J Psychiatry 46:352-355.
Sharma, et al. (2003) Cognitive function in schizophrenia. Deficits, functional consequences, and future treatment. Psychiatr Clin North Am 26:25-40.
Siegel (2007) Extended release drug delivery strategies in psychiatry: Theory to practice. Psychiatry.
Siegel, et al. (2002) Surgically implantable long-term antipsychotic delivery systems for the treatment of schizophrenia. Neuropsychopharmacology 26:817-823.
Siegel, et al. (2006) Effect of drug type on the degradation rate of PLGA Matrices. Eur J Pharm Biopharm. 64(3):287-93.
Siepmann, et al. (2001) Mathematical modeling of bioerodible, polymeric drug delivery systems. Adv Drug Delivery Rev 48:229-247.
Simpson, et al. (2004) Randomized, controlled, double-blind multicenter comparison of the efficacy and tolerability of ziprasidone and olanzapine in acutely ill inpatients with schizophrenia or schizoaffective disorder. Am J Psychiatry 161:1837-1847.
Strakowski, et al. (2003) Atypical antipsychotics in the treatment of bipolar disorder. Expert Opin Pharmacother 4:751-760.
Sung, et al. (1998) Controlled release of nalbuphine prodrugs from biodegradable polymeric matrices: influence of prodrug hydrphillicity and polymer composition. Int. J. Pharm. 172:17-25.
Svarstad, et al. (2001) Using drug claims data to assess the relationship of medication adherence with hospitalization and costs. Psychiatr Sery 52:805-811.
Swainston Harrison, et al. (2004) Aripiprazole: a review of its use in schizophrenia and schizoaffective disorder. Drugs 64:1715-1736.
Swerdlow, et al. (1994) Assessing the validity of an animal model of deficient sensorimotor gating in schizophrenic patients. Arch Gen Psychiatry 51:139-154.
Tarazi, et al. (2002) Long-term effects of olanzapine, risperidone, and quetiapine on serotonin 1A, 2A and 2C receptors in rat forebrain regions. Psychopharmacology (Berl) 161:263-270.
TEICH (2003) Side effects of ziprasidone. Am J Psychiatry 160:1355-1356.
Velligan, et al. (2003) Psychopharmacology: perspectives on medication adherence and atypical antipsychotic medications. Psychiatr Serv 54:665-667.
Visco, et al. (1999) Observed patient compliance with a structured outpatient bladder retraining program. Am J Obstet Gynecol 181:1392-1394.
Wada, et al. (1991) In vitro evaluation of sustained drug release from biodegradable elastomer. Pharm Res. 8(10):1292-1296.
Wang, et al. (2000) Synthesis, characterization, biodegradation, and drug delivery application of biodegradable lactic/glycolic acid polymers: I. Synthesis and characterization. J Biomater Sci Polym Ed. 11(3):301-18.
Yasui-Furukori, et al. (2001) Different enantioselective 9-hydroxylation of risperidone by the two human CYP2D6 and CYP3A4 enzymes. Drug Metab Dispos 29:1263-1268.
Zheng, et al. (1998) High-performance liquid chromatography-mass spectrometry-mass spectrometry analysis of morphine and morphine metabolites and its application to a pharmacokinetic study in male Sprague-Dawley rats. J Pharm Biomed Anal 16:971-980.
Barichello et al. "Encapsulation of Hydrophilic and Lipophilic Drugs in PLGA Nanoparticles by the Nanoprecipitation Method", vol. 25, No. 4 , pp. 471-476, (1999).
Budhian et al. "Production of haloperidol loaded PLGA nanoparticles for extended controlled drug release of haloperidol" Journal of Microencapsulation, vol. 22, Issue 7, pp. 773-785, , Nov. 2005.
Budhian et al. "Haloperidol-loaded PLGA nanoparticles: Systematic study of particle size and drug content" International Journal of Pharmaceutics 336 ,367-375, (2007).
Choi et al. "Development of Drug-Loaded PLGA Microparticles with Different Release Patterns for Prolonged Drug Delivery" Bull. Korean Chem. Soc. vol. 32, No. 3, 867, (2011).
Chorny et al. "Study of the drug release mechanism from tyrphostin AG-1295-loaded nanospheres by in situ and external sink methods" Journal of Controlled ReleaseVolume 83, Issue 3, pp. 401-414, Oct. 30, 2002.
Kiortsis et al. "Drug release from tableted wet granulations comprising cellulosic (HPMC or HPC) and hydrophobic component" Eur J Pharm Biopharm.; 59(1):73-83, Jan. 2005.
Chinese Office Action Application No. 200580039021.3 Dated Oct. 9, 2010.
Japenese Office Action Application No. 2006-549540 Dated Feb. 15, 2011.
European Search Report Application No. PCT/US2006027894 Dated Oct. 10, 2011.

* cited by examiner

DRUG-CONTAINING IMPLANTS AND METHODS OF USE THEREOF

CROSS REFERENCE TO RELATED APPLICATIONS

This application is a continuation-in-part of PCT International Application No. PCT/US05/00884, International Filing Date Jan. 12, 2005, which is hereby incorporated in their entirety by reference herein.

FIELD OF INVENTION

The present invention provides implants comprising a therapeutic drug and a polymer containing polylactic acid (PLA) and optionally polyglycolic acid (PGA). The present invention also provides methods of maintaining a therapeutic level of a drug in a subject, releasing a therapeutic drug at a substantially linear rate, and treating schizophrenia and other diseases and disorders, utilizing implants of the present invention.

BACKGROUND OF THE INVENTION

Medication noncompliance is the highest determinant of relapse in schizophrenia. Therefore, a therapy method that helps patients remain on medication for extended periods would substantially improve clinical outcomes. Current methods of administering anti-schizophrenia medication (e.g. risperidone) provide dosing for one month or less. Thus, methods of providing therapeutic levels of risperidone and other medications axe needed in the art.

SUMMARY OF THE INVENTION

The present invention provides implants comprising a therapeutic drug and a polymer containing polylactic acid (PLA) and optionally polyglycolic acid (PGA). The present invention also provides methods of maintaining a therapeutic level of a drug in a subject, releasing a therapeutic drug at a substantially linear rate, and treating schizophrenia and other diseases and disorders, utilizing implants of the present invention.

In one embodiment, the present invention provides a biodegradable implant having (a) a therapeutic drug present in an amount of 10%-60% by mass, relative to the mass of the implant; and (b) a polymer present in an amount of 40%-70% by mass, relative to the mass of the implant, the polymer comprising PLA and optionally PGA in a PLA:PGA molar ratio between 50:50 and 100:0

In another embodiment, the present invention provides a method for maintaining a therapeutic level of a drug in a subject for a period of at least about 4 months, comprising administering to the subject a set of biodegradable implants, the set of biodegradable implants consisting of one or more individual biodegradable implants having (a) a therapeutic drug present in an amount of 10%-60% by mass, relative to the mass of the implant; and (b) a polymer present in an amount of 40%-70% by mass, relative to the mass of the implant, the polymer comprising PLA and optionally PGA in a PLA:PGA molar ratio between 50:50 and 100:0 and wherein the individual biodegradable implants, if more than one in number, do not differ substantially from one another in their PLA:PGA molar ratio, thereby maintaining a therapeutic level of a drug in a subject for a period of at least about 4 months.

In another embodiment, the present invention provides a method for maintaining a therapeutic level of a drug in a subject for a period of at least about one year, comprising (1) administering to the subject an initial set of biodegradable implants, wherein the initial set of biodegradable implants consists of one or more individual biodegradable implants having (a) a therapeutic drug present in an amount of 10%-60% by mass, relative to the mass of the implant; and (b) a polymer present in an amount of 40%-70% by mass, relative to the mass of the implant, the polymer comprising PLA and optionally PGA in a PLA:PGA molar ratio between 50:50 and 100:0; and (2) administering to the subject a maintenance set of one or mole biodegradable implants to the subject near the point of peak release of the initial set of biodegradable implants, wherein the maintenance set of biodegradable implants consists of additional individual biodegradable implants equivalent in the PLA:PGA molar ratio to the individual biodegradable implants in the initial set of biodegradable implants. The individual biodegradable implants of the initial set, if more than one in number, do not differ substantially from one another in their PLA:PGA molar ratio, thereby maintaining a therapeutic level of a drug in a subject for a period of at least about one yeas.

DETAILED DESCRIPTION OF THE INVENTION

Figure 1:
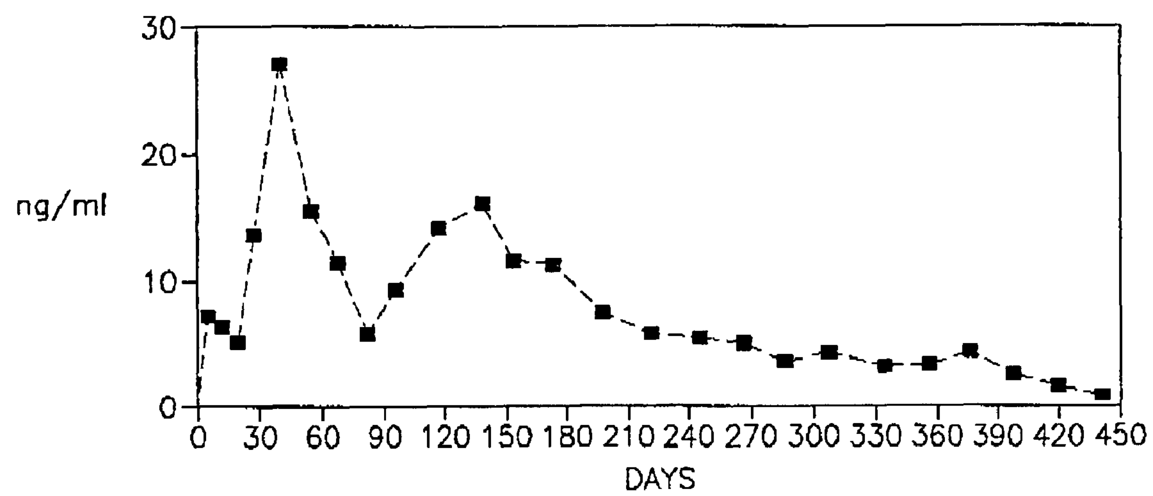
FIG. 1: Longitudinal detection of haloperidol levels for 443 days in primates as a result of implants.

The present invention provides implants comprising a therapeutic drug and a polymer containing polylactic acid (PLA) and optionally polyglycolic acid (PGA). The present invention also provides methods of maintaining a therapeutic level of a drug in a subject, releasing a therapeutic drug at a substantially linear rate, and treating schizophrenia and other diseases and disorders, utilizing implants of the present invention In one embodiment, the present invention provides a biodegradable implant having (a) a therapeutic drug present in an amount of 10%-60% by mass, relative to the mass of the implant; and (b) a polymer present in an amount of 40%-70% by mass, relative to the mass of the implant, the polymer comprising PLA and optionally PGA in a PLA:PGA molar ratio between 50:50 and 100:0

The term "biodegradable," as used herein, refers, in one embodiment, to a material that is degraded in a biological environment In another embodiment, "biodegradable" refers to a material that has a finite half-life in a biological environment. In another embodiment, "biodegradable" refers to a material that has a measurable half-life in a biological environment. In another embodiment, "biodegradable" refers to a material that is degraded inside a living organism In another embodiment, "biodegradable" refers to a material that has a finite half-life inside a living organism. In another embodiment, "biodegradable" refers to a material that has a measurable half-life inside a living organism. In another embodiment, the term "biodegradable" is equivalent to the term "bioerodible."

In one embodiment, the half-life is 1 month or less. In another embodiment, the half-life is 2 months or less. In another embodiment, the half-life is 3 months or less. In another embodiment, the half-life is 4 months or less. In another embodiment, the half-life is 5 months or less. In another embodiment, the half-life is 6 months or less In another embodiment, the half-life is 8 months or less. In another embodiment, the half-life is 10 months or less. In another embodiment, the half-life is one year or less In another embodiment, the half-life is 1.5 years or less. In another embodiment, the half-life is 2 years or less. In another embodiment, the half-life is 3 years or less. In another embodiment, the half-life is 4 years or less. In another embodiment, the half-life is 5 years or less. In another embodiment, the half-life is 7 years or less. In another embodiment, the half-life is 10 years or less. Each possibility represents a separate embodiment of the present invention.

"Polymer" refers, in one embodiment, to a macromolecule composed of individual units, or monomers. In another embodiment, the polymer is a branched polymer. In another embodiment, the polymer is a linear polymer. In another embodiment, the polymer is a cross-linked polymer. In another embodiment, the polymer is any other type of polymer known in the art. Each possibility represents a separate embodiment of the present invention.

PLA:PGA polymers contain PLA and PGA monomers, while PLA polymers contain only PLA monomers. Methods for use and synthesis of PLA polymers and PLA:PGA polymers are well known in the art, and are described, for example, in Fukushima K et al (Macromol Biosci 5(1): 21-9, 2005); Saulnier B et al (Macromol Biosci 15;4(3): 232-7, 2004); and Park S J et al (J Colloid Interface Sci 271(2): 336-41, 2004). Each method represents a separate embodiment of the present invention.

In one embodiment, an implant of methods and compositions of the present invention is rod shaped. As provided herein, results of the present invention show that rod-shaped implants as well as disk-shaped implants can be used to provide extended delivery of risperidone and other drugs. In another embodiment, the implant is disc shaped. In another embodiment, implant is cylindrical. In another embodiment, implant is a sheet. In another embodiment, the implant is any shape suitable for retention in a body tissue (e.g. subcutaneous tissue). In another embodiment, the implant is any shape suitable for structural stability in the subcutaneous space. In another embodiment, the implant is any shape suitable for tolerability in the subcutaneous space. In another embodiment, the implant is any other shape known in the art, "Rod-shaped" refers, in one embodiment, to a shape whose cross-section is substantially round, and whose length is at least twice the diameter of the cross-section. In another embodiment, the cross-sectional shape is any other cross-sectional shape of the present invention. In another embodiment, the length is at least as great as the diameter of the cross-section. In another embodiment, the length is at least 1.1 times the diameter of the cross-section. In another embodiment, the length is at least 1.2 times the diameter In another embodiment, the length is at least 1.3 times the diameter. In another embodiment, the length is at least 1.4 times the diameter. In another embodiment, the length is at least 1.5 times the diameter. In another embodiment, the length is at least 1.6 times the diameter. In another embodiment, the length is at least 1.7 times the diameter In another embodiment, the length is at least 1.8 times the diameter. In another embodiment, the length is at least 1.9 times the diameter. In another embodiment, the length is at least 2.2 times the diameter. In another embodiment, the length is at least 2.5 times the diameter. In another embodiment, the length is at least 3 times the diameter. In another embodiment, the length is at least 4 times the diameter. Each possibility represents a separate embodiment of the present invention.

Figure 16:
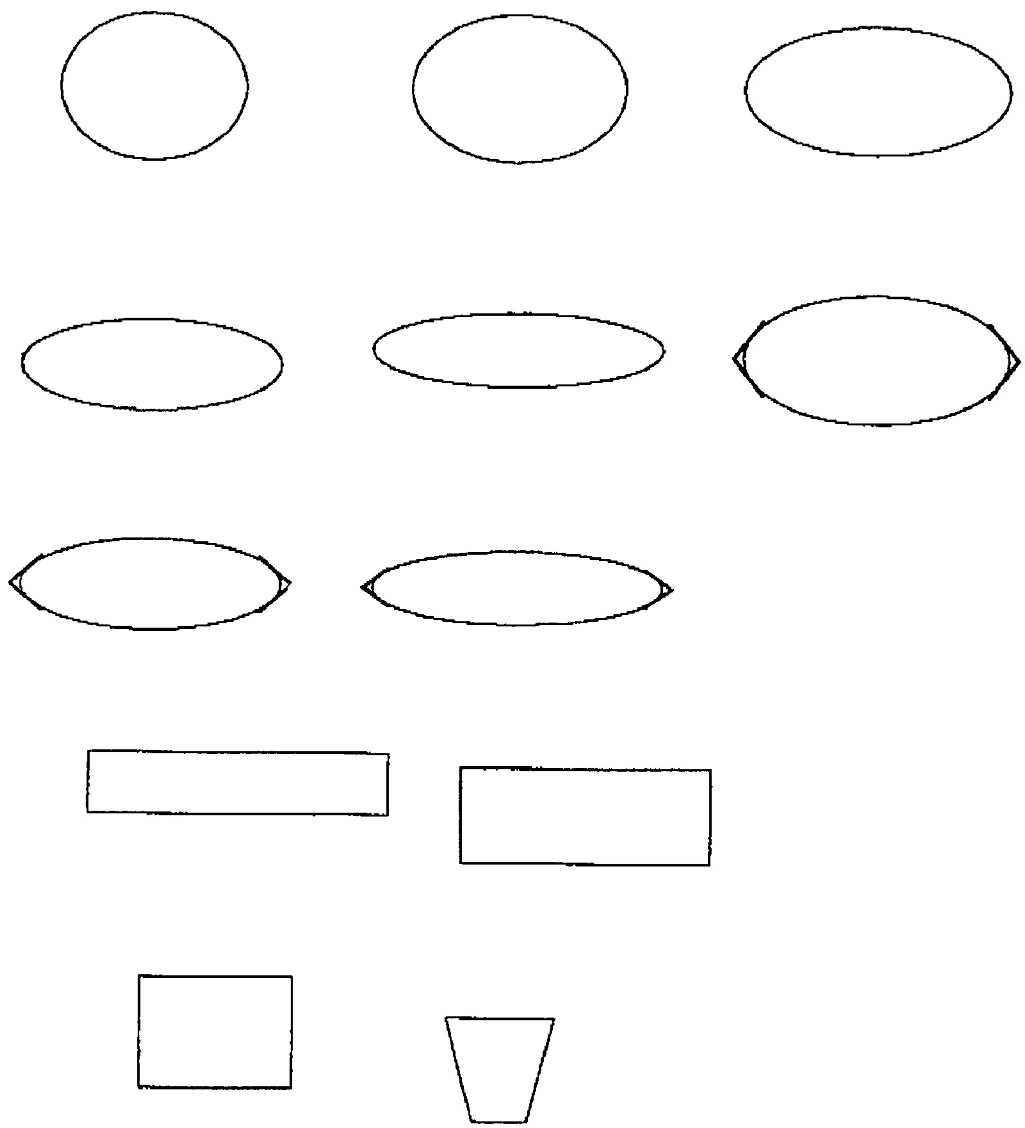
FIG. 16. Representative cross-sectional shapes of rods, disks, and cylinders of implants of the present invention (a non-exhaustive listing).

"Disk-shaped" refers, in one embodiment, to a substantially round, flat shape In another embodiment, the shape is oval, square, rectangular, etc. The thickness is, in one embodiment, less than the diameter of the circle, oval, etc. In another embodiment, the thickness is less than 0.9 times the diameter of the shape. In another embodiment, the thickness is less than 0.8 times the diameter. In another embodiment, the thickness is less than 0.7 times the diameter. In another embodiment, the thickness is less than 0.6 times the diameter. In another embodiment, the thickness is less than 0.5 times the diameter. In another embodiment, the thickness is less than 0.4 times the diameter. In another embodiment, the thickness is less than 0.3 times the diameter. In another embodiment, the thickness is less than 0.2 times the diameter. In another embodiment, the thickness is less than 0.1 times the diameter Each possibility represents a separate embodiment of the present invention In one embodiment, the rods, disks, and cylinders referred to herein have a substantially circular cross-sectional shape In another embodiment, the cross-sectional shape is ellipsoidal. In another embodiment, the ellipsoidal shape need not be round at the edges. In another embodiment, the cross-sectional shape is any shape in FIG. 16. In another embodiment, the cross-sectional shape is any other shape known in the art. Because the present invention has shown that release rate of drug from an implant is proportional to its surface area, the shape of the implant can be modified, in one embodiment, to confer thereupon desirable characteristics without altering the release rate, provided that the surface area remains constant. Similarly, the present invention has shown that duration of release of drug from an implant is proportional to its SA:V ratio; thus, the shape of the implant can be modified, in one embodiment, to confer thereupon desirable characteristics without altering the duration of release, provided that the SA:V ratio remains constant. Each shape represents a separate embodiment of the present invention.

In another embodiment, the cross-sectional area is substantially constant over the length of the rods, disks, and cylinders of the present invention. In another embodiment, the cross-sectional area is not constant. In another embodiment, the cross-sectional dimensions are substantially constant over the length of the rods, disks, and cylinders of the present invention. In another embodiment, the cross-sectional dimensions are not constant. Each possibility represents a separate embodiment of the present invention.

Figure 15A:
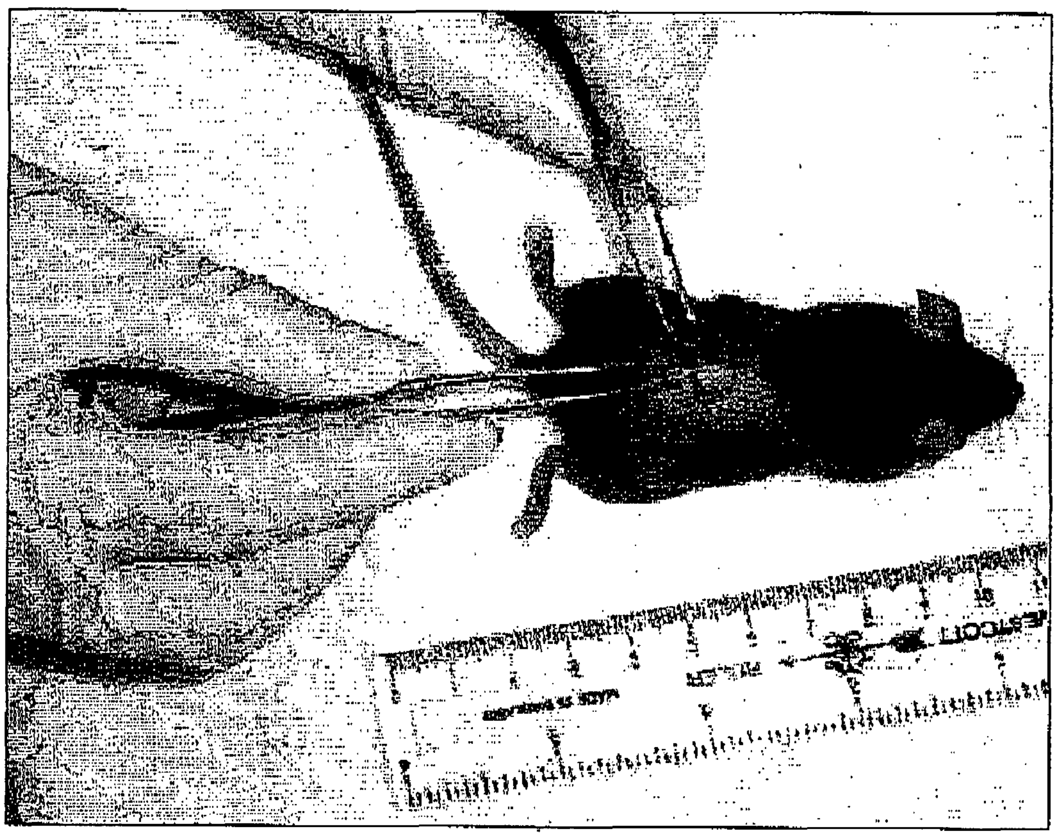
FIG. 15. Insertion of rod-shaped implants. A) Insertion of a 1-cm rod-shaped implant through a 4-mm hole Insert illustrates a 1-cm implant prior to insertion. B) Implant shown in situ after closing with a single stitch. C) Mouse 10 minutes later in home cage without signs of distress.
Figures 15B, 15C:
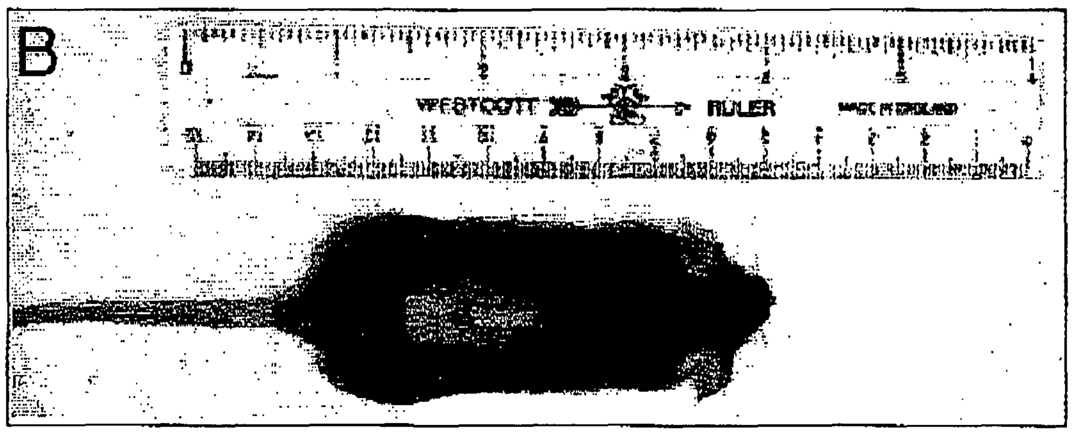

In another embodiment, an implant of the present invention has a rectangular cross-sectional shape. In another embodiment, the cross-sectional shape is a square. In another embodiment, the cross-sectional shape is any other shape known in the art In another embodiment, the implant is monolithic. In another embodiment, the implant is composed of several (10 or fewer) smaller components that are fused together. In another embodiment, the components are linked together. Each possibility represents a separate embodiment of the present invention Each of the above overall shapes and cross-sectional shapes represents a separate embodiment of the present invention Methods of insertion of implants are well known in the art In one embodiment, implants are inserted through a minimally invasive approach, using a surgical instrument known as a "trochar." In another embodiment, the implants are inserted utilizing a procedure and tool set (trochar and obdurator) similar to those used for Norplant (Townsend S "Insertion and removal of Norplant" Netw Fr 6: 8-9, 1991) In another embodiment, rod-shaped implants provide an advantage due to their ease of implantation and lack of subsequent discomfort (FIG. 15) In another embodiment, an advantage of rod-shaped implants is the small incisions required for their insertion; e.g. in various embodiments, about 2 mm, 3 mm, 4 mm, 5 mm, 6 mm, or 7 mm. The incision site is closed, in another embodiment, with either a single stitch or steristrips (FIG. 15). In another embodiment, the implant is inserted by any other surgical method known in the art Each method represents a separate embodiment of the present invention.

In another embodiment, an implant of methods and compositions of the present is tethered (FIG. 2) to assist in locating it and, if necessary, removing it. As provided herein, the removal process has been successfully tested in mice and rats. In another embodiment, following palpation of the implant, a small incision is made and residual material from the implant is retrieved using forceps.

In another embodiment, the implant is removable "Removable" refers, in one embodiment, to the ability of the implant to be removed by surgical or other means. In another embodiment, "removable" refers to the ability of the remains of the implant to be removed. In another embodiment, "removable" refers to the ability of most of the remains of the implant to be removed. In one embodiment, the implant is removed due to an adverse reaction to the medication therein. In another embodiment, the implant is removed due to a decision by the physician In another embodiment, the implant is removed due to a decision by the patient. In another embodiment, the implant is removed due to an overdose of medication. In another embodiment, the implant is removed due to any other reason for which the course of treatment is desired to be halted. Each possibility represents a separate embodiment of the present invention.

In another embodiment, a polymer utilized in methods and compositions of the present invention comprises PLA but not PGA. In another embodiment, the polymer comprises PLA and PGA. In another embodiment, the polymer consists of PLA alone. In another embodiment, the polymer consists of PLA and PGA Each possibility represents a separate embodiment of the present invention.

In another embodiment, the drug load of an implant of methods and compositions of the present invention is between 30-60%. As provided herein (Example 7), results of the present invention have demonstrated the efficacy of particular drug load ranges of biodegradable implants. "Drug load" refers, in one embodiment, to the amount of drug in the implant as a percentage by mass. In another embodiment, "drug load" refers to the percentage by weight of the drug. In another embodiment, e.g if other materials are present in the implant besides the therapeutic drug and the polymer, the drug load is calculated without considering the other materials. Each possibility represents a separate embodiment of the present invention.

In another embodiment, the drug load is between about 40-50%. In another embodiment the drug load is from 1-5%. In another embodiment, the drug load is from 2-5%. In another embodiment, the drug load is from 5-10%. In another embodiment, the drug load is from 10-15%. In another embodiment, the drug load is from 15-20%. In another embodiment, the drug load is from 20-25%. In another embodiment, the drug load is from 25-30%. In another embodiment, the drug load is from 30-35%. In another embodiment, the drug load is from 35-40% In another embodiment, the drug load is from 40-45%. In another embodiment, the drug load is from 45-50%. In another embodiment, the drug load is from 50-55%. In another embodiment, the drug load is from 55-60%. In another embodiment, the drug load is from 60-65%. In another embodiment, the drug load is from 65-70%. In another embodiment, the drug load is from 70-75%. In another embodiment, the drug load is from 75-80%. In another embodiment, the drug load is from 80-85%. In another embodiment, the drug load is from 85-90%. In another embodiment, the drug load is from 90-95%. In another embodiment, the drug load is from 95-99%. In another embodiment, the drug load is from 5-15%. In another embodiment, the drug load is from 10-20%. In another embodiment, the drug load is from 15-25%. In another embodiment, the drug load is from 20-30%. In another embodiment, the drug load is from 25-35%. In another embodiment, the drug load is from 30-40% In another embodiment, the drug load is from 35-45%. In another embodiment, the drug load is from 45-55% In another embodiment, the drug load is from 50-60%. In another embodiment, the drug load is from 55-65%. In another embodiment, the drug load is from 60-70%. In another embodiment, the drug load is from 70-80%. In another embodiment, the drug load is from 80-90% In another embodiment, the drug load is from 90-99%. In another embodiment, the drug load is from 5-20%. In another embodiment, the drug load is from 10-25% In another embodiment, the drug load is from 15-30%. In another embodiment, the drug load is from 20-35%. In another embodiment, the drug load is from 25-40%. In another embodiment, the drug load is from 30-45%. In another embodiment, the drug load is from 35-50%. In another embodiment, the drug load is from 40-55%. In another embodiment, the drug load is from 45-60%. In another embodiment, the drug load is from 50-65%. In another embodiment, the drug load is from 55-70%. In another embodiment, the drug load is from 5-25%. In another embodiment, the drug load is from 10-30%. In another embodiment, the drug load is from 15-35% In another embodiment, the drug load is from 20-40%. In another embodiment, the drug load is from 25-45%. In another embodiment, the drug load is from 30-50%. In another embodiment, the drug load is from 35-55%. In another embodiment, the drug load is from 40-60%. In another embodiment, the drug load is from 45-65%. In another embodiment, the drug load is from 50-70%

In another embodiment, the drug load is 2%. In another embodiment, the drug load is 3%. In another embodiment, the drug load is 5%. In another embodiment, the drug load is 6% In another embodiment, the drug load is 8%. In another embodiment, the drug load is 10%. In another embodiment, the drug load is 12%. In another embodiment, the drug load is 14%. In another embodiment, the drug load is 16%. In another embodiment, the drug load is 18%. In another embodiment, the drug load is 20% In another embodiment, the drug load is 22%. In another embodiment, the drug load is 24%. In another embodiment, the drug load is 26%. In another embodiment, the drug load is 28%. In another embodiment, the drug load is 30%. In another embodiment, the drug load is 32%. In another embodiment, the drug load is 34%. In another embodiment, the drug load is 36%. In another embodiment, the drug load is 38%. In another embodiment, the drug load is 40%. In another embodiment, the drug load is 42%. In another embodiment, the drug load is 44%. In another embodiment, the drug load is 46%. In another embodiment, the drug load is 48%. In another embodiment, the drug load is 50% In another embodiment, the drug load is 52% In another embodiment, the drug load is 54%. In another embodiment, the drug load is 56% In another embodiment, the drug load is 58% In another embodiment, the drug load is 60%. In another embodiment, the drug load is 65%. In another embodiment, the drug load is 70%. Each drug load represents a separate embodiment of the present invention.

Numerical and other ranges used to describe methods and compositions of the present invention are understood to be inclusive of the boundary values Each value or combination of values within the range represents a separate embodiment of the present invention.

A "therapeutic drug" is, in one embodiment, any drug or compound that exhibits any type of therapeutic or beneficial effect when administered to a subject. In another embodiment, the therapeutic drug contained in an implant of methods and compositions of the present invention is risperidone. In another embodiment, the therapeutic drug is 9-OH—risperidone. In another embodiment, the therapeutic drug is thiothixene. In another embodiment, the therapeutic drug is haloperidol. In another embodiment, the therapeutic drug is hydrochlorothiazide (HCTZ). In another embodiment, the therapeutic drug is corticosterone. In another embodiment, the therapeutic drug is ibuprofen. In another embodiment, the therapeutic drug is aspirin. In another embodiment, the therapeutic drug is pimozide. In another embodiment, the therapeutic drug is aripiprazole. In another embodiment, the therapeutic drug is olanzapine In another embodiment, the therapeutic drug is donepezil. In another embodiment, the therapeutic drug is any other therapeutic drug known in the art.

PLA polymers and PLA:PGA polymers exhibit an advantage, in one embodiment, that drugs need not be chemically modified before incorporation therein, rather, they need only be mechanically mixed into the polymeric matrix. Thus, a wide variety of therapeutic agents can be incorporated.

In other embodiments, the therapeutic drug is a dopaminergic agent. In one embodiment, the dopaminergic agent is an agonist. In one embodiment, the dopaminergic agent is an antagonist. In one embodiment, the dopaminergic agent is a partial agonist. In one embodiment, the dopaminergic agent is a monoamine reuptake inhibitor. In one embodiment, the dopaminergic agent is a monoamine uptake facilitators In other embodiments, the therapeutic drug is one of the following drugs, or belongs to one of the following classes: antihypertensives, antidepressants, antianxiety agents, anticlotting agents, anticonvulsants, blood glucose-lowering agents, decongestants, antihistamines, antitussives, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, antibiotics, antiviral agents, anti-neoplastics, barbituates, sedatives, nutritional agents, beta blockers, emetics, antiemetics, diuretics, anticoagulants, cardiotonics, androgens, corticoids, anabolic agents, growth hormone secretagogues, anti-infective agents, coronary vasodilators, carbonic anhydrase inhibitors, antiprotozoals, gastrointestinal agents, serotonin antagonists, anesthetics, hypoglycemic agents, anti-Alzheimer's Disease agents, anti-ulcer agents, platelet inhibitors glycogen phosphorylase inhibitors, and phosphodiesterase inhibitors.

In other embodiments, the therapeutic drug is one of the following drugs: chlorpropamide, fluconazole, atorvastatin calcium, hydroxyzine hydrochloride, doxepin hydrochloride, amlodipine besylate, piroxicam, celicoxib, valdicoxib, carbenicillin indanyl sodium, bacampicillin hydrochloride, troleandomycin, and doxycycline hyclate.

In other embodiments, the therapeutic drug is one of the following drugs, or belongs to one of the following classes: platinum compounds (e.g, spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon alpha.-2b, teniposide (VM-26), vinblastine sulfate (VLB), vincristine sulfate, bleomycin sulfate, hydroxyurea, procarbazine, and dacarbazine; mitotic inhibitors, e.g. etoposide, colchicine, and the vinca alkaloids, radiopharmaceuticals, e.g. radioactive iodine and phosphorus products; hormones, e.g. progestins, estrogens and antiestrogens; anti-helmintics, antimalarials, and antituberculosis drugs; biologicals, e.g. immune serums, antitoxins and antivenoms; rabies prophylaxis products; bacterial vaccines; viral vaccines; respiratory products, e.g. xanthine derivatives theophylline and aminophylline; thyroid agents, e.g. iodine products and anti-thyroid agents; cardiovascular products including chelating agents and mercurial diuretics and cardiac glycosides; glucagon; blood products, e.g. parenteral iron, hemin, hematoporphyrins and their derivatives; biological response modifiers, e.g. muramyldipeptide, muramyltripeptide, microbial cell wall components, lymphokines (e.g., bacterial endotoxin, e.g. lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents, e.g. ketoconazole, nystatin, griseofulvin, flucytosine (5-fc), miconazole, amphotericin B, ricin, cyclosporins, and β-lactam antibiotics (e.g., sulfazecin); hormones, e.g. growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, piednisone, triamcinolone, triamcinolone acetonide, triamcinolone diacetate, triamcinolone hexacetonide, fludrocortisone acetate, oxytocin, vassopressin, and their derivatives; vitamins, e.g. cyanocobalamin neinoic acid, retinoids and derivatives, e.g retinol palmitate, and .alpha.-tocopherol; peptides, e.g manganese super oxide dismutase; enzymes, e.g. alkaline phosphatase; anti-allergic agents, e.g. amelexanox; anti-coagulation agents, e.g phenprocoumon and heparin; circulatory drugs, e.g. propranolol; metabolic potentiators, e.g. glutathione; antituberculars, e.g. para-aminosalicylic acid, isoniazid, capreomycin sulfate cycloserine, ethambutol hydrochloride ethionamide, pyrazinamide, rifampin, and streptomycin sulfate; antivitals, e.g. amantadine azidothymidine (AZT, DDI, Foscarnet, or Zidovudine), ribavirin and vidarabine monohydrate (adenine arabinoside, ara-A); antianginals, e.g. diltiazem, nifedipine, verapamil, erythritol tetranitrate, isosorbide dinitrate, nitroglycerin (glyceryl trinitrate) and pentaerythritol tetranitrate; anticoagulants, e.g. phenprocoumon, heparin; antibiotics, e.g. dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories, e.g. diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans, e.g chloroquine, hydroxychloroquine, metronidazole, quinine and meglumine antimonate; antirheumatics, e.g. penicillamine; narcotics, e.g. paregoric; opiates, e.g. codeine, heroin, methadone, morphine and opium; cardiac glycosides, e.g. deslanoside, digitoxin, digoxin, digitalin and digitalis; neuromuscular blockers, e.g. atracurium mesylate, gallamine triethiodide, hexafluorenium bromide, metocurine iodide, pancuronium biomide, succinylcholine chloride (suxamethonium chloride), tubocurarine chloride and vecuronium bromide; sedatives (hypnotics), e.g. amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics, e.g., bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics, e.g. droperidol, etomidate, fentanyl citrate with dioperidol, ketamine hydrochloride, methohexital sodium and thiopental sodium; and radioactive particles or ions, e.g. strontium, iodide rhenium and yttrium.

In another embodiment, the therapeutic drug is a metabolite of risperidone. In another embodiment, the therapeutic drug is a metabolite of one of the above drug. In one embodiment, the metabolite is an active metabolite.

In another embodiment, the therapeutic drug is a drug that is used chronically.

In another embodiment, the therapeutic drug is a high potency drug "High potency agent" refers, in one embodiment, to a chug that requires a low serum concentration to exert a therapeutic effect. In another embodiment, "high potency agent" refers to a drug that requires a low tissue concentration to exert a therapeutic effect. In another embodiment, "high potency agent" refers to a drug that requires a low systemic concentration to exert a therapeutic effect. Each possibility represents a separate embodiment of the present invention.

In one embodiment, the concentration required for a high potency agent to exert a therapeutic effect is 0.01 mg/kg. In another embodiment, the concentration is 0.02 mg/kg. In another embodiment, the concentration is 0.03 mg/kg. In another embodiment, the concentration is 0.04 mg/kg. In another embodiment, the concentration is 0.05 mg/kg. In another embodiment, the concentration is 0.06 mg/kg. In another embodiment, the concentration is 0.07 mg/kg. In another embodiment, the concentration is 0.08 mg/kg. In another embodiment, the concentration is 0.09 mg/kg. In another embodiment, the concentration is 0.10 mg/kg. In another embodiment, the concentration is 0.12 mg/kg. Each definition of "high potency agent" represents a separate embodiment of the present invention.

Each therapeutic drug represents a separate embodiment of the present invention.

In another embodiment, an implant of methods and compositions of the present invention contains a combination of therapeutic drugs. In one embodiment, the implant contains two therapeutic drugs. In another embodiment, the implant contains three therapeutic drugs. In another embodiment, the implant contains four therapeutic drugs. In another embodiment, the implant contains more than four therapeutic drugs. In another embodiment, the implant contains a combination of one of the above drugs with an additional drug. In another embodiment, the implant contains a combination of two or more drugs not listed above. In another embodiment, the combination of drugs contained in the implant has a synergistic effect. In another embodiment, the combination of drugs contained in the implant has an additive effect. Each possibility represents a separate embodiment of the present invention.

As described above, a wide variety of drugs can be incorporated into PLA polymers and PLA:PGA polymers. Before incorporation, the drug (or "active ingredient") may be prepared by any method known in the art. The preparation of pharmaceutical compositions that contain an active ingredient, for example by mixing, granulating, or tablet-forming processes, is well understood in the art. The active therapeutic ingredient is mixed, in one embodiment, with excipients that are pharmaceutically acceptable and compatible with the active ingredient. In another embodiment, the active ingredient or one of its physiologically tolerated derivatives such as salts, esters, N-oxides, and the like is mixed with additives customary for this purpose, such as vehicles, stabilizers, or inert diluents.

An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

In another embodiment, the PLA:PGA molar ratio of a polymer of methods and compositions of the present invention is between about 0.75:25 and 100:0. In another embodiment, the ratio is between 85:15 and 100:0. In another embodiment, the ratio is from 50:50 and 100:0. In another embodiment, the ratio is from 50:50 and 55:45. In another embodiment, the ratio is from 55:15 and 60:40 In another embodiment, the ratio is from 60:40 and 65:35. In another embodiment, the ratio is from 65:35 and 70:30. In another embodiment, the ratio is from 70:30 and 75:25. In another embodiment, the ratio is from 75:25 and 80:20. In another embodiment, the ratio is from 80:20 and 85:15. In another embodiment, the ratio is from 85:15 and 90:10. In another embodiment, the ratio is from 90:10 and 95:5. In another embodiment, the ratio is from 95:5 and 100:0. In another embodiment, the ratio is from 96:4 and 100:0 In another embodiment, the ratio is from 97:3 and 100:0 In another embodiment, the ratio is from 98:2 and 100:0. In another embodiment, the ratio is from 99:1 and 100:0. In another embodiment, the ratio is from 50:50 and 60:40. In another embodiment, the ratio is from 55:45 and 65:35. In another embodiment, the ratio is from 60:40 and 70:30 In another embodiment, the ratio is from 65:35 and 75:25. In another embodiment, the ratio is from 70:30 and 80:20. In another embodiment, the ratio is from 75:25 and 85:15. In another embodiment, the ratio is from 80:20 and 90:10. In another embodiment, the ratio is from 85:15 and 95:5. In another embodiment, the ratio is from 90:10 and 100:0. In another embodiment, the ratio is from 50:50 and 65:35. In another embodiment, the ratio is from 55:45 and 70:30. In another embodiment, the ratio is from 60:40 and 75:25. In another embodiment, the ratio is from 65:35 and 80:20. In another embodiment, the ratio is from 70:30 and 85:15. In another embodiment, the ratio is from 75:25 and 90:10. In another embodiment, the ratio is from 80:20 and 95:5 In another embodiment, the ratio is from 85:15 and 100:0. In another embodiment, the ratio is from 50:50 and 70:30. In another embodiment, the ratio is from 55:45 and 75:25. In another embodiment, the ratio is from 60:40 and 80:20 In another embodiment, the ratio is from 65:35 and 85:15. In another embodiment, the ratio is from 70:30 and 90:10. In another embodiment, the ratio is from 75:25 and 95:05. In another embodiment, the ratio is from 80:20 and 100:0. In another embodiment, the ratio is from 50:50 and 75:25. In another embodiment, the ratio is from 55:45 and 80:20. In another embodiment, the ratio is from 60:40 and 85:15. In another embodiment, the ratio is from 65:35 and 90:10. In another embodiment, the ratio is from 70:30 and 95:5. In another embodiment, the ratio is from 75:25 and 100:0.

In another embodiment, the ratio is 50:50. In another embodiment, the ratio is 52:48. In another embodiment, the ratio is 54:46. In another embodiment, the ratio is 56:44. In another embodiment, the ratio is 58:42. In another embodiment, the ratio is 60:40. In another embodiment, the ratio is 62:38. In another embodiment, the ratio is 64:36. In another embodiment, the ratio is 66:34 In another embodiment, the ratio is 68:32. In another embodiment, the ratio is 70:30. In another embodiment, the ratio is 72:28. In another embodiment, the ratio is 74:26. In another embodiment, the ratio is 76:24. In another embodiment, the ratio is 78:22. In another embodiment, the ratio is 80:20. In another embodiment, the ratio is 82:18. In another embodiment, the ratio is 84:16. In another embodiment, the ratio is 86:14 In another embodiment, the ratio is 88:12. In another embodiment, the ratio is 90:10. In another embodiment, the ratio is 92:8. In another embodiment, the ratio is 94:6. In another embodiment, the ratio is 96:4. In another embodiment, the ratio is 97:3. In another embodiment, the ratio is 98:2 In another embodiment, the ratio is 99:1. In another embodiment, the ratio is 100:0 (e.g. substantially less than 1% PGA).

As provided herein (Example 5), results of the present invention have demonstrated the efficacy of particular drug PLA:PGA ratios of biodegradable implants In one embodiment, the PLA:PGA ratio is a molar ratio. In another embodiment, the PLA:PGA ratio is a mass ratio. In another embodiment, the PLA:PGA ratio is a weight ratio. In another embodiment, the PLA:PGA ratio is a volume ratio. Each of the above PLA:PGA ratios represents a separate embodiment of the present invention In another embodiment, a polymer of methods and compositions of the present invention exhibits an inherent viscosity of between about 0.2-0.9 dl/g in chloroform. In another embodiment, the inherent viscosity is from 0.6-0.85 dl/g. In another embodiment, the inherent viscosity is from 0.2-0.3 dl/g. In another embodiment, the inherent viscosity is from 0.25-0.35 dl/g. In another embodiment, the inherent viscosity is from 0.3-0.4 dl/g. In another embodiment, the inherent viscosity is from 0.35-0.45 dl/g. In another embodiment, the inherent viscosity is from 0.4-0.5 dl/g. In another embodiment, the inherent viscosity is from 0.45-0.55 dl/g. In another embodiment, the inherent viscosity is from 0.5-0.6 dl/g. In another embodiment, the inherent viscosity is from 0.55-0.65 dl/g. In another embodiment, the inherent viscosity is from 0.6-0.7 dl/g. In another embodiment, the inherent viscosity is from 0.65-0.75 dl/g. In another embodiment, the inherent viscosity is from 0.7-0.8 dl/g. In another embodiment, the inherent viscosity is from 0.75-0.85 dl/g. In another embodiment, the inherent viscosity is from 0.8-0.9 dl/g. In another embodiment, the inherent viscosity is from 0.85-0.95 dl/g In another embodiment, the inherent viscosity is from 0.2-0.35 dl/g. In another embodiment, the inherent viscosity is from 0.25-0.40 dl/g. In another embodiment, the inherent viscosity is from 0.3-0.45 dl/g. In another embodiment, the inherent viscosity is from 0.35-0.5 dl/g. In another embodiment, the inherent viscosity is from 0.4-0.55 dl/g. In another embodiment, the inherent viscosity is from 0.45-0.6 dl/g. In another embodiment, the inherent viscosity is from 0.5-0.65 dl/g. In another embodiment, the inherent viscosity is from 0.55-0.70 dl/g. In another embodiment, the inherent viscosity is from 0.6-0.75 dl/g. In another embodiment, the inherent viscosity is from 0.65-0.80 dl/g. In another embodiment, the inherent viscosity is from 0.7-0.85 dl/g. In another embodiment, the inherent viscosity is from 0.75-0.9 du/g. In another embodiment, the inherent viscosity is from 0.8-0.95 dl/g. In another embodiment, the inherent viscosity is from 0.2-0.40 dl/g. In another embodiment, the inherent viscosity is from 0.25-0.45 dl/g. In another embodiment, the inherent viscosity is from 0.3-0.5 dl/g. In another embodiment, the inherent viscosity is from 0.35-0.55 dl/g. In another embodiment, the inherent viscosity is from 0.4-0.6 dl/g. In another embodiment, the inherent viscosity is from 0.45-0.65 dl/g. In another embodiment, the inherent viscosity is from 0.5-0.7 dl/g. In another embodiment, the inherent viscosity is from 0.55-0.75 du/g. In another embodiment, the inherent viscosity is from 0.6-0.8 dl/g. In another embodiment, the inherent viscosity is from 0.65-0.85 dl/g. In another embodiment, the inherent viscosity is from 0.7-0.9 dl/g. In another embodiment, the inherent viscosity is from 0.75-0.95 dl/g. In another embodiment, the inherent viscosity is from 0.2-0.45 dl/g. In another embodiment, the inherent viscosity is from 0.25-0.5 d/g. In another embodiment, the inherent viscosity is from 0.3-0.55 dl/g. In another embodiment, the inherent viscosity is from 0.35-0.6 dl/g. In another embodiment, the inherent viscosity is from 0.4-0.65 dl/g. In another embodiment, the inherent viscosity is from 0.45-0.7 dl/g. In another embodiment, the inherent viscosity is from 0.5-0.75 dl/g. In another embodiment, the inherent viscosity is from 0.55-0.80 dl/g. In another embodiment, the inherent viscosity is from 0.6-0.85 dl/g. In another embodiment, the inherent viscosity is from 0.65-0.9 dl/g In another embodiment, the inherent viscosity is from 0.7-0.95 dl/g.

In another embodiment, the inherent viscosity is 0.2 dl/g In another embodiment, the inherent viscosity is 0.25 dl/g. In another embodiment, the inherent viscosity is 0.3 dl/g In another embodiment, the inherent viscosity is 0.35 dl/g. In another embodiment, the inherent viscosity is 0.4 dl/g. In another embodiment, the inherent viscosity is 0.45 dl/g. In another embodiment, the inherent viscosity is 0.5 dl/g. In another embodiment, the inherent viscosity is 0.55 dl/g. In another embodiment, the inherent viscosity is 0.6 dl/g. In another embodiment, the inherent viscosity is 0.65 dl/g. In another embodiment, the inherent viscosity is 0.7 dl/g. In another embodiment, the inherent viscosity is 0.75 dl/g. In another embodiment, the inherent viscosity is 0.8 dl/g. In another embodiment, the inherent viscosity is 0.85 dl/g. In another embodiment, the inherent viscosity is 0.9 dl/g. In another embodiment, the inherent viscosity is 0.95 dl/g.

Each of the above inherent viscosities represents a separate embodiment of the present invention.

"Inherent viscosity" refers, in one embodiment, to a measure of the capability of a polymer in solution to enhance the viscosity of the solution In another embodiment, intrinsic viscosity increases with increasing polymer molecular weight, is a function of polymerization conditions, and may be varied independently of the PLA:PGA ratio of the polymer. In another embodiment, intrinsic viscosity is defined as the limiting value of the specific viscosity/concentration ratio at zero concentration. Thus, viscosity is determined at different concentrations and then is extrapolated to zero concentration. In another embodiment, "inherent viscosity" is a synonym for "intrinsic viscosity." Each definition for "inherent viscosity" represents a separate embodiment of the present invention.

Methods for measuring inherent viscosity are well known in the art, and are described, for example, in Meek M F et al (J Biomed Mater Res A 68(1): 43-51, 2004) and Deng X et al (J Control Release 71(2):165-73, 2001) In another embodiment, inherent viscosity is measured as described in Example 1 of the present disclosure. In another embodiment, inherent viscosity is measured in chloroform. In another embodiment, inherent viscosity is measured in hexafluoroisopropanol solution. In another embodiment, inherent viscosity is measured in any other suitable solvent known in the art. In another embodiment, the solvent is an FDA Class III solvent (low toxicity with minimal need for removal of residual solvent). Each method represents a separate embodiment of the present invention.

In another embodiment, an implant of methods and compositions of the present invention has a surface area to volume (SA:V) ratio between about 1 and 3 (millimeters [mm])$^2$/mm$^3$. In another embodiment, the ratio is between 0.5-1 mm$^2$/mm$^3$. In another embodiment, the ratio is from 0.7-1.2 mm$^2$/mm$^3$. In another embodiment, the ratio is from 0.9-1.4 mm$^2$/mm$^3$. In another embodiment, the ratio is from 1.1-1.6 mm$^2$/mm$^3$. In another embodiment, the ratio is from 1.3-1.8 mm$^2$/mm$^3$. In another embodiment, the ratio is from 1.5-2 mm$^2$/mm$^3$. In another embodiment, the ratio is from 2-2.5 mm$^2$/mm$^3$. In another embodiment, the ratio is from 2.5-3 mm$^2$/mm$^3$. In another embodiment, the ratio is from 3-3.5 mm$^2$/mm$^3$. In another embodiment, the ratio is from 3.5-4 mm$^2$/mm$^3$. In another embodiment, the ratio is from 4-4.5 mm$^2$/mm$^3$. In another embodiment, the ratio is from 4.5-5 mm$^2$/mm$^3$. In another embodiment, the ratio is from 5-5.5 mm$^2$/mm$^3$, In another embodiment, the ratio is from 5.5-6 mm$^2$/mm$^3$. In another embodiment, the ratio is between 0.5-1.5 mm$^2$/mm$^3$. In another embodiment, the ratio is from 1-2 mm$^2$/mm$^3$. In another embodiment, the ratio is from 1.5-2.5 mm$^2$/mm$^3$. In another embodiment, the ratio is from 2-3 mm$^2$/mm$^3$. In another embodiment, the ratio is from 2.5-3.5 mm$^2$/mm$^3$. In another embodiment, the ratio is from 3-4 mm$^2$/mm$^3$ In another embodiment, the ratio is from 3.5-4.5 mm$^2$/mm$^3$. In another embodiment, the ratio is from 4-5 mm$^2$/mm$^3$. In another embodiment, the ratio is from 4.5-5.5 mm$^2$/mm$^3$ In another embodiment, the ratio is from 5-6 mm$^2$/mm$^3$. In another embodiment, the ratio is from 5.5-6.5 mm$^2$/mm$^3$. In another embodiment, the ratio is from 6-7 mm$^2$/mm$^3$. In another embodiment, the ratio is from 6.5-7.5 mm$^2$/mm$^3$. In another embodiment, the ratio is from 7-8 mm$^2$/mm$^3$. In another embodiment, the ratio is between 0.5-2 mm$^2$/mm$^3$. In another embodiment, the ratio is from 1-2.5 mm$^2$/mm$^3$. In another embodiment, the ratio is from 1.5-3 mm$^2$/mm$^3$. In another embodiment, the ratio is from 2-3.5 mm$^2$/mm$^3$. In another embodiment, the ratio is from 2.5-4 mm$^2$/mm$^3$. In another embodiment, the ratio is from 3-4.5 mm$^2$/mm$^3$. In another embodiment, the ratio is from 3.5-5 mm$^2$/mm$^3$. In another embodiment, the ratio is from 4-5.5 mm$^2$/mm$^3$. In another embodiment, the ratio is from 4.5-6 mm$^2$/mm$^3$. In another embodiment, the ratio is from 5-6.5 mm$^2$/mm$^3$. In another embodiment, the ratio is from 5.5-7 mm$^2$/mm$^3$. In another embodiment, the ratio is from 6-7.5 mm$^2$/mm$^3$. In another embodiment, the ratio is from 6.5-8 mm$^2$/mm$^3$. In another embodiment, the ratio is from 0.5-2.5 mm$^2$/mm$^3$. In another embodiment, the ratio is from 1-3 mm$^2$/mm$^3$ In another embodiment, the ratio is from 1.5-3.5 mm$^2$/mm$^3$. In another embodiment, the ratio is from 2-4 mm$^2$/mm$^3$. In another embodiment, the ratio is from 2.5-4.5 mm$^2$/mm$^3$ In another embodiment, the ratio is from 3-5 mm$^2$/mm$^3$. In another embodiment, the ratio is from 3.5-5.5 mm$^2$/mm$^3$. In another embodiment, the ratio is from 4-6 mm$^2$/mm$^3$. In another embodiment, the ratio is from 4.5-6.5 mm$^2$/mm$^3$. In another embodiment, the ratio is from 5-7 mm$^2$/mm$^3$. In another embodiment, the ratio is from 5.5-7.5 mm$^2$/mm$^3$ In another embodiment, the ratio is from 6-8 mm$^2$/mm$^3$. In another embodiment, the ratio is between 0.5-3.5 mm$^2$/mm$^3$. In another embodiment, the ratio is from 1-4 mm$^2$/mm$^3$. In another embodiment, the ratio is from 1.5-4.5 mm$^2$/mm$^3$. In another embodiment, the ratio is from 2-5 mm$^2$/mm$^3$. In another embodiment, the ratio is from 2.5-5.5 mm 3. In another embodiment, the ratio is from 3-6 mm$^2$/mm$^3$. In another embodiment, the ratio is from 3.5-6.5 mm$^2$/mm$^3$. In another embodiment, the ratio is from 4-7 mm$^2$/mm$^3$ In another embodiment, the ratio is from 4.5-7.5 mm$^2$/mm$^3$. In another embodiment, the ratio is from 6-8 mm$^2$/mm$^3$. In another embodiment, the ratio is between 0.5-4.5 mm$^2$/mm$^3$. In another embodiment, the ratio is from 1-5 mm$^2$/mm$^3$. In another embodiment, the ratio is from 1.5-5.5 mm$^2$/mm$^3$. In another embodiment, the ratio is from 2-6 mm$^2$/mm$^3$. In another embodiment, the ratio is from 2.5-6.5 mm$^2$/mm$^3$. In another embodiment, the ratio is from 3-7 mm$^2$/mm$^3$. In another embodiment, the ratio is from 3.5-7.5 mm$^2$/mm$^3$. In another embodiment, the ratio is from 4-8 mm$^2$/mm$^3$. In another embodiment, the ratio is from 4.5-8.5

In another embodiment, the ratio is 0.5 mm$^2$/mm$^3$. In another embodiment, the ratio is 0.6 mm$^2$/mm$^3$. In another embodiment, the ratio is 0-7 mm$^2$/mm$^3$. In another embodiment, the ratio is 0.8 mm$^2$/mm$^3$. In another embodiment, the ratio is 1.0 mm$^2$/mm$^3$. In another embodiment, the ratio is 1.5 mm$^2$/mm$^3$. In another embodiment, the ratio is 2 mm$^2$/mm$^3$. In another embodiment, the ratio is 2.5 mm$^2$/mm$^3$. In another embodiment, the ratio is 3 mm$^2$/mm$^3$. In another embodiment, the ratio is 3.5 mm$^2$/mm$^3$. In another embodiment, the ratio is 4 mm$^2$/mm$^3$. In another embodiment, the ratio is 4.5 mm$^2$/mm$^3$. In another embodiment, the ratio is 5 mm$^2$/mm$^3$. In another embodiment, the ratio is 5.5 mm$^2$/mm$^3$. In another embodiment, the ratio is 6 mm$^2$/mm$^3$. In another embodiment, the ratio is 6.5 mm$^2$/mm$^3$. In another embodiment, the ratio is 7 mm$^2$/mm$^3$. Each of the above SA:V ratios represents a separate embodiment of the present invention As provided herein (Example 6), results of the present invention have demonstrated the efficacy of particular SA:V ratio ranges of biodegradable implants. Methods for measuring SA:V ratio are well known in the art. SA:V ratio is measured, in one embodiment, by calculating the surface area and volume from the measurements of the shape (e.g. for a regular shape). In another embodiment (e.g. for an irregular shape), surface area is measured using a BET (Brunauer, Emmett and Teller) apparatus (J de Kanel and J W Morse, J Phys E: Sci Instrum 12:272-273, 1979). In another embodiment, surface area is measured using any other technique known in the art. In another embodiment, volume is measured by displacement of water or another fluid. In another embodiment, volume is measured using any other technique known in the art. Each possibility represents a separate embodiment of the present invention.

In another embodiment, an implant of methods and compositions of the present invention has a length between about 1-5 mm. “Length,” in one embodiment, refers to the longest dimension of the implant In another embodiment, “length” refers to the length of the straight-edge dimension—e.g. in the case of a cylindrical-shaped implant. In another embodiment, the “straight-edge dimension” referred to need not be completely straight, but can be, e.g. a slight curve. Each possibility represents a separate embodiment of the present invention.

In another embodiment, the length of the implant is between 1-2 mm. In another embodiment, the length is from 0.5-1.0 mm. In another embodiment, the length is from 1.5-2 mm. In another embodiment, the length is from 2-2.5 mm. In another embodiment, the length is from 2.5-3 mm. In another embodiment, the length is from 3-3.5 mm. In another embodiment, the length is from 3.5-4 mm. In another embodiment, the length is from 4-4.5 mm. In another embodiment, the length is from 4.5-5 mm. In another embodiment, the length is from 5-5.5 mm. In another embodiment, the length is from 0.5-1.5 mm. In another embodiment, the length is from 1.5-

2.5 mm. In another embodiment, the length is from 2-3 mm. In another embodiment, the length is from 2.5-3.5 mm. In another embodiment, the length is from 3-4 mm. In another embodiment, the length is from 3.5-4.5 mm. In another embodiment, the length is from 4-5 mm. In another embodiment, the length is from 4.5-5.5 mm. In another embodiment, the length is from 5-6 mm. In another embodiment, the length is from 0.5-2 mm. In another embodiment, the length is from 1-2.5 mm. In another embodiment, the length is from 1.5-3 mm. In another embodiment, the length is from 2-3.5 mm. In another embodiment, the length is from 2.5-4 mm. In another embodiment, the length is from 3-4.5 mm In another embodiment, the length is from 3.5-5 mm. In another embodiment, the length is from 4-5.5 mm. In another embodiment, the length is from 4.5-6 mm. In another embodiment, the length is from 0.5-2.5 mm. In another embodiment, the length is from 1-3 mm. In another embodiment, the length is from 1.5-3.5 mm. In another embodiment, the length is from 2-4 mm. In another embodiment, the length is from 2.5-4.5 mm. In another embodiment, the length is from 3-5 mm. In another embodiment, the length is from 3.5-5.5 mm. In another embodiment, the length is from 4-6 mm. In another embodiment, the length is from 4.5-6.5 mm. In another embodiment, the length is from 5-7 mm. In another embodiment, the length is from 0.5-3.5 mm. In another embodiment, the length is from 14 mm. In another embodiment, the length is from 2-5 mm. In another embodiment, the length is from 3-6 mm. In another embodiment, the length is from 4-7 mm. In another embodiment, the length is from 5-8 mm. In another embodiment, the length is from 0.5-4.5 mm. In another embodiment, the length is from 1-5 mm. In another embodiment, the length is from 2-6 mm In another embodiment, the length is from 3-7 mm.

In another embodiment, the length is 0.5 mm. In another embodiment, the length is 0.6 mm. In another embodiment, the length is 0.7 mm. In another embodiment, the length is 0.8 mm. In another embodiment, the length is 0.9 mm. In another embodiment, the length is 1.0 mm. In another embodiment, the length is 1.2 mm. In another embodiment, the length is 1.4 mm. In another embodiment, the length is 1.6 mm. In another embodiment, the length is 1.8 mm. In another embodiment, the length is 2.0 mm. In another embodiment, the length is 2.2 mm. In another embodiment, the length is 2.4 mm. In another embodiment, the length is 2.6 mm. In another embodiment, the length is 2.8 mm. In another embodiment, the length is 3.0 mm. In another embodiment, the length is 3.5 mm. In another embodiment, the length is 4 mm. In another embodiment, the length is 4.5 mm. In another embodiment, the length is 5 mm. In another embodiment, the length is 5.5 mm In another embodiment, the length is 6 mm. In another embodiment, the length is 7 mm. In another embodiment, the length is 8 mm. Each of the above lengths represents a separate embodiment of the present invention.

In another embodiment, an implant of methods and compositions of the present invention has a diameter between about 2-4 mm. “Diameter,” in one embodiment, refers to the distance across the cross-sectional area of the implant. In another embodiment, e.g. in the case of a disk-shaped implant, the distance across the cross-sectional area may be longer than the length described above. In another embodiment, e.g. in the case of a rod-shaped implant, the distance across the cross-sectional area is shorter than the length. In another embodiment, the cross-sectional area referred to need not be a circle, but may be an ellipse, square, rectangle, etc. as described above. Thus, in another embodiment, the diameter is the geometric mean of the longest and shortest diameters of the cross-sectional area. In another embodiment, the diameter is the arithmetic mean of the longest and shortest diameters thereof. In another embodiment, the diameter is the longest of the various diameters thereof. In another embodiment, the diameter is the distance across a diagonal of the cross-sectional area—e.g. in the case of a square or rectangle. In another embodiment, the diameter is the distance across the largest cross-sectional area—e.g. in a case in which the diameter varies over the length of implant. In another embodiment, the diameter is the average distance across the largest cross-sectional area. Each possibility represents a separate embodiment of the present invention.

In another embodiment, the diameter is between about 2-4 mm. In another embodiment, the diameter is from 0.5-1 mm. In another embodiment, the diameter is from 1-1.5 mm. In another embodiment, the diameter is from 1.5-2 mm. In another embodiment, the diameter is from 2-2.5 mm. In another embodiment, the diameter is from 2.5-3 mm. In another embodiment, the diameter is from 3-3.5 mm. In another embodiment, the diameter is from 3.5-4 mm. In another embodiment, the diameter is from 4-4.5 mm. In another embodiment, the diameter is from 4.5-5 mm. In another embodiment, the diameter is from 5-5.5 mm. In another embodiment, the diameter is from 5.5-6 mm. In another embodiment, the diameter is from 0.5-1.5 mm. In another embodiment, the diameter is from 1-2 mm. In another embodiment, the diameter is from 1.5-2.5 mm. In another embodiment, the diameter is from 2-3 mm. In another embodiment, the diameter is from 2.5-3.5 mm. In another embodiment, the diameter is from 3-4 mm. In another embodiment, the diameter is from 3.5-4.5 mm. In another embodiment, the diameter is from 4-5 mm. In another embodiment, the diameter is from 4.5-5.5 mm. In another embodiment, the diameter is from 5-6 mm. In another embodiment, the diameter is from 0.5-2 mm In another embodiment, the diameter is from 1-2.5 mm. In another embodiment, the diameter is from 1.5-3 mm. In another embodiment, the diameter is from 2-3.5 mm. In another embodiment, the diameter is from 2.5-4 mm. In another embodiment, the diameter is from 3-4.5 mm. In another embodiment, the diameter is from 3.5-5 mm. In another embodiment, the diameter is from 4-5.5 mm. In another embodiment, the diameter is from 4-5-6 mm. In another embodiment, the diameter is from 1-3 mm. In another embodiment, the diameter is from 1.5-3.5 mm In another embodiment, the diameter is from 2-4 mm. In another embodiment, the diameter is from 2.5-4.5 mm In another embodiment, the diameter is from 3-5 mm. In another embodiment, the diameter is from 3.5-5.5 mm. In another embodiment, the diameter is from 4-6 mm. In another embodiment, the diameter is from 1-4 mm. In another embodiment, the diameter is from 2-5 mm. In another embodiment, the diameter is from 3-6 mm. In another embodiment, the diameter is from 4-7 mm.

In another embodiment, the diameter is 0.5 mm. In another embodiment, the diameter is 0.6 mm. In another embodiment, the diameter is 0.7 mm. In another embodiment, the diameter is 0.8 mm. In another embodiment, the diameter is 0.9 mm. In another embodiment, the diameter is 1.0 mm. In another embodiment, the diameter is 1.2 mm. In another embodiment, the diameter is 1.4 mm. In another embodiment, the diameter is 1.6 mm. In another embodiment, the diameter is 1.8 mm. In another embodiment, the diameter is 2.0 mm. In another embodiment, the diameter is 2.2 mm. In another embodiment, the diameter is 2.4 mm. In another embodiment, the diameter is 2.6 mm. In another embodiment, the diameter is 2.8 mm. In another embodiment, the diameter is 3.0 mm. In another embodiment, the diameter is 3.2 mm. In another embodiment, the diameter is 3.4 mm. In another embodiment, the diameter is 3.6 mm. In another embodiment, the diameter is 3.8 mm. In another embodiment, the diameter is 4.0 mm. In another embodiment, the diameter is 4.2 mm. In another embodiment, the diameter is 5 mm. In another embodiment, the diameter is 5.5 mm. In another embodiment, the diameter is 6 mm. Each of the above diameters represents a separate embodiment of the present invention.

In another embodiment, an implant of methods and compositions of the present invention has a mass of about 0.75 grams (g) or less. As provided herein, the present invention demonstrates the feasibility of utilizing an implant of about 0.75 g or less for delivery of 6 months' effective dose of risperidone for a human (Example 14). In another embodiment, the present invention demonstrates the feasibility of utilizing an implant of about 1.5 g or less for delivery of one year's effective dose of risperidone. In another embodiment, the implant has a mass of about 0.1 g or less. In another embodiment, the mass is 0.2 g or less. In another embodiment, the mass is 0.3 g or less. In another embodiment, the mass is 0.4 g or less. In another embodiment, the mass is 0.5 g or less. In another embodiment, the mass is 0.6 g or less. In another embodiment, the mass is 0.7 g or less. In another embodiment, the mass is 0.8 g or less. In another embodiment, the mass is 0.9 g or less. In another embodiment, the mass is 1 g or less. In another embodiment, the mass is 1.1 g or less. In another embodiment, the mass is 1.2 g or less. In another embodiment, the mass is 1.3 g or less In another embodiment, the mass is 1.4 g or less. In another embodiment, the mass is 1.5 g or less. In another embodiment, the mass is 1.6 g or less. In another embodiment, the mass is 1.7 g or less. In another embodiment, the mass is 1.8 g or less. In another embodiment, the mass is 1.9 g or less. In another embodiment, the mass is 2 g or less. In another embodiment, the mass is 2.2 g or less. In another embodiment, the mass is 2.4 g or less. In another embodiment, the mass is 2.6 g or less. In another embodiment, the mass is 2.8 g or less. In another embodiment, the mass is 3 g or less.

In another embodiment, the mass is 0.1 g. In another embodiment, the mass is 0.2 g. In another embodiment, the mass is 0.3 g. In another embodiment, the mass is 0.4 g. In another embodiment, the mass is 0.5 g. In another embodiment, the mass is 0.6 g. In another embodiment, the mass is 0.7 g. In another embodiment, the mass is 0.8 g. In another embodiment, the mass is 0.9 g. In another embodiment, the mass is 1 g. In another embodiment, the mass is 1.1 g. In another embodiment, the mass is 1.2 g In another embodiment, the mass is 1.3 g. In another embodiment, the mass is 1.4 g. In another embodiment, the mass is 1.5 g. In another embodiment, the mass is 1.6 g. In another embodiment, the mass is 1.7 g. In another embodiment, the mass is 1.8 g. In another embodiment, the mass is 1.9 g. In another embodiment, the mass is 2 g In another embodiment, the mass is 2.2 g. In another embodiment, the mass is 2.4 g. In another embodiment, the mass is 2.6 g. In another embodiment, the mass is 2.8 g. In another embodiment, the mass is 3 g.

In another embodiment, the mass is between about 0.1-0.3 g. In another embodiment, the mass is from 0.2-0.4 g In another embodiment, the mass is from 0.3-0.5 g. In another embodiment, the mass is from 0.4-0.6 g. In another embodiment, the mass is from 0.5-0.7 g. In another embodiment, the mass is from 0.6-0.8 g. In another embodiment, the mass is from 0.7-0.9 g. In another embodiment, the mass is from 0.8-1.0 g. In another embodiment, the mass is from 0.1-0.4 g. In another embodiment, the mass is from 0.2-0.5 g. In another embodiment, the mass is from 0.3-0.6 g. In another embodiment, the mass is from 0.4-0.7 g. In another embodiment, the mass is from 0.5-0.8 g. In another embodiment, the mass is from 0.6-0.9 g. In another embodiment, the mass is from 0.7-1.0 g. In another embodiment, the mass is from 0.1-0.5 g. In another embodiment, the mass is from 0.2-0.6 g. In another embodiment, the mass is from 0.3-0.7 g. In another embodiment, the mass is from 0.4-0.8 g. In another embodiment, the mass is from 0.5-0.9 g. In another embodiment, the mass is from 0.6-1.0 g. In another embodiment, the mass is from 0.8-1.2 g. In another embodiment, the mass is from 1.0-1.4 g. In another embodiment, the mass is from 1.2-1.6 g. In another embodiment, the mass is from 1.4-1.8 g. In another embodiment, the mass is from 1.6-2 g. In another embodiment, the mass is from 1.8-2.2 g In another embodiment, the mass is from 2-2.4 g. In another embodiment, the mass is from 2.5-2.9 g. In another embodiment, the mass is from 0.1-0.6 g. In another embodiment, the mass is from 0.2-0.7 g In another embodiment, the mass is from 0.3-0.8 g. In another embodiment, the mass is from 0.4-0.9 g. In another embodiment, the mass is from 0.5-1.0 g. In another embodiment, the mass is from 0.6-1.1 g In another embodiment, the mass is from 0.8-1.3 g. In another embodiment, the mass is from 1.0-1.5 g. In another embodiment, the mass is from 1.2-1.7 g. In another embodiment, the mass is from 1.4-1.9 g. In another embodiment, the mass is from 1.6-2.1 g. In another embodiment, the mass is from 1.8-2.3 g. In another embodiment, the mass is from 2-2.5 g. In another embodiment, the mass is from 2.5-3 g. In another embodiment, the mass is from 0.1-0.8 g. In another embodiment, the mass is from 0.2-0.9 g. In another embodiment, the mass is from 0.3-1.1 g. In another embodiment, the mass is from 0.5-1.2 g. In another embodiment, the mass is from 0.6-1.3 g. In another embodiment, the mass is from 0.8-1.5 g . In another embodiment, the mass is from 1.0-1.7 g. In another embodiment, the mass is from 1.2-1.9g . In another embodiment, the mass is from 1.6-2.1 g. In another embodiment, the mass is from 1.8-2.5 g. In another embodiment, the mass is from 2-2.7 g. In another embodiment, the mass is from 0.1-1.1 g. In another embodiment, the mass is from 0.2-1.2 g. In another embodiment, the mass is from 0.3-1.3 g. In another embodiment, the mass is from 0.5-1.5 g. In another embodiment, the mass is from 0.6-1.6 g. In another embodiment, the mass is from 0.8-1.8 g. In another embodiment, the mass is from 1.0-2 g. In another embodiment, the mass is from 1.5-2.5 g In another embodiment, the mass is from 2-3 g. In another embodiment, the mass is from 0.2-1.7 g. In another embodiment, the mass is from 0.3-1.8 g. In another embodiment, the mass is from 0.5-2 g. In another embodiment, the mass is from 0.8-2.3 g. In another embodiment, the mass is from 1.0-2.5 g. In another embodiment, the mass is from 1.5-3 g. In another embodiment, the mass is from 0.2-2.2 g. In another embodiment, the mass is from 0.3-2.3 g. In another embodiment, the mass is from 0.5-2.5 g. In another embodiment, the mass is from 0.8-2.8 g. In another embodiment, the mass is from 1-3 g.

Each of the above masses represents a separate embodiment of the present invention.

In another embodiment, an implant of methods and compositions of the present invention is manufactured by solvent casting. In another embodiment, the implant is manufactured by compression molding. In another embodiment, the implant is manufactured by extrusion molding. In one embodiment, the extrusion molding is high-pressure extrusion molding. In one embodiment, implants manufactured by compression molding exhibit increased density. In another embodiment, implants manufactured by compression molding exhibit improved uniformity. In another embodiment, a greater variety of shapes of implants can be manufactured by compression molding. In another embodiment, less material is lost during fabrication in the case of implants manufactured by extruding. Each possibility represents a separate embodiment of the present invention.

In another embodiment, the present invention provides a method for maintaining a therapeutic level of a drug in a subject for a period of at least about 4 months, comprising administering to the subject a set of biodegradable implants, the set of biodegradable implants consisting of one or more individual biodegradable implants having (a) a therapeutic drug present in an amount of 10%-60% by mass, relative to the mass of the implant; and (b) a polymer present in an amount of 40%-70% by mass, relative to the mass of the implant, the polymer comprising PLA and optionally PGA in a PLA:PGA molar ratio between 50:50 and 100:0 and wherein the individual biodegradable implants, if more than one in number, do not differ substantially from one another in their PLA:PGA molar ratio, thereby maintaining a therapeutic level of a drug in a subject fox a period of at least about 4 months.

In another embodiment, the individual implants are equivalent to one another in another parameter in addition to their PLA:PGA molar ratio, e.g. their drug load, mass, SA:V ratio, length, diameter, or inherent viscosity of the polymer. In another embodiment, the individual implants are equivalent to one another in their PLA:PGA ratio, but not in the other parameters. In another embodiment, the individual implants are equivalent to one another in two of these other parameters in addition to their PLA:PGA ratio. In another embodiment, the individual implants are equivalent to one another in three of these other, parameters in addition to their PLA:PGA ratio. In another embodiment, the individual implants are equivalent to one another in four of these other parameters in addition to their PLA:PGA ratio. In another embodiment, the individual implants are equivalent to one another in five of these other parameters in addition to their PLA:PGA ratio. In another embodiment, the individual implants are equivalent to one another in all of these other parameters in addition to their PLA:PGA ratio Each possibility represents a separate embodiment of the present invention.

In another embodiment, the individual implants are equivalent to one another in their drug load instead of in their PLA:PGA ratio. In another embodiment, the individual implants are equivalent to one another in their mass instead of in their PLA:PGA ratio. In another embodiment, the individual implants are equivalent to one another in their SA:V ratio instead of in their PLA:PGA ratio. In another embodiment, the individual implants are equivalent to one another in their length instead of in their PLA:PGA ratio In another embodiment, the individual implants are equivalent to one another in their diameter instead of in their PLA:PGA ratio. In another embodiment, the individual implants ate equivalent to one another in the inherent viscosity of their polymer instead of in their PLA:PGA ratio. In another embodiment, the individual implants ale equivalent to one another in 2 of these parameters. In another embodiment, the individual implants are equivalent to one another in 3 of these parameter s. In another embodiment, the individual implants are equivalent to one another in 4 of these parameters. In another embodiment, the individual implants are equivalent to one another in all of these parameters. Each possibility represents a separate embodiment of the present invention.

In another embodiment, the PLA:PGA ratio is substantially invariant within the individual implants; e.g. the individual implants ale not each composed of sections with different PLA:PGA ratios. In another embodiment, this is true of the drug load of the individual implants. In another embodiment, this is true of the mass of the individual implants. In another embodiment, this is true of the SA:V ratio of the individual implants In another embodiment, this is true of the length of the individual implants. In another embodiment, this is true of the diameter of the individual implants In another embodiment, this is true of the inherent viscosity of the polymer in the individual implants. Each possibility represents a separate embodiment of the present invention.

Figure 3A:
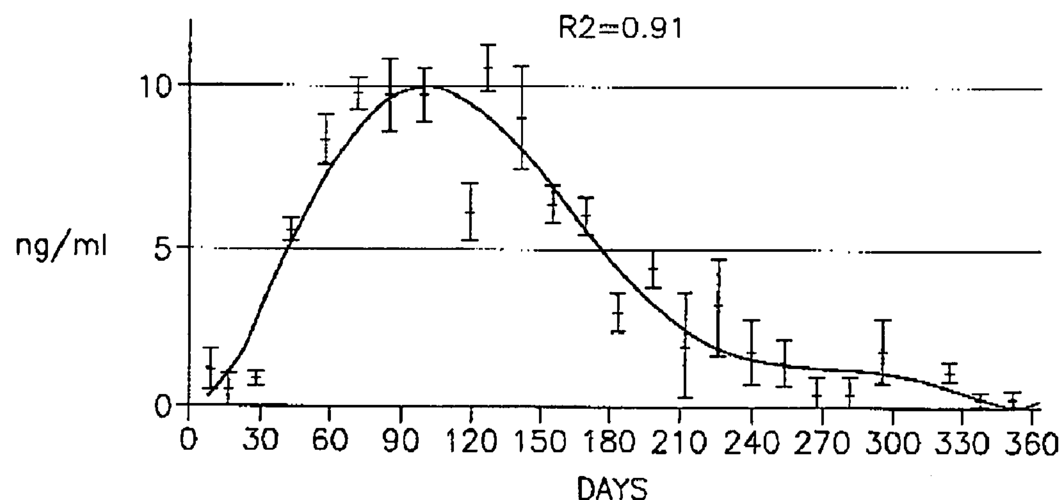
Figure 3B:
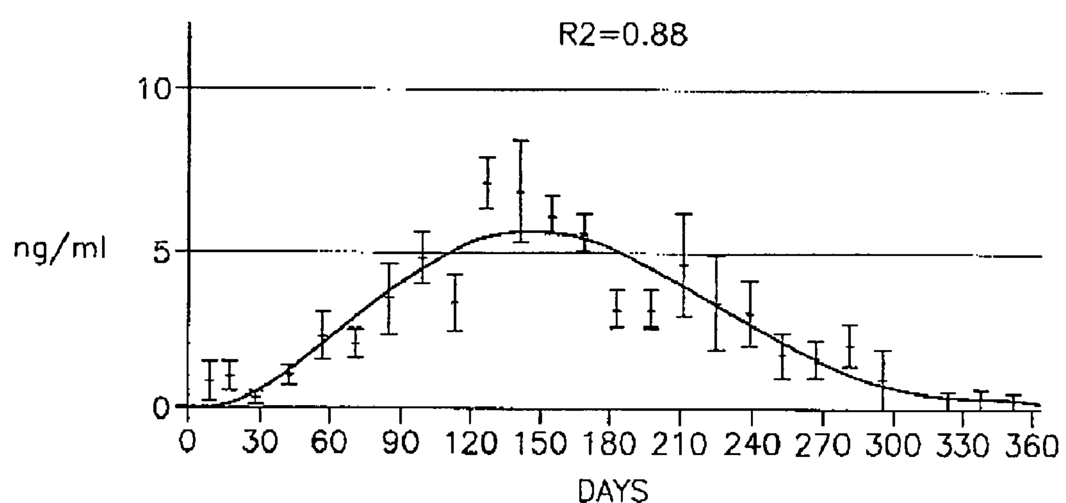

As provided herein, the present invention demonstrates that extended maintenance of therapeutic drug levels can be attained with a single-polymer system (e.g. a homogenous set of implants). Furthermore, the single-polymer implant system in rabbits (FIG. 3B) demonstrated that individual polymers approximate a symmetrical pattern of serum concentration. Moreover, as depicted in FIG. 3B, the trendline that described that data with a correlation coefficient (R2) of 0.86 exhibited maximum release values at approximately 6 months.

In another embodiment, the present invention provides a method for maintaining a therapeutic level of a drug in a subject for a period of at least about one year, comprising (1) administering to the subject an initial set of one or more biodegradable implants, wherein the initial set consists of one or more individual biodegradable implants having (a) a therapeutic drug present in an amount of 10%-60% by mass, relative to the mass of the implant; and (b) a polymer present in an amount of 40%-70% by mass, relative to the mass of the implant, the polymer comprising PLA and optionally PGA in a PLA:PGA molar ratio between 50:50 and 100:0; and (2) administering to the subject a maintenance set of one or more biodegradable implants to the subject near the point of peak release of the initial set of biodegradable implants, wherein the maintenance set of biodegradable implants consists of additional individual biodegradable implants equivalent in the PLA:PGA molar ratio to the individual biodegradable implants in the initial set of biodegradable implants. In this method, the individual biodegradable implants of the initial set, if more than one in number, do not differ substantially from one another in their PLA:PGA molar ratio, thereby maintaining a therapeutic level of a drug in a subject for a period of at least about one year.

In another embodiment, the present invention provides a method for maintaining a therapeutic level of a drug in a subject for a period of at least about 6 months, comprising (1) administering to the subject an initial set of one or more biodegradable implants, wherein the initial set consists of one or more individual biodegradable implants having (a) a therapeutic drug present in an amount of 10%-60% by mass, relative to the mass of the implant; and (b) a polymer present in an amount of 40%-70% by mass, relative to the mass of the implant, the polymer comprising PLA and optionally PGA in a PLA:PGA molar ratio between 50:50 and 100:0; and (2) administering to the subject a maintenance set of one or more biodegradable implants to the subject near the point of peak release of the initial set of biodegradable implants, wherein the maintenance set of biodegradable implants consists of additional individual biodegradable implants equivalent in the PLA:PGA molar ratio to the individual biodegradable implants in the initial set of biodegradable implants In this method, the individual biodegradable implants of the initial set, if more than one in number, do not differ substantially from one another in their PLA:PGA molar ratio, thereby maintaining a therapeutic level of a drug in a subject for a period of at least about 6 months.

In another embodiment, the individual biodegradable implants of the maintenance set, if more than one in number, do not differ substantially from one another in their PLA:PGA molar ratio. In another embodiment, the individual biodegradable implants of the initial set and the maintenance set do not differ substantially from one another, both within and between the sets, in their PLA:PGA molar ratio. Each possibility represents a separate embodiment of the present invention.

In another embodiment, step (b) is repeated as necessary to maintain therapeutic level of the drug for the desired time period in the subject In another embodiment, the maintenance set is administered near the time of beginning of decline of drug release of the prior set of implants.

In one embodiment, the maintenance set is administered about once every 6 month. In another embodiment, the maintenance set is administered after a period of about 5 months. In another embodiment, the period is about 4 months. In another embodiment, the period is about 3 months. In another embodiment, the period is about 2 months. In another embodiment, the period is about 6 weeks. In another embodiment, the period is about 1 month. In another embodiment, the period is about 7 months. In another embodiment, the period is about 8 months. In another embodiment, the period is about 9 months. In another embodiment, the period is about 1.0 months. In another embodiment, the period is about 11 months. In another embodiment, the period is about 12 months. In another embodiment, the period is about 14 months. In another embodiment, the period is about 16 months. In another embodiment, the period is about 18 months. In another embodiment, the period is about 20 months. In another embodiment, the period is about 22 months. In another embodiment, the period is about 24 months. In another embodiment, the period is about 30 months. In another embodiment, the period is about 36 months. Each possibility represents a separate embodiment of the present invention.

In another embodiment, the individual implants of the maintenance set are equivalent to the individual implants in the initial set in another parameter in addition to their PLA:PGA molar ratio, e.g their drug load, mass, SA:V ratio, length, diameter, ox inherent viscosity of the polymer. In another embodiment, the individual implants of the maintenance set are equivalent to the individual implants in the initial set in one of these parameters instead of their PLA:PGA molar ratio. In another embodiment, the individual implants from the maintenance set are equivalent to the individual implants in the initial set in their PLA:PGA ratio, but not in the other parameters. In another embodiment, the individual implants from the maintenance set are equivalent to the individual implants in the initial set in two of these other parameters in addition to their PLA:PGA ratio. In another embodiment, the individual implants from the maintenance set are equivalent to the individual implants in the initial set in three of these other parameters in addition to their PLA:PGA ratio. In another embodiment, the individual implants from the maintenance set are equivalent to the individual implants in the initial set in four of these other parameters in addition to their PLA:PGA ratio. In another embodiment, the individual implants from the maintenance set are equivalent to the individual implants in the initial set in five of these other parameters in addition to their PLA:PGA ratio. In another embodiment, the individual implants from the maintenance set are equivalent to the individual implants in the initial set in all of these other parameters in addition to their PLA:PGA ratio. In another embodiment, the individual implants from the maintenance set are equivalent to the individual implants in the initial set in two of these other parameters, but not their PLA:PGA ratio. In another embodiment, the individual implants from the maintenance set ale equivalent to the individual implants in the initial set in three of these other parameters, but not their PLA:PGA ratio. In another embodiment, the individual implants from the maintenance set are equivalent to the individual implants in the initial set in four of these other parameters, but not their PLA:PGA ratio. In another embodiment, the individual implants from the maintenance set ale equivalent to the individual implants in the initial set in five of these other parameters, but not their PLA:PGA ratio. Each possibility represents a separate embodiment of the present invention.

In other embodiments, the individual implants of the maintenance set have any of the characteristics described above for the individual implants of the initial set. Each characteristic represents a separate embodiment of the present invention.

The nearly symmetrical nature of the release profile from single-polymer sets, as demonstrated in the present invention, provides the possibility of using overlapping implantations approximately every 6 months to sustain drug delivery indefinitely (FIG. 13). In one embodiment this approach offsets the steady decline from one set of implants with the gradual onset from a subsequent set.

In another embodiment, the time period over which the therapeutic level of a drug is maintained by methods of the present invention is one month. In another embodiment, the period is 1.5 months. In another embodiment, the period is 2 months. In another embodiment, the period is 2.5 months. In another embodiment, the period is 3 months. In another embodiment, the period is 3.5 months. In another embodiment, the period is 4 months. In another embodiment, the period is 5 months. In another embodiment, the period is 6 months. In another embodiment, the period is 7 months. In another embodiment, the period is 8 months. In another embodiment, the period is 9 months. In another embodiment, the period is 10 months. In another embodiment, the period is 11 months. In another embodiment, the period is 12 months. In another embodiment, the period is 13 months. In another embodiment, the period is 14 months. In another embodiment, the period is 15 months. In another embodiment, the period is 16 months. In another embodiment, the period is 17 months. In another embodiment, the period is 18 months.

In another embodiment, the period begins 1 month after the step of administering the initial set of biodegradable implants. In another embodiment, the period begins 1 week after the initial administration. In another embodiment, the period begins 2 weeks after the initial administration. In another embodiment, the period begins 3 weeks after the initial administration. In another embodiment, the period begins 5 weeks after the initial administration. In another embodiment, the period begins 6 weeks after the initial administration. In another embodiment, the period begins 2 months after the initial administration. In another embodiment, the period begins 2.5 months after the initial administration. In another embodiment, the period begins 3 months after the initial administration Each of the above periods represents a separate embodiment of the present invention.

In another embodiment, a method of the present invention further comprises administering to the subject a starter set of one or more different biodegradable implants, wherein the implants of the starter set differ from the implants of the original set of implants in PLA:PGA ratio, and whereby the implants of the starter set reach steady-state levels of drug release faster than the initial set of implants. In another embodiment, the implants of the starter set differ from the implants of the original set of implants in their drug load. In another embodiment, the starters set implants differ from original set of implants in their SA:V ratio. In another embodiment, the starter set implants differ from the original set of implants in their mass. In another embodiment, the starter set implants differ from the original set of implants in their length In another embodiment, the starter set implants differ from the original set of implants in their diameter. In another embodiment, the starter set implants differ from the original set of implants in the inherent viscosity of their polymer. In another embodiment, the implants of the starter set differ from the original set of implants in 2 of these characteristics In another embodiment, the starter set implants differ from the original set of implants in 3 of these characteristics. In another embodiment, the starter set implants differ from the original set of implants in 4 of these characteristics. In another embodiment, the starter set implants differ from the original set of implants in all of these characteristics. Each possibility represents a separate embodiment of the present invention.

In another embodiment, the implants of the starter set do not differ substantially from one another in their PLA:PGA ratio, drug load, length, diameter, SA:V ratio, and inherent viscosity. In another embodiment, the starter set implants differ substantially from one another in one of these par meters. In another embodiment, the starter set implants differ substantially from one another in more than one of these parameters. In another embodiment, the starter set implants have different release profiles from one another. Each possibility represents a separate embodiment of the present invention In other embodiments, the starter set implants have any of the characteristics described above for the individual implants of the initial set. Each characteristic represents a separate embodiment of the present invention.

In another embodiment, in methods of the present invention that comprise an initial set of implants and a maintenance set of equivalent implants, the starter set implants are administered together with the initial set of implants. "Together with," in one embodiment, refers to administration on the same day as the other set of one or more implants. In another embodiment, "together with" refers to administration during a single operation or procedure. In another embodiment, the term refers to administration within one day of the other set of implants. In another embodiment, the term refers to administration within 2 days of the other set of implants. In another embodiment, the term refers to administration within 3 days of the other set of implants. In another embodiment, the term refers to administration within 4 days of the other set of implants. In another embodiment, the term refers to administration within one week of the other set of implants. In another embodiment, the term refers to administration within 2 weeks of the other set of implants. In another embodiment, the term refers to administration within 3 weeks of the other set of implants. In another embodiment, the term refers to administration within one month of the other set of implants In another embodiment, the term refers to administration within 2 months of the other set of implants Each possibility represents a separate embodiment of the present invention.

In another embodiment, the starter set implants enable earlier attainment of therapeutic drug levels, as provided herein (Example 16). In another embodiment, the number of implants required in the initial set of implants is reduced (relative to the maintenance set of implants) due to the present of the starter set implants, as the starter set implants make a contribution to the drug levels that is not present at the time of administration of the maintenance set of implants The ability of starter sets to enable mote rapid release was shown in the present invention, by comparing the release profiles of the single-polymer design to the multiple-polymer design. Higher serum levels were observed in early time points with the multiple-polymer design (FIGS. 1 and 3A).

In another embodiment, instead of administering a starter set of implants with the initial implantation, the number of implants is increased (relative to the maintenance set of implants) to attain therapeutic levels more quickly.

In another embodiment, the step of administering the initial set of implants is reversible In another embodiment, the step of administering the starter set of implants is reversible. "Reversible," in one embodiment, refers to the ability to remove the remains of the set of implants by surgical or other means. In one embodiment, "reversible" refers to the ability to remove the remains of one or more of the implants. In another embodiment, "reversible" refers to the ability to remove the majority of the remains of the set of implants. In another embodiment, "reversible" refers to the ability to remove the majority of the remains of one or more of the implants. Each possibility represents a separate embodiment of the present invention.

In one embodiment, the subject of methods of the present invention is human. In another embodiment, the subject is a primate. In another embodiment, the subject is a mammal. In another embodiment, the subject is a rodent In another embodiment, the subject is a laboratory animal. In another embodiment, the subject is a domestic animal. In another embodiment, the subject is a male. In another embodiment, the subject is a female. In another embodiment, the subject is any other type of subject known in the art. Each possibility represents a separate embodiment of the present invention.

In other embodiments, the individual implants of any of the sets described above have any of the lengths of an implant of the present invention. In other embodiments, the individual implants have a combined length equal to any of the lengths of an implant of the present invention.

In another embodiment, the step of administering the individual implants of any of the above sets is reversible. In another embodiment, the step of administering any of the above sets is reversible. In one embodiment, "reversible" refers to one of the meanings provided above. Each possibility represents a separate embodiment of the present invention.

In other embodiments the individual implants of any of the above sets have any of the diameters of an implant of the present invention. In other embodiments, the individual implants have a combined length equal to any of the diameters of an implant of the present invention.

In other embodiments, the individual implants of any of the above sets have any of the SA:V ratios of an implant of the present invention. In other embodiments, the individual implants have a combined length equal to any of the SA:V ratios of an implant of the present invention.

In other embodiments, the individual implants of any of the above sets have any of the masses of an implant of the present invention In other embodiments, the individual implants have a combined length equal to any of the masses of an implant of the present invention.

In another embodiment, the individual implants of any of the above sets are combined into a single structure (e.g. a rod-shaped structure, a bundle, etc.). In another embodiment, the structure has any of the lengths of an implant of the present invention. In another embodiment, the structure has any of the diameters of an implant of the present invention. In another embodiment, the structure has any of the SA:V ratios of an implant of the present invention. In another embodiment, the structure has any of the masses of an implant of the present invention. In another embodiment, the structure enables reduction of the number of structures implanted. Each possibility represents a separate embodiment of the present invention.

In other embodiments, the individual biodegradable implants of any of the sets described above have any of the characteristics of an implant of the present invention. Each characteristic represents a separate embodiment of the present invention.

In another embodiment, a method of the present invention further comprises administration of the therapeutic drug by a different route, together with the initial administration of implants, in order to reach and maintain therapeutic drug levels until the rate of release of the implants is sufficient. In another embodiment, a different drug with a similar therapeutic effect is administered with the initial set of implants. Any route of administration known in the art may be used. Each route represents a separate embodiment of the present invention.

In another embodiment, the present invention provides a method for releasing a therapeutic drug at a substantially linear late for a period of several months into a body tissue of a subject, comprising administering to the subject an implant or set of implants of the present invention, thereby releasing a therapeutic drug at a substantially linear rate for a period of several months into a body tissue of a subject.

In another embodiment, the present invention provides a method for releasing thiothixene at a substantially linear late for a period of several months into a body tissue of a subject, comprising administering to the subject a thiothixene-containing implant of the present invention, thereby releasing thiothixene at a substantially linear rate for a period of several months.

In another embodiment, the present invention provides a method for releasing haloperidol at a substantially linear rate for a period of several months into a body tissue of a subject, comprising administering to the subject a haloperidol-containing implant of the present invention, thereby releasing haloperidol at a substantially linear late for a period of several months.

In another embodiment, the present invention provides a method for releasing HCTZ at a substantially linear late for a period of several months into a body tissue of a subject, comprising administering to the subject a HCTZ-containing implant of the present invention, thereby releasing HCTZ at a substantially linear rate for a period of several months.

In another embodiment, the present invention provides a method for releasing ibuprofen at a substantially linear late for a period of several months into a body tissue of a subject, comprising administering to the subject an ibuprofen-containing implant of the present invention, thereby releasing ibuprofen at a substantially linear rate for a period of several months.

In another embodiment, the present invention provides a method for releasing aspirin at a substantially linear rate for a period of several months into a body tissue of a subject, comprising administering to the subject an aspirin-containing implant of the present invention, thereby releasing aspirin at a substantially linear late for a period of several months.

In another embodiment, the present invention provides a method for releasing corticosterone at a substantially linear late for a period of several months into a body tissue of a subject, comprising administering to the subject a corticosterone-containing implant of the present invention, thereby releasing corticosterone at a substantially linear rate for a period of several months.

"Several months" refers, in various embodiments, to anytime period of the present invention. Each time period represents a separate embodiment of the present invention.

In another embodiment, the present invention provides a method for releasing a therapeutic drug at a substantially linear rate for a period of several weeks into a body tissue of a subject, comprising administering to the subject an implant or set of implants of the present invention, thereby releasing a therapeutic drug at a substantially linear late for a period of several weeks into a body tissue of a subject.

The therapeutic drug is, in various embodiments, any therapeutic drug of the present invention. Each drug represents a separate embodiment of the present invention.

In one embodiment, the substantially linear rate of methods and compositions of the present invention is the release rate of the implant during the steady state phase of release. "Steady state," in one embodiment, refers to the period of time during which an implant exhibits a substantially linear release rate, as exemplified herein in Example 10.

In one embodiment, the substantially linear late is 0.1 mg/day. In another embodiment, the rate is 0.2 mg/day. In another embodiment, the late is 0.3 mg/day. In another embodiment, the rate is 0.4 mg/day. In another embodiment, the rate is 0.5 mg/day. In another embodiment, the late is 0.6 mg/day. In another embodiment, the rate is 0.8 mg/day. In another embodiment, the rate is 1 mg/day. In another embodiment, the late is 1.2 mg/day. In another embodiment, the late is 1.5 mg/day. In another embodiment, the late is 1.8 mg/day. In another embodiment, the rate is 2.0 mg/day. In another embodiment, the rate is 2.5 mg/day. In another embodiment, the rate is 3 mg/day. In another embodiment, the rate is 3.5 mg/day. In another embodiment, the rate is 4 mg/day. In another embodiment, the late is 5 mg/day. In another embodiment, the late is 6 mg/day. In another embodiment, the late is 7 mg/day. In another embodiment, the rate is 8 mg/day. In another embodiment, the late is 10 mg/day. Each late represents a separate embodiment of the present invention.

In another embodiment, the late is between about 0.1-0.3 mg/day. In another embodiment, the rate is from 0.2-0.4 mg/day. In another embodiment, the late is from 0.3-0.5 mg/day. In another embodiment, the late is from 0.4-0.6 mg/day. In another embodiment, the rate is from 0.5-0.7 mg/day. In another embodiment, the rate is from 0.6-0.8 mg/day. In another embodiment, the late is from 0.7-0.9 mg/day. In another embodiment, the rate is from 0.8-1.0 mg/day. In another embodiment, the rate is from 0.1-0.4 mg/day. In another embodiment, the rate is from 0.2-0.5 mg/day. In another embodiment, the rate is from 0.3-0.6 mg/day. In another embodiment, the rate is from 0.4-0.7 mg/day. In another embodiment, the rate is from 0.5-0.8 mg/day. In another embodiment, the rate is from 0.6-0.9 mg/day. In another embodiment, the late is from 0.8-1.1 mg/day. In another embodiment, the rate is from 1.0-1.3 mg/day. In another embodiment, the rate is from 1.5-1.8 mg/day. In another embodiment, the late is from 0.1-0.5 mg/day. In another embodiment, the late is from 0.2-0.6 mg/day. In another embodiment, the rate is from 0.3-0.7 mg/day. In another embodiment, the late is from 0.4-0.8 mg/day. In another embodiment, the late is from 0.5-0.9 mg/day. In another embodiment, the rate is from 0.6-1.0 mg/day. In another embodiment, the rate is from 0.8-1.2 mg/day. In another embodiment, the rate is from 1.0-1.4 mg/day. In another embodiment, the rate is from 1.5-1.9 mg/day. In another embodiment, the rate is from 2-2.4 mg/day. In another embodiment, the rate is from 0.1-0.6 mg/day. In another embodiment, the rate is from 0.2-0.7 mg/day. In another embodiment, the rate is from 0.3-0.8 mg/day. In another embodiment, the rate is from 0.5-1.0 mg/day. In another embodiment, the late is from 0.6-1.1 mg/day. In another embodiment, the rate is from 0.8-1.3 mg/day. In another embodiment, the rate is from 1.0-1.5 mg/day. In another embodiment, the rate is from 1.5-2 mg/day In another embodiment, the rate is from 2-2.5 mg/day. In another embodiment, the rate is from 2.5-3 mg/day. In another embodiment, the rate is from 3-3.5 mg/day. In another embodiment, the rate is from 3.5-4 mg/day. In another embodiment, the rate is from 4-4.5 mg/day In another embodiment, the late is from 0.3-1.3 mg/day. In another embodiment, the rate is from 0.5-1.5 mg/day. In another embodiment, the rate is from 0.8-1.8 mg/day. In another embodiment, the rate is from 1.0-2 mg/day. In another embodiment, the rate is from 1.5-2.5 mg/day. In another embodiment, the rate is from 2-3 mg/day. In another embodiment, the late is from 2.5-3.5 mg/day. In another embodiment, the rate is from 3-4 mg/day. In another embodiment, the rate is from 3.5-4.5 mg/day In another embodiment, the rate is from 4-5 mg/day. In another embodiment, the late is from 0.5-2 mg/day. In another embodiment, the rate is from 1.0-2.5 mg/day. In another embodiment, the rate is from 1.5-3 mg/day. In another embodiment, the rate is from 2-3.5 mg/day. In another, embodiment, the sate is from 2.5-4 mg/day. In another embodiment, the rate is from 3-4.5 mg/day. In another embodiment, the rate is from 3.5-5 mg/day. In another embodiment, the rate is from 0.5-2.5 mg/day In another embodiment, the rate is from 1-3 mg/day. In another embodiment, the rate is from 1.5-3.5 mg/day. In another embodiment, the rate is from 2-4 mg/day. In another embodiment, the rate is from 2.5-4.5 mg/day. In another embodiment, the rate is from 3-5 mg/day. In another embodiment, the rate is from 1-4 mg/day. In another embodiment, the rate is from 1.5-4.5 mg/day. In another embodiment, the rate is from 2-5 mg/day. In another embodiment, the rate is from 3-6 mg/day.

Each of the above rates represents a separate embodiment of the present invention.

In another embodiment, the present invention provides a method for releasing risperidone at a substantially linear rate for a period of at least 1 month into a body tissue of a subject, comprising administering to the subject a risperidone-containing implant or set of implants of the present invention, thereby releasing risperidone at a substantially linear rate for a period of at least 1 month into a body tissue of a subject.

In another embodiment, the present invention provides a method for releasing risperidone at a substantially linear rate for a period of at least 2 months into a body tissue of a subject, comprising administering to the subject a risperidone-containing implant or set of implants of the present invention, thereby releasing risperidone at a substantially linear rate for a period of at least 2 months into a body tissue of a subject.

In another embodiment, the present invention provides a method for releasing risperidone at a substantially linear rate for a period of at least 3 months into a body tissue of a subject, comprising administering to the subject a risperidone-containing implant or set of implants of the present invention, thereby releasing risperidone at a substantially linear, rate for a period of at least 3 months into a body tissue of a subject.

In another embodiment, the present invention provides a method for releasing risperidone at a substantially linear rate for a period of at least 4 months into a body tissue of a subject, comprising administering to the subject a risperidone-containing implant or set of implants of the present invention, thereby releasing risperidone at a substantially linear rate for a period of at least 4 months into a body tissue of a subject.

In another embodiment, the present invention provides a method for releasing risperidone at a substantially linear rate for a period of at least 5 months into a body tissue of a subject, comprising administering to the subject a risperidone-containing implant or set of implants of the present invention, thereby releasing risperidone at a substantially linear rate for a period of at least 5 months into a body tissue of a subject.

In another embodiment, the present invention provides a method for releasing risperidone at a substantially linear rate fox a period of at least 6 months into a body tissue of a subject, comprising administering to the subject a risperidone-containing implant or set of implants of the present invention, thereby releasing risperidone at a substantially linear rate for a period of at least 6 months into a body tissue of a subject.

In another embodiment, the present invention provides a method for releasing risperidone at a substantially linear rate for a period of at least 7 months into a body tissue of a subject, comprising administering to the subject a risperidone-containing implant or set of implants of the present invention, thereby releasing risperidone at a substantially linear rate for a period of at least 7 months into a body tissue of a subject.

In another embodiment, the present invention provides a method for releasing risperidone at a substantially linear rate for a period of at least 8 months into a body tissue of a subject, comprising administering to the subject a risperidone-containing implant or set of implants of the present invention, thereby releasing risperidone at a substantially linear rate for a period of at least 8 months into a body tissue of a subject.

In another embodiment, the present invention provides a method for releasing risperidone at a substantially linear rate for a period of at least 9 months into a body tissue of a subject, comprising administering to the subject a risperidone-containing implant or set of implants of the present invention, thereby releasing risperidone at a substantially linear rate for a period of at least 9 months into a body tissue of a subject In another embodiment, the present invention provides a method for releasing risperidone at a substantially linear rate fox a period of at least 10 months into a body tissue of a subject, comprising administering to the subject a risperidone-containing implant or set of implants of the present invention, thereby releasing risperidone at a substantially linear rate for a period of at least 10 months into a body tissue of a subject.

In another embodiment, the present invention provides a method fox releasing risperidone at a substantially lineal rate for a period of at least 11 months into a body tissue of a subject, comprising administering to the subject a risperidone-containing implant or set of implants of the present invention, thereby releasing risperidone at a substantially linear rate for a period of at least 11 months into a body tissue of a subject In another embodiment, the present invention provides a method for releasing risperidone at a substantially linear rate for a period of at least 12 months into a body tissue of a subject, comprising administering to the subject a risperidone-containing implant or set of implants of the present invention, thereby releasing risperidone at a substantially linear rate for a period of at least 12 months into a body tissue of a subject.

In another embodiment, the present invention provides a method for releasing risperidone at a substantially linear rate for a period of at least 14 months into a body tissue of a subject, comprising administering to the subject a risperidone-containing implant or set of implants of the present invention, thereby releasing risperidone at a substantially linear rate for a period of at least 14 months into a body tissue of a subject In another embodiment, the present invention provides a method for releasing risperidone at a substantially linear rate for a period of at least 16 months into a body tissue of a subject, comprising administering to the subject a risperidone-containing implant or set of implants of the present invention, thereby releasing risperidone at a substantially linear rate for a period of at least 16 months into a body tissue of a subject.

In another embodiment, the present invention provides a method for releasing risperidone at a substantially linear rate for a period of at least 18 months into a body tissue of a subject, comprising administering to the subject a risperidone-containing implant or set of implants of the present invention, thereby releasing risperidone at a substantially linear rate for a period of at least 18 months into a body tissue of a subject.

In another embodiment, the present invention provides a method for treating a schizophrenia in a human, comprising administering to the human an implant or set of implants of the present invention, thereby treating a schizophrenia in a human.

In one embodiment, the schizophrenia is catatonic schizophrenia. In another embodiment, the schizophrenia is paranoid schizophrenia. In another embodiment, the schizophrenia is disorganized schizophrenia. In another embodiment, the schizophrenia is undifferentiated schizophrenia. In another embodiment, the schizophrenia is residual schizophrenia. In another embodiment, the schizophrenia is negative or deficit schizophrenia. In another embodiment, the schizophrenia is a psychosis. In another embodiment, the schizophrenia is any other type of schizophrenia known in the art. Each possibility represents a separate embodiment of the present invention.

As provided herein, methods of the present invention are effective in extended delivery of risperidone and in treatment of schizophrenia (Examples 8-9). In vivo risperidone serum concentration was within the target range of 2-15 ng/ml (Foster R H and Goa K L (1998) Pharmacoeconomics 14: 97-133) for a substantial portion of the release interval (FIGS. 1 and 3).

In another embodiment, the present invention provides a method for treating a bipolar disorder in a human, comprising administering to the human an implant or set of implants of the present invention, thereby treating a bipolar disorder in a human In another embodiment, the present invention provides a method for treating a dementia in a human, comprising administering to the human an implant or set of implants of the present invention, thereby treating a dementia in a human In another embodiment, the present invention provides a method for treating delirium in a human, comprising administering to the human an implant or set of implants of the present invention, thereby treating delirium in a human.

In another embodiment, the present invention provides a method for treating agitation in a human, comprising administering to the human an implant or set of implants of the present invention, thereby treating agitation in a human.

In another embodiment, the present invention provides a method for treating an impulse control disorder in a human, comprising administering to the human an implant or set of implants of the present invention, thereby treating an impulse control disorder in a human.

In another embodiment, the present invention provides a method for treating a psychotic depression in a human, comprising administering to the human an implant or set of implants of the present invention, thereby treating a psychotic depression in a human.

In another embodiment, the present invention provides a method for treating a schizophrenia in a human, comprising per forming one of the above methods of maintaining a therapeutic level of a drug in a subject, thereby treating a schizophrenia in a human.

In another embodiment, the present invention provides a method for treating a bipolar disorder in a human, comprising performing one of the above methods of maintaining a therapeutic level of a drug in a subject, thereby treating a bipolar disorder in a human.

In another embodiment, the present invention provides a method for treating a dementia in a human, comprising performing one of the above methods of maintaining a therapeutic level of a drug in a subject, thereby treating a dementia in a human.

In another embodiment, the present invention provides a method for treating delirium in a human, comprising performing one of the above methods of maintaining a therapeutic level of a drug in a subject, thereby treating delirium in a human.

In another embodiment, the present invention provides a method for treating agitation in a human, comprising performing one of the above methods of maintaining a therapeutic level of a drug in a subject, thereby treating agitation in a human.

In another embodiment, the present invention provides a method for treating an impulse control disorder in a human, comprising performing one of the above methods of maintaining a therapeutic level of a drug in a subject, thereby treating an impulse control disorder in a human.

In another embodiment, the present invention provides a method for treating a psychotic depression in a human, comprising performing one of the above methods of maintaining a therapeutic level of a drug in a subject, thereby treating a psychotic depression in a human.

In another embodiment, the present invention provides a use of an implant or set of implants of the present invention for the preparation of a pharmaceutical composition for treating schizophrenia. In another embodiment, the present invention provides a composition comprising an implant or set of implants of the present invention for the treatment of schizophrenia.

In another embodiment, the present invention provides a use of an implant or set of implants of the present invention for the preparation of a pharmaceutical composition for treating bipolar disorder. In another embodiment, the present invention provides a composition comprising an implant or set of implants of the present invention for the treatment of bipolar disorder.

In another embodiment, the present invention provides a use of an implant or set of implants of the present invention for the preparation of a pharmaceutical composition for treating dementia In another embodiment, the present invention provides a composition comprising an implant or set of implants of the present invention for the treatment of dementia.

In another embodiment, the present invention provides a use of an implant or set of implants of the present invention for the preparation of a pharmaceutical composition for treating delirium. In another embodiment, the present invention provides a composition comprising an implant or set of implants of the present invention for the treatment of delirium.

In another embodiment, the present invention provides a use of an implant or set of implants of the present invention for the preparation of a pharmaceutical composition for treating agitation. In another embodiment, the present invention provides a composition comprising an implant or set of implants of the present invention for the treatment of agitation.

In another embodiment, the present invention provides a use of an implant or set of implants of the present invention for the preparation of a pharmaceutical composition for treating an impulse control disorder. In another embodiment, the present invention provides a composition comprising an implant or set of implants of the present invention for the treatment of an impulse control disorder.

In another embodiment, the present invention provides a use of an implant or set of implants of the present invention for, the preparation of a pharmaceutical composition for treating psychotic depression. In another embodiment, the present invention provides a composition comprising an implant or set of implants of the present invention for the treatment of psychotic depression The period of treatment of any of the above diseases provided by a method of the present invention may be any of the time periods of the present invention. Each period represents a separate embodiment of the present invention.

"Treating," in one embodiment, refers to therapeutic intervention. In another embodiment, the term refers to prophylactic intervention. In another embodiment, the term refers to ameliorating the symptoms of a disease or disorder. In another embodiment, the term refers to ameliorating a symptoms, disease or disorder secondary to the disease or disorder being treated. In another embodiment, "treating" refers to slowing the progression of a disease. Each possibility represents a separate embodiment of the present invention.

Methods for diagnosing and assessing the severity of the above disorders are well known in the art, and are described, for example, in the Diagnostic and Statistical Manual of Mental Disorders (DSM), published by the American Psychiatric Association, Washington D.C. Each method represents a separate embodiment of the present invention. In another embodiment, schizophrenia or another of the above disorders is diagnosed by a method described above in the description of methods of assessing the efficacy of risperidone therapy Methods of assessing the efficacy of risperidone therapy in animals and humans are well known in the art. In animals efficacy of risperidone therapy may be assessed by, for example, PPI (described below) locomotor activity, rotarod, and catalepsy assessments. Locomotor activity is, in one embodiment, measured in a "home cage" activity monitoring system (MedAssociates, St. Albans, VI). This system allows for a standard, clean home cage to be placed in a photobeam frame with two levels of sensors arranged in an 8-beam array strip with 1.25 inch spacing. A computer detection system monitors interruptions of the photobeams for the ambulations parameter. Total ambulations are determined by the number of photobeam interruptions the animal makes while moving about the cage. Data are recorded on Med Associates personal computer-designed software and monitored e.g. at 5-minute intervals for a total of 30 minutes per activity monitoring session Rats typically receive several days of habituation to the apparatus and task prior to their first exposure to amphetamine.

In another embodiment, rotarod is used to assess the efficacy of risperidone therapy. In one embodiment, the accelerating rotarod treadmill apparatus (Stoelting Co., Wood Dale, Ill.) is used to determine motor function. Rats are placed on the stationary rod in order to acclimate to the apparatus. The speed is then set to gradually increase from 2 to 20 rpm. The maximal score in maintaining equilibrium and posture is fixed (e.g. 5 minutes; Lelas S, Wong H et al, J Pharmacol Exp Ther 309: 293-302, 2004). Testing ends after the period or when the animal falls off of the rod.

In another embodiment, catalepsy assessment is used to assess the efficacy of risperidone therapy. Catalepsy is tested in animals (e.g. rats) to assess motor effects from risperidone implants. Rats awe positioned with their fore legs against a cage side, and the amount of time required to resume a normal posture is recorded. Increased latency to resume normal position with all four legs on the bottom of the cage is interpreted as indicative of motor impairment secondary to risperidone.

In another embodiment, the acoustic startle response is used to assess the efficacy of risperidone therapy. The acoustic startle response is a quantifiable, reflexive movement after a loud acoustic stimulus Prepulse inhibition (PPI) occurs when the startle response is reduced because of the previous presentation of a less intense sensory stimulus (Hoffman H S, Searle J L (1965) J Comp Physiol Psychol 60:53-58) PPI can be attenuated by administration of dopamine (DA) agonists such as apomorphine (APO) and amphetamine (AMPH), and this effect is reversed by dopamine receptor antagonists such as haloperidol and risperidone (Mansbach R S, Geyer M A (1989). Neuropsychopharmacol 2: 299-308; Swerdlow N R et al, (1991). J Pharmacol Exp Ther 256: 530-536; Sweidlow N R et al, Neuropsychopharmacol 18: 50-56). As such, attenuation of PPI by DA receptor agonists is an effective animal model for the deficits in sensory-gating processes observed in schizophrenia (Braff D L, Geyer M A (1990) Arch Gen Psychiatry 47: 181-188)

Methods for recording of auditory evoked potentials are well known in the art In one embodiment, recording of auditory evoked potentials is achieved via stereotaxic implantation of tripolar electrode assemblies. In another embodiment, these assemblies are used for non-anesthetized recording of auditory evoked potentials. These methods are well known in the art and are described, e.g, in (Connolly et al, 2003; Connolly et al., 2004; Maxwell et al., 2004; Siegel et al., 2005).

An additional method for assessment of risperidone efficacy in animals is behavioral observations, which are well known in the art and are described, for example, Elmer G I, Brockington A et al (Cocaine cross-sensitization to dopamine uptake inhibitors: unique effects of GBR12909. Pharmacol Biochem Behav 53: 911-918, 1996) For example, the following behaviors are observed and scored for their presence or absence during each 5-min interval: still; sniffing; licking; gnawing; grooming; locomotion (all four, legs moving); rearing (both front feet off the cage floor); head down (animal standing, walking or running with its nose below horizontal for more than 5 seconds); swaying (rhythmic swaying movements of the animal's head or body for more than 3 seconds); circling (walking or running in a continuous circle for more than 5 seconds).

In another embodiment, the efficacy of risperidone therapy is assessed by quantification of dopamine $D_2$ and/or serotonin $5HT_{1A/2A/2C}$ receptor expression in brain samples (e.g. cortex, hippocampus, striatum and/or cerebellum). Risperidone increases dopamine $D_2$ receptor expression and decreases serotonin $5HT_{1A/2A/2C}$ receptor expression. Serotonin receptor Western blots can utilize polyclonal antibodies AB5406 (Chemicon, Temecula, Calif.), PC176L (Calbiochem, Calif.), or and AB5655 (Chemicon). $D_2$ receptor Western blots can utilize polyclonal antibody WR-3526, (Research and Diagnostic Antibodies, Berkeley, Calif.). Each possibility represents a separate embodiment of the present invention.

Methods of assessing the efficacy of risperidone therapy in humans are described, e g, in Heresco-Levy U et al (Biol Psychiatry 2005 57(6): 577-85), Moller H J et al (Int Clin Psychopharmacol. 2005 20(3): 121-30); and Hirschfeld R M et al (Am J Psychiatry. 2004 161(6): 1057-65). In another embodiment, the efficacy of risperidone therapy in humans by assessing the severity of the disorder for which risperidone was described, using the DSM-IV. Each of the above methods for assessing efficacy of risperidone therapy in animals may be utilized for humans and vice-versa.

Each of the above methods for assessment of risperidone efficacy represents a separate embodiment of the present invention.

In another embodiment, the present invention provides an implant having a drug load of a therapeutic drug between about 20-30% by mass, inclusive, and between 70%-80% by mass, inclusive, of a polymer, the polymer comprising PLA and optionally PGA in a PLA:PGA ratio between 80:20 and 100:0 by mass, inclusive, the implant having a radius of $R_0$ according to the equation:

$$\left(\frac{dM_d}{dt}\right) = :4\pi R_0^2\left(1-\frac{C_w\sqrt{D}}{2R_0\sqrt{k}}l\right)^2\frac{C_w\sqrt{D}\,erf\left[\sqrt{kt}\right]}{2\sqrt{k}}$$

wherein: "$erf(x)$" refers to $\frac{2}{\sqrt{\pi}}\int_0^x e^{-t2}\,dt$;

$dM_d/dt$ is the desired steady-state release rate of therapeutic drug at time t, D is the diffusion coefficient of water into the matrix, k is the reaction rate and $C_w$ is the concentration of water in the implant at time t;

wherein k is determined by the formula:

$$\frac{\partial c_w}{\partial t} = D\nabla^2 c_w - kc_w$$

wherein S is the solubility of therapeutic drug in water; and wherein k is a constant between about 0.05-0.33.

In one embodiment, the therapeutic drug contained in the above implant is risperidone. In another embodiment, the therapeutic drug is haloperidol, in which case D is 1.7×10^-10, and k is 0.07 (Example 10). In another embodiment, the therapeutic drug is thiothixene, in which case D is 9×10^-10, and k is 0.06 In another embodiment, the therapeutic drug is HCTZ, in which case D is 2-1×10^-6, and k is 0.26. In another embodiment, the therapeutic drug is corticosterone, in which case D is 2.5×10^-7, and k is 0.33. In another embodiment, the therapeutic drug is ibuprofen, in which case D is 7.0×10^-6, and k is 016. In another embodiment, the therapeutic drug is aspirin, in which case D is 8.0×10^-2, and k is 0.06. In another embodiment, the therapeutic drug is any other therapeutic drug known in the art. Each possibility represents a separate embodiment of the present invention.

In another embodiment, k, the degradation reaction rate coefficient, depends on the drug properties as given by a combination of the drug solubility and the presence of OH groups (Example 11). For drugs with the same water solubility, the rate of polymer hydrolysis increases with the density of OH groups, while for drugs with the same OH group density k decreases with solubility in another embodiment, k is empirically determined, as described in Example 10.

In another embodiment, the presence of the drug affects the polymer degradation rate. In one embodiment, the drug affects the polymer degradation rate by affecting the diffusion of water into the polymeric matrix. In another embodiment, the drug affects the polymer degradation rate by affecting the rate of the degradation reaction. In another embodiment, the drug affects the polymer degradation rate by a combination of the above mechanisms Each possibility represents a separate embodiment of the present invention.

In another embodiment, the present invention provides a method of designing an implant to deliver a target late of release of a therapeutic drug, by utilizing an equation of the present invention (e.g. equation 4, 5a, or 5b).

In another embodiment, the present invention provides a method of designing an implant to achieve a target rate serum concentration of a therapeutic drug, by utilizing an equation of the present invention (e.g. equation 8, 9, or 10; Example 12).

In another embodiment, the present invention provides a method of achieving a drug release rate $dM_d/dt$ at time t, comprising administering an implant whose radius has been determined using an equation of the present invention (e.g. equation 4, 5a, or 5b).

In another embodiment, the present invention provides a method of achieving a serum concentration x at time t, comprising administering an implant whose radius has been determined using an equation of the present invention (e.g. equation 8, 9, or 10).

Any of the methods of the present invention may utilize any of the implants of the present invention. Each combination of a method of the present invention with an implant of the present invention represents a separate embodiment of the present invention.

In another embodiment, the present invention provides a kit comprising a reagent utilized in performing a method of the present invention. In another embodiment, the present invention provides a kit comprising an implant of the present invention.

EXPERIMENTAL DETAILS SECTION

Example 1

Extended Haloperidol Release from PLGA Implants in Monkeys

Materials and Experimental Methods

Subjects

Two monkeys (Macaca fascicularis, Rangos Research Facility) were utilized, each of which received 6 copolymer PLGA (poly(d,l-lactic-glycolic acid))-containing implants. For the experimental monkey, the implants contained 40% haloperidol by mass, with the other 60% consisting of one of the PLGA polymers depicted in Table 1 below. The implants administered to the control monkey contained 100% of the PLGA polymers depicted in Table 1. PLGA polymers were provided by Medisorb® Alkermes, (Cincinnati, Ohio). Haloperidol dosing averaged 1 mg/kg/day over 12 months to achieve a serum concentration of 2-10 ng/ml.

Table 1. Polylactic acid:polyglycolic acid (PLA:PGA) molar ratios and inherent viscosities of the PLGA polymers in the implants used in the primate experiment Inherent viscosities in the table are expressed in units of dl/g in chloroform, and were measured at 30° C., 0.5 dl/g using a size 25 Cannon-Fenske glass capillary viscometer.

| Implant number | PLA:PGA molar ratio | Inherent viscosity (IV) |
|---|---|---|
| 1 | 75:25 | 0.66-0.80 |
| 2 | 85:15 | 0.66-0.80 |

-continued

| Implant number | PLA:PGA molar ratio | Inherent viscosity (IV) |
|---|---|---|
| 3 | 90:10 | High (0.87) |
| 4 | 90:10 | Low (0.68) |
| 5 | 95:5 | 0.66-0.80 |
| 6 | 100:0 | 0.66-0.80 |

Implant Manufacture

Polymers and haloperidol (Sigma, St. Louis, Mo.) were mixed in a proportion of 60/40 by mass and solvent cast from acetone (Fisher Scientific, Pittsburgh, Pa.). The resulting film was compression molded to disk-shaped implants of 20 mm diameter with average thickness of 1.22±0.0 mm, mass 493±2 mg and density of 1.28±0.0 g/cc Pharmacokinetic Determination:

Blood was drawn twice per month. Blood was centrifuged and serum frozen at −80° C. until analysis. Serum risperidone and 9-OH risperidone concentrations were determined in duplicate at each time point for each animal. Specimens were separated by centrifugation and haloperidol levels were assayed by high-pressure liquid chromatography (HPLC) with ultraviolet (UV) detection (FIG. 1). Assays from control animals yielded drug levels of zero.

Results

As depicted in FIG. 1, haloperidol release was measured over a total of 443 days. Mean serum concentration was 10.5±1.5 ng/ml during the first 224 days, with the exception of one value (27.1 ng/ml on day 40). During the subsequent 176 days, serum haloperidol levels were sustained at a lower mean concentration of 4.0±0.4 ng/ml. Levels decreased during the last 45 days of the study (mean serum concentration 1.2±0.3 ng/ml).

Thus, 14 months of haloperidol release was achieved in monkeys using biodegradable implants.

Example 2

Extended Haloperidol Release from PLGA Implants in Rabbits

Materials and Experimental Methods

Experimental Design

Two implant systems were tested, the first containing five different single-polymer implants (similar to Example 1), and the second containing five implants comprised of a single polymer. The aim of the single-polymer model was to reduce the initial spike while maintaining release for one year Subjects Rabbits (N=12, Covance, Denver, Pa.) ranged from 4.0 to 5.7 kg. Five animals received implants composed of a single polymer, 100% PLA, with 40% haloperidol load for a total drug content of 418±7 mg/kg, yielding a daily dose of 1.13±0.02 mg/kg/day for anticipated delivery of 365 days Five additional animals received implants of a combined-polymer system including 75:25, 85:15, 90:10 high IV, 90:10 low IV and 100:0 PLGA. The mean dose in this group was 473±4 mg/kg with an expected delivery of 365 days, yielding a mean dose of 1.29±0.03 mg/kg/day. Two rabbits received implants without drug as a control. One control received 100% PLA implants to mimic the single-polymer condition, the other received implants composed of 75:25, 85:15, 90:10 high IV, 90:10 low IV & 100:0 PLGA to mirror the combined-polymer system.

Implant Manufacture

Implants were made using procedures described in Example 1, in this case with an average mass of 536±2 mg and density of 1.24±0.00 g/cc. Implants were tethered to assist in locating implant sites at necropsy.

Pharmacokinetic Determination

Solid phase extraction (SPE) was performed using the Waters 20-postion SPE vacuum manifold and Waters Oasis MCX SPE cartridges, (3 ml/60 μg cartridges). Cartridges were conditioned with methanol and water, samples containmg 2% phosphoric acid were loaded, then cartridges were washed with 5% methanol in 0.1 N hydrochloric acid, then 100% acetonitrile, then eluted with 5% $NH_4OH$ in 100% acetonitrile. Samples were dried under nitrogen in an 80° C. water bath, reconstituted in 100 μl of mobile phase, vortexed, and centrifuged for 5 minutes. 75 μl of the reconstituted samples were loaded into an autosampler and 50 μl was injected. HPLC was performed using a Waters XTerra RP 18 5 um, 4.6×150 mm column, flow rate 1.0 ml/min, run time 30 min. Mobile phase and sample buffer were composed of 55% $H_2O$ with 35% acetonitrile and 10% 100 mM ammonium bicarbonate, pH 10. Peaks were detected at a wavelength of 280 nm. Standard solutions of risperidone and 9-OH risperidone were prepared in normal rat serum (range 1.25-50 ng/ml), extracted, and included within each run to provide the standard curve and retention time for each compound. The retention times for risperidone and 9-OH risperidone, were 8.6 and 5.9 min, respectively.

Histopathology

Figure 2:
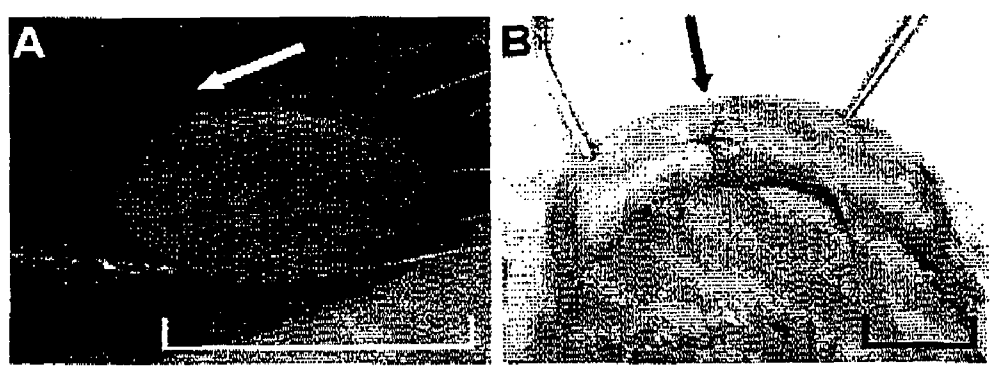
FIG. 2 A) Placement of implants during rabbit surgery. A tethered implant (white arrow) is shown. The incision was enlarged to enable a photograph. B) Necropsy in rabbits showing a degraded implant (black arrow) at the tethering location between two hemostats. No fibrosis was observed upon implant removal. Scale bar=20 mm in both images FIG. 3 Haloperidol serum concentration from polymer implants in rabbit Each panel displays the mean±SEM for 5 animals. A) Multiple-polymer system. B) Single-polymer system. Each set of data is shown with a trendline to illustrate the pattern of the serum concentration over time.

Five rabbits were sacrificed after nine months to obtain interim pathological analyses, with remaining seven rabbits sacrificed after an additional four months. Remains of implants were found tethered in place in all animals that received implants (FIG. 2). Implants did not cause capsule formation, leading to a simple removal process. HPLC/UV and NMR spectroscopy confirmed the presence of haloperidol and PLGA breakdown products in residual implants. Histological analyses showed all organ systems in all rabbits were within normal limits.

Results

A similar experiment was performed in rabbits, in this case comparing five different single-polymer implants (similar to Example 1) with five implants comprised of a single polymer. Rabbits administered the multiple-polymer system had haloperidol levels of 4.0±0.6 ng/ml over 360 days. An initial period of higher concentration occurred during the first 198 days (mean serum level of 6.1±0.7 ng/ml) (FIG. 3A). Levels then tapered to a mean of 1.1±0.3 ng/ml through 320 days, dropping below the level of detection at 360 days. B) Rabbits administered the single-polymer system exhibited a more symmetric release profile and had a mean serum concentration of 2.5±0.4 ng/ml, dropping below the level of detection at 360 days, as observed for the multiple-polymer system (FIG. 3B).

Thus, the findings obtained with rabbits confirmed the monkey findings, showing that 12 months of haloperidol release can be achieved using biodegradable implants. These results also show that at least in some cases, a more symmetric release profile can be achieved with a single-polymer system than with a multiple-polymer system.

Example 3

Effect of Implant Geometry on Release Rate

Materials and Experimental Methods

Implants containing 40% Haloperidol and 60% of a 50:50 PLGA polymer were manufactured by solvent casting. Material was compression molded into discs or slowly extruded into rods using a high pressure piston extruder (DACA Instruments, Goleta, Calif.) at 100° C. Rods & discs were matched for weight. The surface area to volume (SA:V) ratios for these geometries are 1.92 for discs (3 mm radius, 1.6 mm thickness) and 1.56 for rods (1.8 mm radius, 4.5 mm length).

To measure release profiles, implants were placed in 500 milliliter (ml) phosphate buffered saline (PBS), pH 7.0, 37° C., 40 rpm, in the dark.

Results

Figure 4:
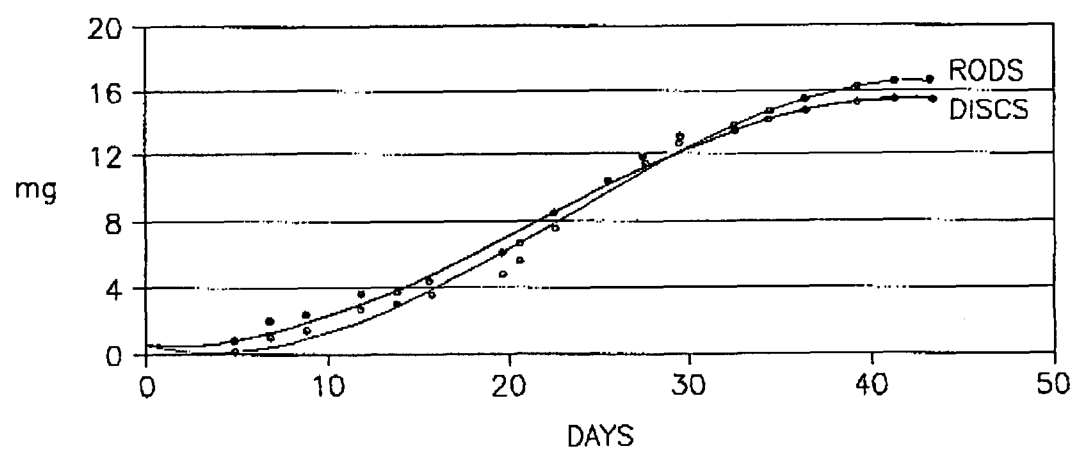
FIG. 4: Cumulative in vitro concentration from disc & rod-shaped implants. Each point represents the mean for 3 replicates of discs or rods.

The effect of implant geometry (rods vs. disks) on haloperidol release was examined. Release profiles were nearly identical for both geometries (FIG. 4), demonstrating that rods have very similar release profiles to disks. Thus, rods-shaped implants can be used to deliver maintain therapeutic levels of a drugs in a subject over an extended period of time.

Example 4

Stability of Risperidone in Physiological Aqueous Solution

Figure 5A:
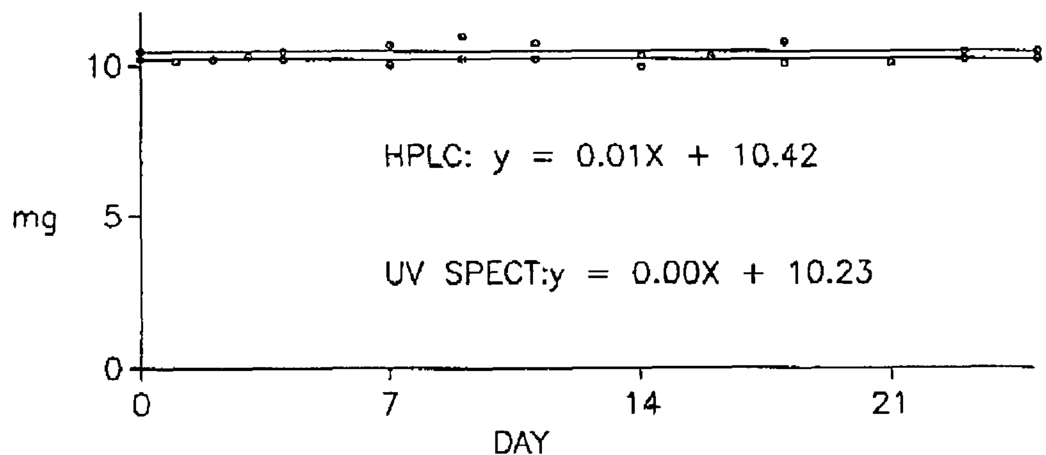
FIG. 5. Stability of risperidone in physiological aqueous solution A. Amount of remaining risperidone vs. time. The y-intercept is 10.42 for HPLC and 10.23 mg for UV spectrophotometry. Similarly, the slope of the linear trendline for HPLC is 0.01 and 0.00 for UV spectrophotometry. B) Values for the positive control solution in A, as well as samples in the surface area to volume ratio study (FIG. 6B) were analyzed and compared using HPLC and UV spectrophotometry. The correlation coefficient for these methods is 0.99 (182 samples), showing that UV spectrophotometry is an accurate measure of drug level in an in vitro solution.
Figure 5B:
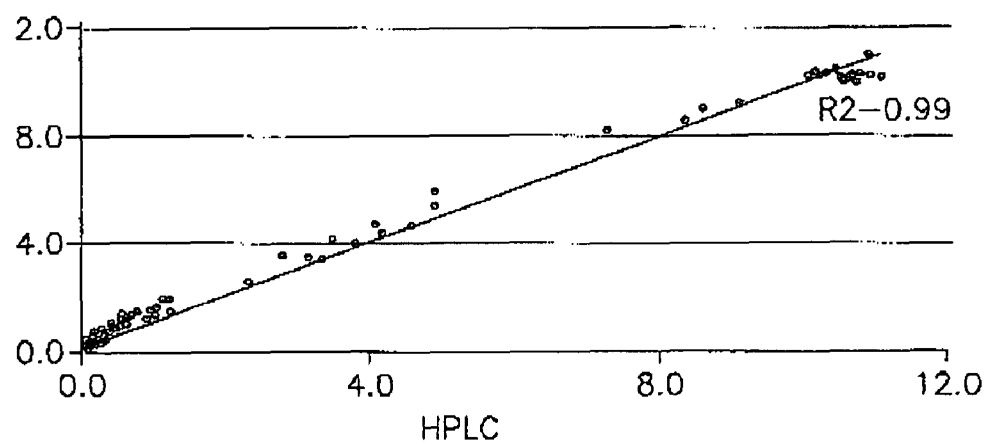

To evaluate the long-term stability of risperidone in physiological solution, 10 mg Risperidone was dissolved in 100 μl of acetonitrile for subsequent dissolution in 1,000 ml of PBS (0.9% NaCl, 0.01 M NaOH, 0.01 M $NaH_2PO_4$, pH 7.0) to yield a final solution of 10,000 nanograms (ng)/ml. The solution was shaken at 40 revolutions per minute in a light-safe amber bottle at 37° C. Drug concentration of a 1-ml sample was measured three times per week by UV spectroscopy (Amersham Biosciences, Buckinghamshire, UK). The concentration of drug exhibited only a slight change (1.4% over 343 days, equivalent to 0.004% per day; linear trendline: y=−0.0004x+9.777). Studies were replicated using UV spectrophotometry and HPLC (FIG. 5). There was a 0.99 correlation coefficient between HPLC and UV spectrophotometry, indicating that the UV spectrophotometry method is an accurate method for in vitro analysis of risperidone concentration.

Thus,risperidone is stable over extended time periods in Physiological solution.

Example 5

Effect of PLA:PGA Ratio on Risperidone Release

Figure 6A:
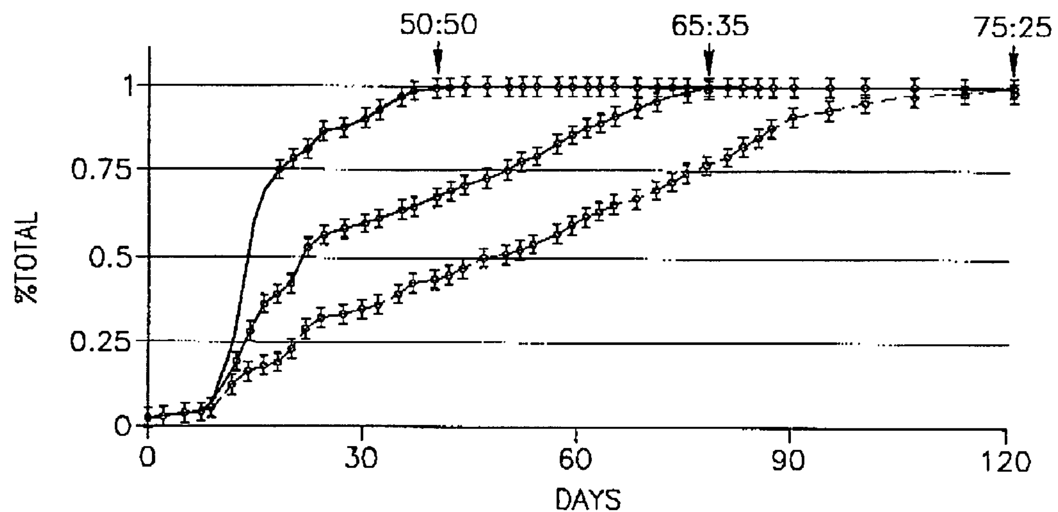
FIG. 6 In vitro risperidone release varies with polymer composition and SA:V ratio: A) Polymer composition—Cumulative in vitro risperidone release from 20% load implants containing 50:50, 65:35, or 75:25 PLGA Data are expressed as cumulative % total release over time. Each point represents the mean±standard error of the mean (SEM) of 3 implants. Full release occurred at about 40, 80 & 120 days, respectively. B) SA to volume ratio—Rods with the smaller radius, and hence larger SA:V ratio (circles) exhibited faster in vitro release than rods with larger radius (triangles), as evidenced by higher cumulative concentration between 28 and 44 days. Points represent mean±SEM from 4 rods. Data were analyzed with HPLC and UV spectrophotometry, which produced identical results, as in FIG. 5.

Risperidone release from different polymers including 50:50, 65:35 and 75:25 PLGA was evaluated to assess the effects of PLA:PGA ratio on in vitro risperidone release. Implants were made as described for Example 1, in this case with 20% risperidone (RBI, Flanders, N.J) and 80% PLGA (Alkermes). Three replicates of each implant type were placed in separate light-safe bottles of 500 ml PBS and shaken at 37° C., 40 rpm). 1 ml aliquots were taken from each bottle 3 times per week and analyzed by UV spectrophotometry, after which 1 ml of buffer was reintroduced to maintain constant volume. The 75:25 polymer exhibited the slowest release profile (FIG. 6A).

Example 6

Effect of Surface Area to Volume Ratio on Risperidone Release

Materials and Experimental Methods

Studies utilized 4 rods per condition with surface area to volume (SA:V) ratios of 2.75 and 6.17, both utilizing a 30% risperidone drug load, 75:25% PLGA. Rods were placed in separate bottles of PBS at 37° C. at 40 rpm. 0.3 ml samples were drawn 3 times per week analyzed by HPLC and UV spectrophotometry (Bio-teck Instruments, Winooski, Vt.).

Results

Figure 6B:
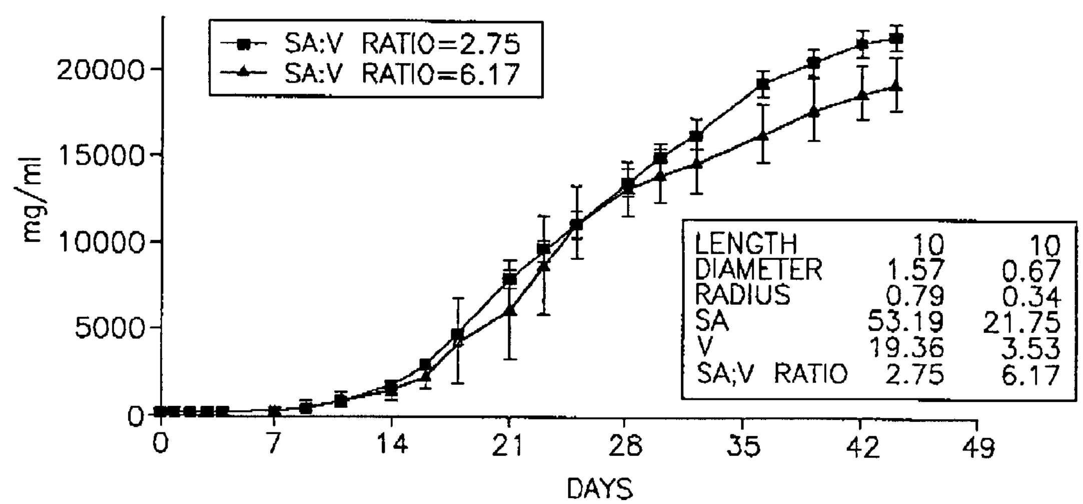
Figure 7A:
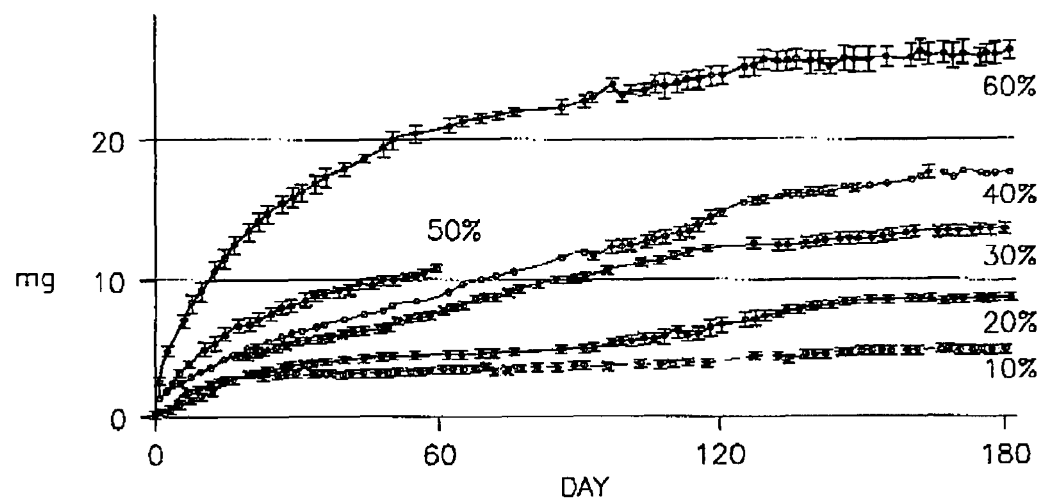
FIG. 7. In vitro cumulative risperidone release from implants containing 85:15 PLGA with 10, 20, 30, 40, 50 or 60% drug load by weight. A) Cumulative mass of risperidone in the in vitro solution (mean±SEM). B) The pattern for the 40% risperidone implants is shown alone for clarity. The trendline, which has a correlation coefficient of 0.99, is included to illustrate the pattern C) Cumulative mass released from 30, 40, 50, and 60% risperidone implants is expressed as a percentage of the total drug to facilitate comparison of the pattern of release as a function of drug load The mean value for each type of implant is also depicted. Trendlines for each of these 4 implants had correlation coefficients $R^2$) of 0.99. 10% and 20% curves were omitted to increase visibility of overlapping lines. D) The 40% drug load group is shown alone for increased clarity.
Figure 7B:
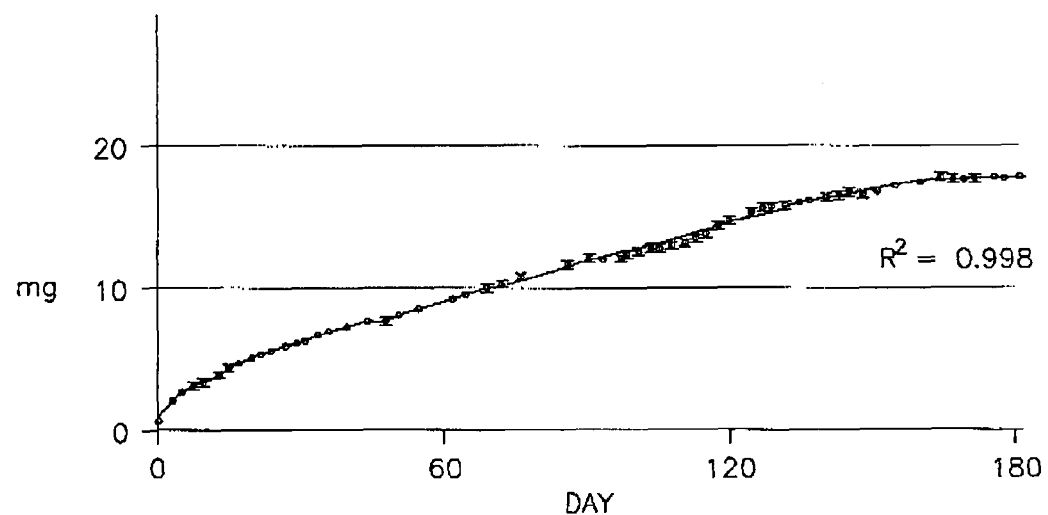
Figure 7C:
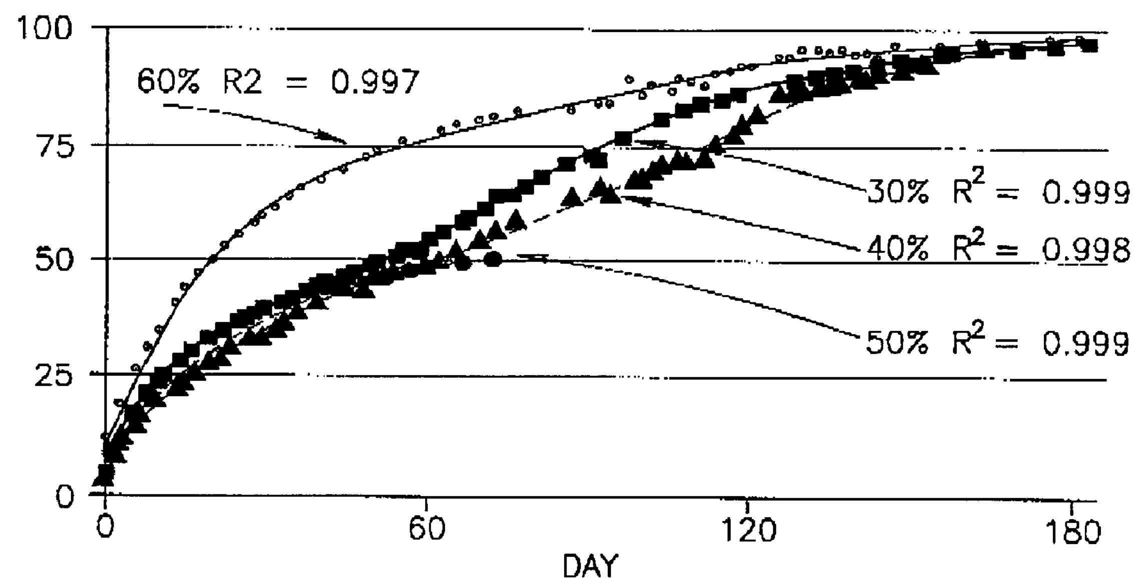
Figure 7D:
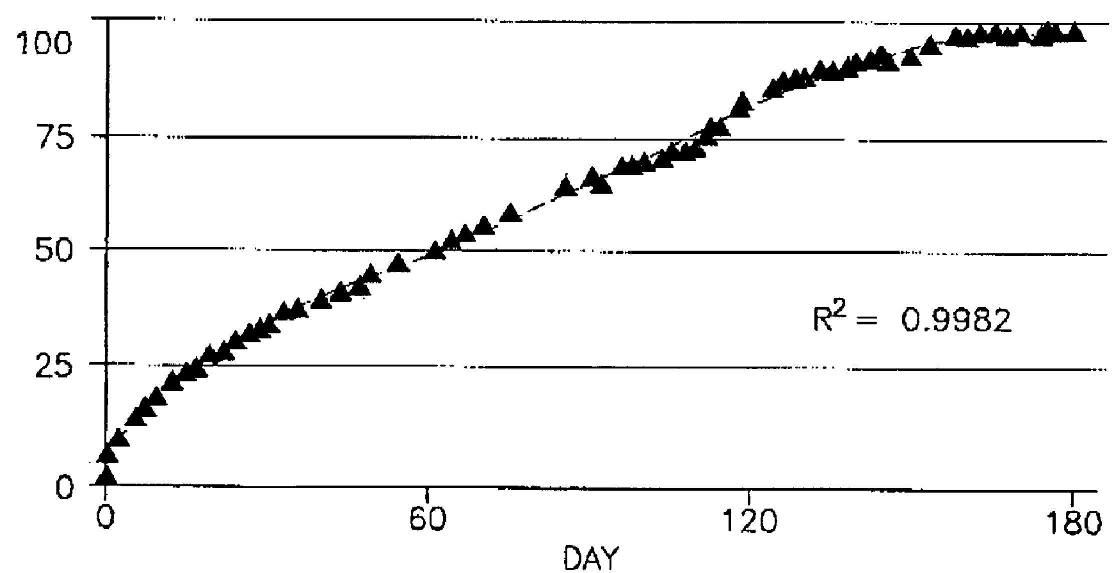

To determine the effect of SA:V ratio on risperidone release, risperidone release was measured from rods with identical composition but different SA:V ratios. The pattern of release among these 2 SA:V ratios differed dining the first 44 days of release with the smaller radius rods (larger SA:V) exhibiting more rapid release (FIG. 6B). Thus, larger diameter rods, which have a smaller SA:V ratio, provide more extended delivery than smaller diameter rods.

These results confirm and augment the results of Example 3 by demonstrating that release from biodegradable implants is a function of SA:V ratio, as described further below in equation (8). Thus, rods as well as disks can be used to achieve extended release of drugs in biodegradable implants.

Example 7

Determination of Optimal Risperidone Drug Load in Implants

To determine the optimal risperidone concentration for implants, implants were prepared using a single polymer (85:15 PLGA) combined with risperidone at ratios of 10%, 20%, 30%, 40%, 50% or 60% drug by weight (FIG. 7). Implants each had a mass of approximately 50 mg, and thus contained drug masses of 5, 10, 15, 20, 25 and 30 mg, respectively. A large fraction of the total drug load of the 10% and 60% drug-loaded implants was released within the first 30 days, while the 20%, 30%, 40%, and 50% drug-1-0 release their risperidone more slowly. The most linear pattern of release was achieved with the 40% and 50% risperidone-loaded implants, with similar slopes throughout the entire time tested.

Example 8

Risperidone Implants Increase PPI and P20 Amplitude and Block Amphetamine-Induced Disruption of N40-Evoked Potentials at 14 and 21 Days Post-Implantation Materials and Experimental Methods Risperidone implants yielded serum risperidone concentration of 7.3±0.68 ng/ml (mean±SEM) and serum 9-OH risperidone of 8.1±0.95 ng/ml at 42 days after implantation. Brain levels were 6.2±1.45 & 4.6±0.52 ng/gm for risperidone & 9-OH risperidone respectively. Disc shaped implants (SA:V ratio of 2.34) were made from 85:15 PLGA, 0.66-0.80 IV, with 20% risperidone drug load. Mice (C57BL/6J) received either implants containing risperidone (n=8) or polymer alone (n=8) prior to stereotaxic implantation of tripolar electrode assemblies (PlastiesOne Inc., Roanoke, Va.) for non-anesthetized recording of auditory evoked potentials (Connolly et al, 2003; Connolly et al 2004; Maxwell et al., 2004; Siegel et al., 2005). Studies on startle and prepulse inhibition (PPI) of the acoustic startle response were performed between 14 and 21 days after implantation as described in (Gould T J et al, Sensorimotor gating deficits in transgenic mice expressing a constitutively active form of Gs alpha. Neuropsychopharmacol 29: 494-501). Recording of evoked potentials was performed 28 days after implantation of electrodes. Recording for the drug exposure trial began six minutes after injection of amphetamine 2 mg/kg i.p. and was compared to the pre-amphetamine recording session. Stimuli were generated by Micio1401 hardware and Spike 5 software (CED, Cambridge, England) and were delivered through speakers attached to the cage top. A series of 50 white noise clicks (10 ms duration) were presented in pairs 500 ms apart with a 9 second inter-pair interval at 85 db compared to background of 70 db. Waveforms were filtered between 1 and 500 Hz, baseline corrected at stimulus onset and individual sweeps were rejected for movement artifact based on a criteria of two times the root mean squared amplitude. Average waves were created from 50 ms pre-stimulus to 200 ms post stimulus. Mice were allowed fifteen minutes to acclimate to the Faraday cage prior to stimulus onset.

Results

Figure 8A:
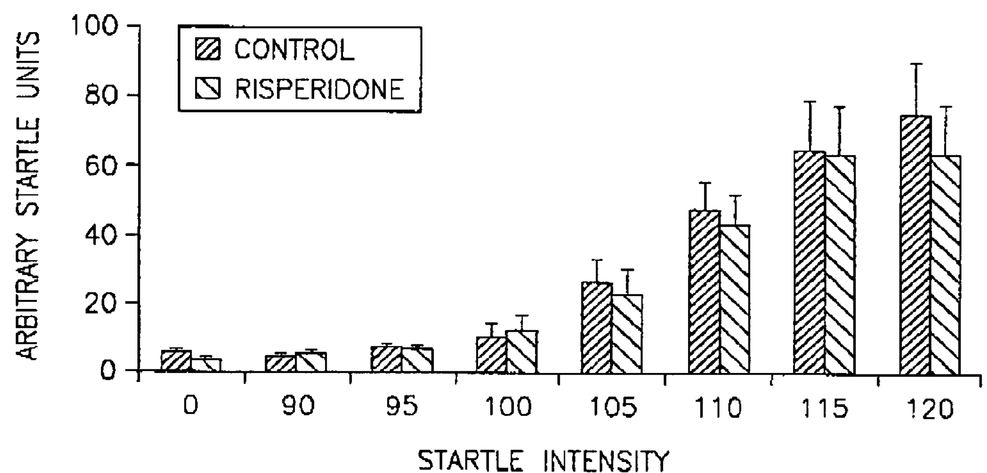
FIG. 8. Risperidone implants increase PPI but not startle. Risperidone implants increased PPI (B; p=0.052) without a significant change in startle (A) at 14 and 21 days post implantation.
Figure 8B:
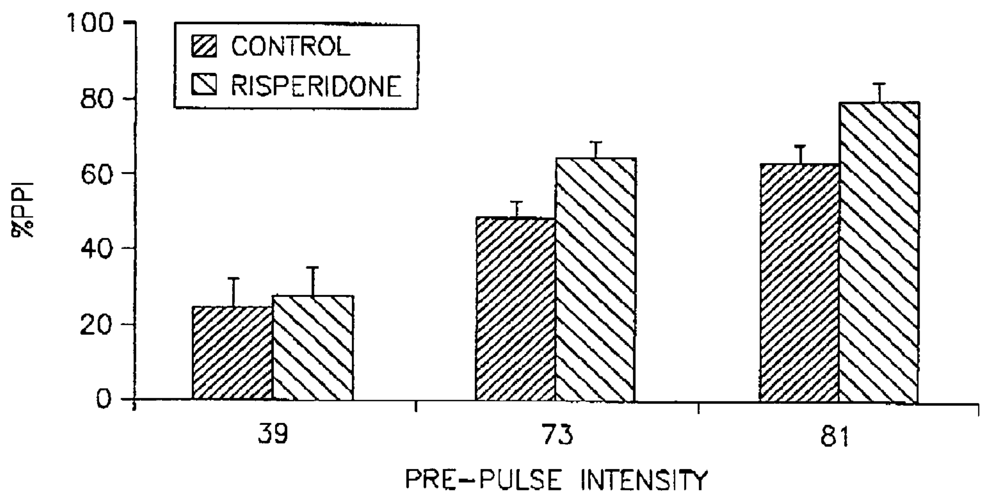
Figure 9A:
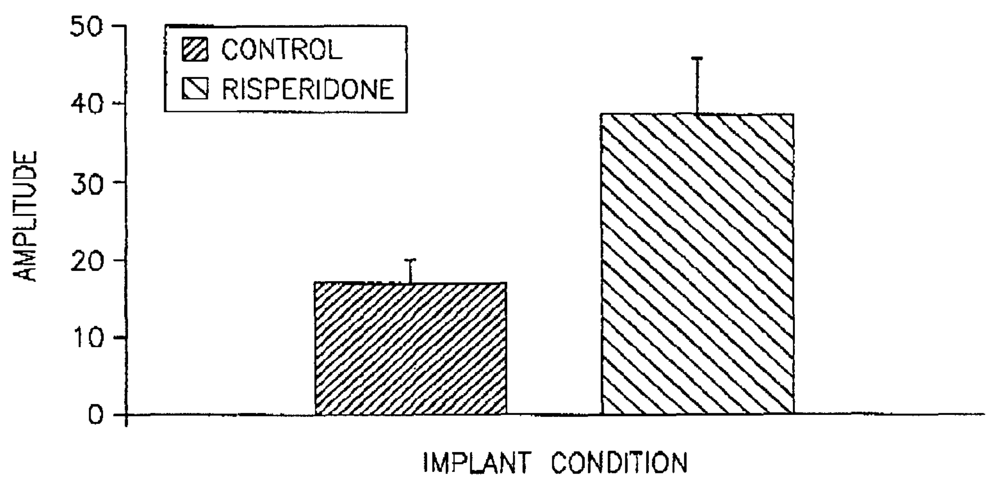
FIG. 9. Risperidone implants increase the P20 and block amphetamine-induced disruption of the N40 evoked potentials. A) Risperidone implants increased P20 amplitude in C57BL/6J mice (p=0.03) and (B) attenuated amphetamine reduction of N40 (p=0.02).
Figure 9B:
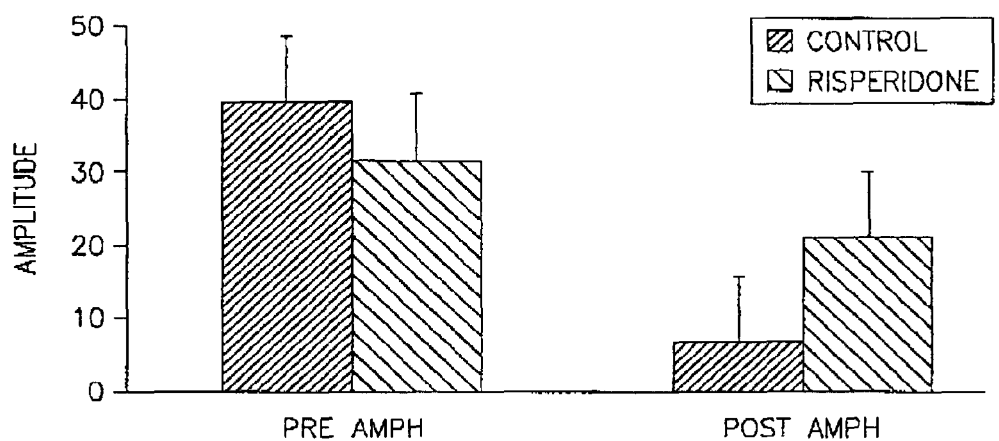

Mice (C57BL/6J) received either implants containing risperidone (n=8) or polymer alone, then were subjected to non-anesthetized recording of auditory evoked using implanted tripolar electrode assemblies. While risperidone implants did not alter startle amplitude (FIG. 8A), they did increase PPI relative to controls (FIG. 8B). In addition, risperidone implants increased the amplitude of P20 (the human P50 analogue) in control animals (FIG. 9A), and attenuated amphetamine-induced reduction of the amplitude of N40 (the human N100 analogue) (FIG. 9B). Abnormalities in the P50 and N100 components reflect abnormal neuronal architecture related to the generation and modulation of auditory responses and are informative about more generalized neurological impairments in schizophrenia (Adlei L E, Olincy A et al, Schizophr Bull 24: 189-202, 1998; Freedman R, Adlei L E et al, Harv Rev Psychiatry 2: 1.79-192, 1994).

Example 9

Risperidone Implants Increase PPI and P20 Amplitude and Block Amphetamine-Induced Disruption of N40-Evoked Potentials at Later Post-Implantation Time Points Experiments are performed to determine the effect of the risperidone implants of Example 8 on startle, PP1, P20, and N40, at later time points after implantation. In this case, significant effects are observed for all these parameters in animals receiving the risperidone implants, consistent with the larger release rate and subsequently higher plasma concentration attained at later time points, as shown in Examples 5-7.

Example 10

Release Rate from Hydrolysable Bio-Degradable Implants can be Determined Based on Drug Solubility and the Rate of Degradation of the Implant Materials and Experimental Methods Drugs Six drugs were examined:

1). Thiothixene: N,N-dimethyl-9-[3-(4-methylpiperazin-1-yl)propylidene]thioxanthene-2-sulfonamid, 2). Haloperidol: 4-[4-(4-chlorophenyl)-4-hydroxy-1-piperidyl]-1-(4-fluorophenyl)-butan-1-one.

3). Hydrochlorothiazide (HCTZ): 9-chloro-5,5-dioxo-5$\lambda^6$-thia-2,4-diazabicyclo[4.4.0]deca-6,8,10-thiene-8-sulfonamide.

4). Corticosterone: 11-hydroxy-17-(2-hydroxyacetyl)-10,13-dimethyl-1,2,6,7,8,9,10,11,12, 13,14,15,16,1,7-tetradecahydrocyclopenta[a]phenanthren-3-one.

5). Ibuprofen: 2-[4-(2-methylpropyl)phenyl]propanoic acid.

6) Aspirin: 2-acetyloxybenzoic acid

Properties of the drugs are listed in Table 2. All drugs were obtained from Sigma-Aldrich, Inc.

Table 2. Properties of drugs utilized in this Example.

| Drug | Molecular formula | Molecular weight | Water solubility (mg/mL)* | D** | k** | OH group density (OH groups/ unit mass) |
|---|---|---|---|---|---|---|
| Haloperidol | $C_{21}H_{23}ClFNO_2$ | 375.87 | 0.13 | $1.7 * 10^{-10}$ | 0.07 | $2.66 * 10^{-3}$ |
| Thiothixene | $C_{23}H_{29}N_3O_2S_2$ | 443.64 | 0.14 | $9 * 10^{-10}$ | 0.06 | 0 |
| HCTZ | $C_7H_8ClN_3O_4S_2$ | 297.75 | 2.00 | $2.1 * 10^{-6}$ | 0.26 | 0 |
| Corticosterone | $C_{21}H_{30}O_4$ | 346.47 | 0.50 | $2.5 * 10^{-7}$ | 0.33 | $5.77 * 10^{-3}$ |
| Ibuprofen | $C_{13}H_{18}O_2$ | 206.29 | 0.47 | $7 * 10^{-6}$ | 0.16 | $4.85 * 10^{-3}$ |
| Aspirin | $C_9H_8O_4$ | 180.16 | 4.99 | $8 * 10^{-2}$ | 0.06 | $5.55 * 10^{-3}$ |

*Measured after 14 days as described below.

**k is units of 1/day, and D dimensionless. Obtained by fitting the data plotted in FIG. 10 to equation (4), as demonstrated in FIG. 11.

Ultraviolet (UV) Scanning

Drugs were dissolved in PBS, pH 7.4, to the expected in vitro solubility. Absorbance scans were performed on drug solutions within the range of 200 nm to 400 n, using a blank cuvette containing saline solution as a reference. A characteristic UV footprint was generated for each drug, and the wavelength at which the relevant maximum peak occurred was utilized in subsequent in vitro assays. Standard curves were prepared for each drug in PBS so that absorbencies could be converted to concentrations using the Lambert-Bear law.

Polymer/Drug Pellet Fabrication 400 mg of 50:50 PLGA and 100 mg of drug were solvent cast to obtain a 20% by mass drug-load. Polymer and drug were dissolved in 45 milliliters (mL) acetone (Fisher Scientific, Inc.) and vortexed, then poured into an evaporation dish and placed in a vacuum oven at 40° C. under vacuum (3 inches Hg) with trace airflow. After seven days, dishes were removed from the oven. Evaporation residue was a thin film mixture of polymer and drug with homogenous appearance. The film was carefully weighed to confirm complete removal of solvent and pressed into four uniform disk-shaped pellets with 1 mm thickness and 1.2 mm diameter, using a Teflon®-coated pellet press set at 25 (kilo-pounds) klb and 60° C. Pellets were carefully weighed and measured to determine densities. Negative control pellets with a 0% drug load were fabricated in the same manner; using 500 mg polymer and no drug.

Drug Solubility in Water

Ascending mass of drug, ranging from 0.5 to 200 mg, of each drug was mixed into a capped glass jar (Wheaton, Inc.) containing 10 to 50 mL distilled water and subjected to moderate mixing for 14 days at 21° C. 1-mL aliquots were removed at fixed time intervals and analyzed by UV Spectroscopy to determine maximum saturation concentration.

In Vitro Drug Release Assay

Assays were performed in triplicate using three of each set of four uniform pellets. Each pellet was added to an amber-glass, capped jar (Wheaton, Inc.) containing 500 mL of a PBS solution and subjected to moderate shaking in the dark, at 37° C. 1-mL aliquots of were analyzed by UV Spectroscopy at fixed time intervals and. Positive control jars contained PBS and 10 mg of drug, the expected maximum release for a 20% drug-loaded pellet with a mass of 50 mg, and were also used to determine stability of each chug in saline solution over the course of the experiment.

Results

Figure 10:
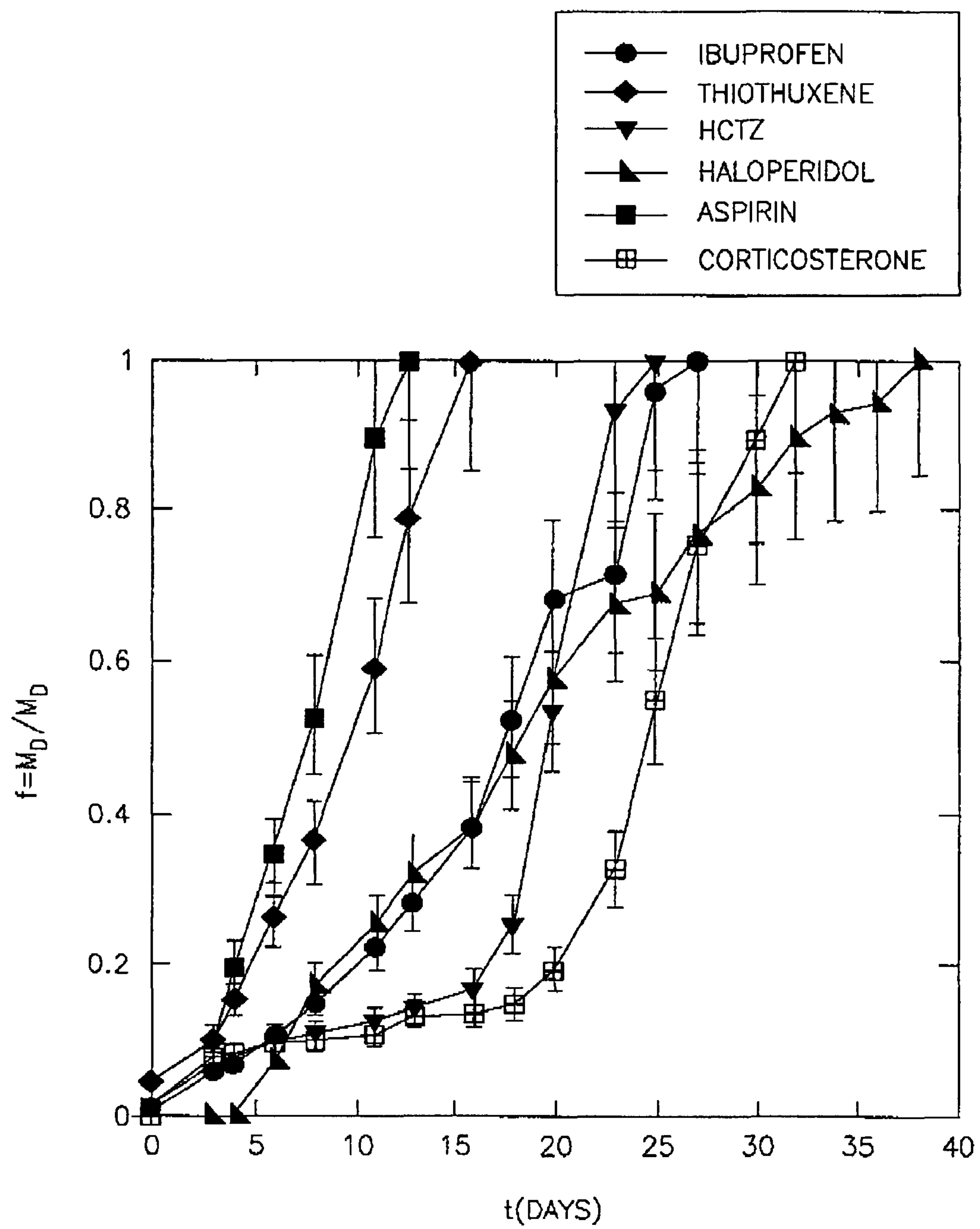
FIG. 10. Amount of drug released (normalized to the total amount) as a function of time for different drugs. Although all release profiles follow a similar S shape, the rates were quite different, both in the region of initial release, the slope of the constant release zone (where $\Delta f/\Delta t$ is constant) and the characteristic time for Cull release (f=1).

Release of six drugs from PLGA matrices was examined. f, the fraction of the drug released from the pellet, is plotted in FIG. 10 as a function of time t. At long time periods all drug was released and f≈1. Preceding this full release limit was a region wherein the release rate was fairly constant, as evidenced by a linear relationship between the fraction of released drug (Δf) and the time (Δt).

These results show that linear chug release can be obtained with a single type of biodegradable polymer Two additional features emerge from the above drug-release measurement: First, some drugs (e.g. thiothixene) were released as soon as the experiment begins, while others (e.g. haloperidol) exhibited an induction time, during which no measurable amount of drug was released. In addition, during steady state release (constant ?/? t), different drugs exhibited different release rates. As a result, variation was observed in both the rate of steady state release and the overall period of time over which the drug is released. Visual observations confirmed that pellets containing different drugs dissolved at different rates, and become invisible to the naked eye after different periods of time that correlated to the time at which f≈1 as measured by UV Spectroscopy. Thus, drug release rate of the polymers can be characterized by two global parameters: The delay period (i.e. the time required to reach the steady state release rate) and the steady state release rate.

The same polymer was utilized in each of the above matrices. Thus, the differences in the delay period and steady state release rates of the matrices were due to the drug component of the matrix. Differences in the release rate of a drug matrix may attributed to different diffusion and leaching rates of the drugs within the polymeric matrix, and/or to different polymer degradation rates. Polymer degradation rates vary among the matrices utilized in this experiment, as evidenced by different rates of disappearance of the pellets. Thus, the presence of the drug affects the polymer degradation rate To understand the effect of an incorporated drug on the polymer degradation, the following model of the degradation process was developed, based on the data of the present invention: The mobility (diffusion) of the drug in the polymeric matrix is likely to be negligible compared to the polymer degradation rate. Thus, drug release occurs chiefly via polymer degradation. The polymer PLGA degradation into lactic acid and glycolic acid occurs through a reaction with water:

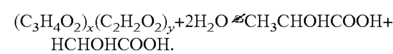

$$(C_3H_4O_2)_x(C_2H_2O_2)_y+2H_2O \rightleftharpoons CH_3CHOHCOOH+HCHOHCOOH.$$

Thus, the rate of degradation depends on the availability of water molecules. In systems where the diffusion of water into the pellet is suppressed, this indicates surface erosion. In systems where the diffusivity of water into the polymer is high, this leads to bulk erosion.

The degradation reaction is likely to be a $1^{st}$ order reaction between the polymer and water, and is thus proportional to the local concentration of both species. However, since the polymer comprises the majority of the pellet, its concemration is fixed everywhere. Thus, the degradation reaction is proportional to the local concentration of water (a function of the diffusivity) times a constant. Defining the diffusion coefficient of water into the polymer pellet as D, the diffusion/reaction equation for water is written as (1):

$$\frac{\partial c_w}{\partial t} = D\nabla^2 c_w - kc_w \tag{1}$$

where k the reaction rate, which includes the local polymer concentration, is constant. Appropriate boundary conditions are that the concentration of water at the particle edge is fixed by the solution value $c_w^0$, and that initially (at t=0) the concentration of water in the particle is zero.

Equation (1) indicates that in systems where D is close to 0, there is no diffusion into the polymeric particle, $c_w$ is zero within the pellet, and all reactions take place at the polymer/solution interface. In systems where the diffusion rate is large compared to the reaction rate, water will penetrate and degrade the entire particle volume through bulk erosion. The water concentration profile is solved by assuming that the pellet is a semi-infinite medium. This assumption is appropriate for the initial and steady-state stages of the degradation when the diffusion distance of the water is small compared to pellet dimensions.

Defining the distance from the polymer/solution interface as x, it was found that:

$$\frac{c_w}{c_w^0} = e^{-kt}\left(1 - erf\left[\frac{x}{\sqrt{Dt}}\right]\right) + k\int_0^t e^{-kt'}\left(1 - erf\left[\frac{x}{\sqrt{Dt'}}\right]\right)dt' \tag{2}$$

The amount of polymer that reacted, at any given location (x), with water and degraded was then obtained through integration over time:

$$dM_p(x, t) = k\int_0^t c_w(x, t')\,dt' \tag{3.a}$$

where $dM_p(x,t)$ is the change in polymer pellet mass at point x. Thus, the overall mass of degraded polymer is described by $$\Delta M_p = \int_{x=0}^{\infty} dM_p(x,t)dx = k\int_{x=0}^{\infty}\int_0^t c_w(x,t')dt'\,dx \tag{3.b}$$

and the amount of released drug $M_d$ (neglecting drug diffusion) is $$M_d(t) = \phi dM_p = \phi k\int_0^{\infty}\int_0^t c_w(x,t')dt'\,dx \tag{4}$$

where Φ is the weight fraction of the drug in the particle. Initially, when t is small, $M_d$ is described by $$M_d \approx \frac{2\phi c_w^0 D^{1/2} t^{3/2}}{3\pi^{1/2}} \sim t^{3/2} \tag{5.a}$$

while at later time points, the release rate is given by $$M_d \approx \frac{\phi c_w^0 D^{1/2} t}{2k^{1/2}} \sim t \tag{5.b}$$

It was thus determined that, initially, the amount of drug released increases with time to the power of (3/2), with a release rate (the slope) that is dependent only upon the water diffusion coefficient D. As time increases, the amount of released drug becomes linear with time. In this regime the system reaches "steady state" when the degradation late and the amount of drug released are constant with time. Accordingly, the release rate varies with the ratio between the diffusion and reaction constants.

Figures 11A, 11B:
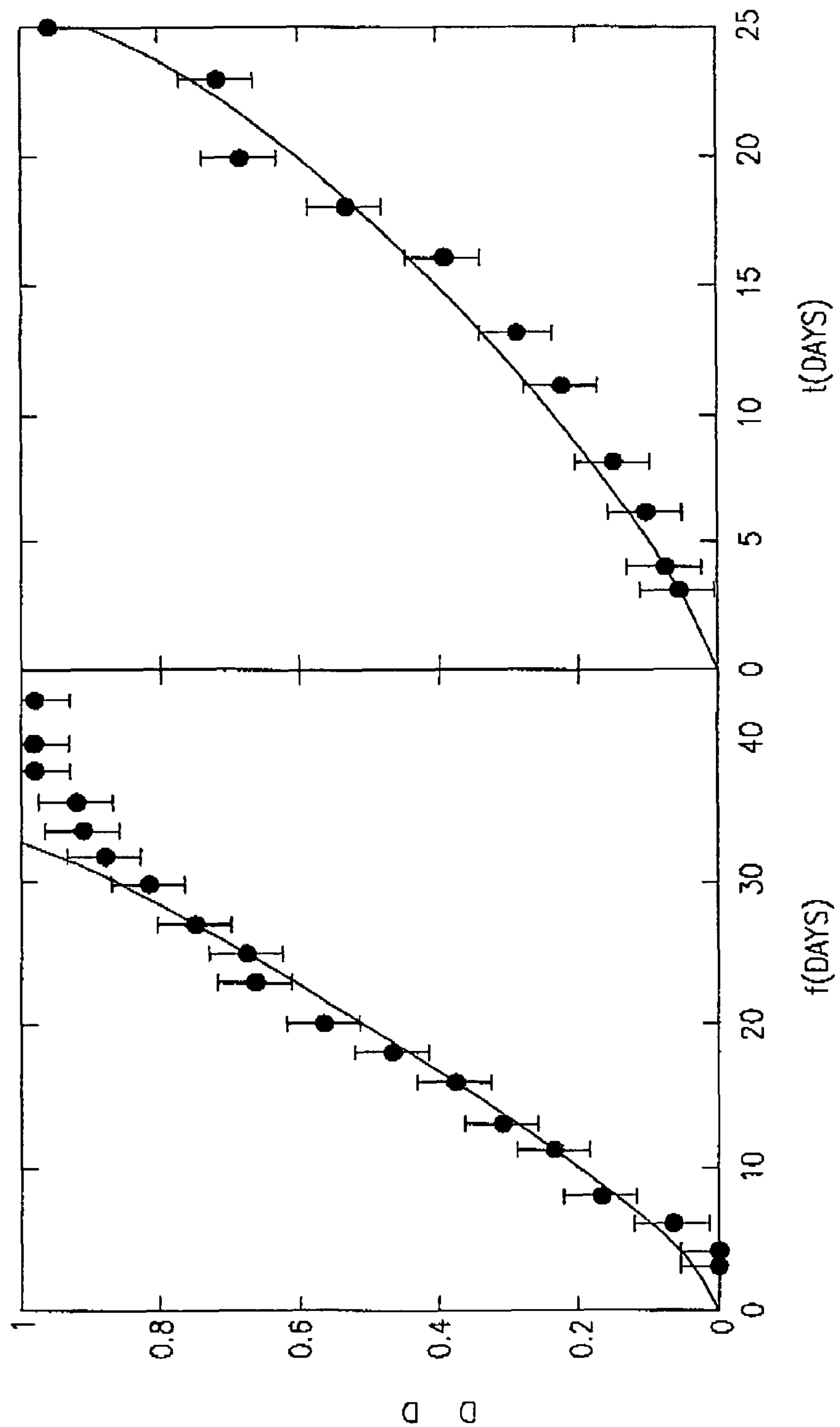
FIG. 11. Fit of the haloperidol (A) and ibuprofene (B) data to the model presented in equation 4, using the fit parameters D and k: For (A) k is approximately 0.1 (1/days) and D is 0.045. For (B) k is approximately 0.164 (1/days) and D is 0.051

The model described by Equation (4) fit well the drug release data shown in FIG. 10 for all six drugs tested, with values of D and k as listed in Table 1 (the curves for haloperidol and aspirin are depicted in FIG. 11). This is notable because the drugs tested are diverse; e.g. haloperidol and aspirin are very different. The deviations seen at late time points arose from the finite size of the pellets.

Thus, the release rate of drugs from bio-degradable matrices can be accounted for by a model containing only two fit parameters: D and k.

Example 11

Parameters D and K in the Release Equation can be Determined from the Solubility of the Drug and its Density of Hydroxyl Groups It was observed that the parameter k, the coefficient for the degradation reaction, varied over less than an order of magnitude for all drugs (0.05-0.33); by contrast, D, the diffusion coefficient, varied over 8 orders of magnitude (Table 1).

The diffusion constant of molecules in solid polymeric media is described by $D_0$ e sup[−δϵ], where $D_0$ is a proportionality coefficient, ϵ is an activation, or interaction energy and δ is a thermodynamic constant that depends, among other things, on the system temperature. In the present case, the polymeric matrix is the same, as is the temperature; thus, $D_0$ and δ are the same for all polymer/drug pellets. The activation energy ϵ, however, is sensitive to the specific interactions between the diffu ;ant and the matrix, and thus varies with drug type and loading (mass fraction). The drug solubility in water (assuming an ideal mixture) can also be described in terms of ϵ: S, the solubility, is equal to $S_0$e- sup[−δϵ], where $S_0$ is a proportionality coefficient and a is a thermodynamic constant. Combining the relationships for D and S leads to the following relationship:

$$D = \left(D_0 S_0^{-\delta/\sigma}\right) S^{\delta/\sigma} \tag{6}$$

wherein the term in parenthesis is, in the present case, a system constant.

Figure 12:
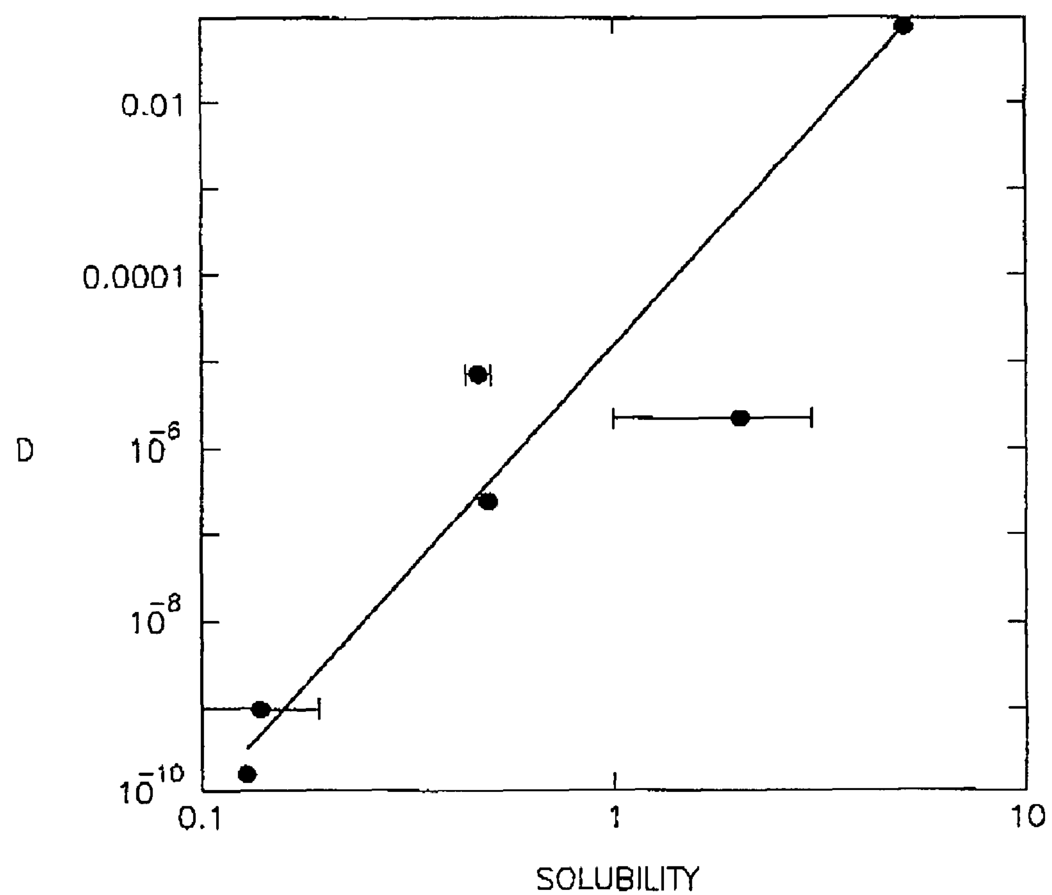
FIG. 12. Relationship between maximal solubility of drugs in water after 14 days (in mg/mL) and D, the diffusion coefficient of water into the polymer/drug complex, as calculated from fit of the data in FIG. 10 to equation 4. D is proportional to solubility to the power of 5.3.

As depicted in FIG. 12, the solubility data was fit to equation (6). The dependence of D on the solubility was described through a power law, with a coefficient of approximately 5.3.

In conclusion, the model described by Equation (4) can be used to predict the drug release rate during the steady state for PLGA implants containing 20% drug load. D is proportional to the solubility to the power of 5.3, and k is a number within the range of about 0.05-0.33.

Example 12

Determination of Drug Release from PLGA Polymer Implants and Resulting Serum Drug Concentration as a Function of Time and Implant Properties Since the focus of Examples 10-11 was to examine the effect of drug/polymer/water interactions on the degradation and release rate, the original model utilized an implant of infinitely large size. The present Example describes the time-dependent concentration of drug in vivo. To that end, the previous model was modified to account fox (1) finite implant size and (2) drug absorption and clearance (metabolic rate). The rate of drug release from an implant is proportional to the implant surface area (SA). Correcting for change in implant mass, the SA of the implant, A, can be described as equation 7, where R(t) is the implant radius as a function of time t, $R_0$ is the initial radius, D is the diffusion coefficient of water into the matrix, k the reaction rate and $C_w$ the concentration of water.

$$A = 4\pi R^2(t) = 4\pi R_0^2\left(1 - \frac{C_w\sqrt{D}}{2R_0\sqrt{k}}t\right)^2 \tag{7}$$

The rate of drug release per unit time can therefore be calculated as equation 8.

$$\left(\frac{dM_d}{dt}\right) = A(t)\frac{C_w\sqrt{D}\,erf\left[\sqrt{kt}\right]}{2\sqrt{k}} = 4\pi R_0^2\left(1 - \frac{C_w\sqrt{D}}{2R_0\sqrt{k}}t\right)^2 \frac{C_w\sqrt{D}\,erf\left[\sqrt{kt}\right]}{2\sqrt{k}} \tag{8}$$

where "erf(x)" refers to $2/\infty\sqrt{\pi}\int_0^x e^{t2}$ dt.

The metabolic rate of risperidone can be written as an exponential decay of drug in blood, with a characteristic decay rate τ that varies as a function of drug and metabolic rate, yielding a complex function for the effective drug concentration shown in equation 9. The function can be asymmetric, and its degree of asymmetry is set by the value of τ, the typical metabolizing time for the given drug. A high value of τ indicates slow metabolic rate, and thus the function is more symmetrical. A low value of τ indicates fast metabolism and the function becomes more asymmetric as the peak moves closer to t=0.

$$\left(\frac{dM_d}{dt}\right) = 4\pi R_0^2\left(1 - \frac{C_w\sqrt{D}}{2R_0\sqrt{k}}t\right)^2 \frac{C_w\sqrt{D}\,erf\left[\sqrt{kt}\right]}{2\sqrt{k}}(1 - e^{t/\tau}) \quad (9)$$

The concentration of drug as a function of time is a complex function. The error function can be approximated as erf(x)~1-$e^{-7x/4}$, yielding equation 10 for the drug concentration. $a_1$ is a constant equal to the total drug content of the implant, variable $a_2$ is a constant equal to the metabolic rate, variable $a_3$ reflects diffusion of drug from the implant and variable $a_4$ reflects polymer degradation and influences total release interval. Fitting rabbit haloperidol data, we extract the coefficient τ≈0.027, indicating a serum half-life for haloperidol in rabbit of about 130 minutes, consistent with published data (Wurzburger R J, Miller R L et al, J Pharmacol Exp Ther 217: 757-763). This equation fits prior in vivo rabbit data with a correlation coefficient ($R^2$) of 0.87.

$$\left(\frac{dM_d}{dt}\right) \sim a_1(1 - e^{-a_2 t})(1 + e^{a_3\sqrt{t}})(1 - a_4 t)^2 \quad (10)$$

Example 13

Determination of the Contribution of Polymer Composition and Inherent Viscosity on Drug Release from PLGA Polymer Implants Polymer composition and inherent viscosity are varied as described in Examples 1-7 to determine the additional contributions of these variables to drug release from PLGA polymer implants. Additional equations are produced, incorporating these variables

Example 14

Scaling-Up of Risperidone Implants to Human Subjects

Considerable interspecies differences exist in the metabolism of risperidone, with both rabbits and monkeys requiting approximately 15 to 30 fold higher doses than humans for equivalent plasma concentrations (Bacopoulos NG, Redmond D E, et al, J Pharmacol Exp Ther 212: 1-5; Jibiki I, Kubota I, et al, Jpn J Psychiatry Neurol 47: 627-629; Klintenberg R, Gunne L, Andren PE (2002) Mov Disoid 17: 360-365). Thus, the absolute doses used in the above animal studies approximate the amount of drug needed for a human, despite the difference in body mass. Since humans require approximately 1 mg/kg/month of risperidone (typically about 1.8 mg/day) when administered as a depot preparation, an implant system containing 600 mg would provide one year of treatment for a 50 kg patient. Thus, the implant design used in the animal studies necessitates about 1.5 grams of material with 40% drug load for one year of risperidone. At a density of 1.2 g per cc and diameter of 3.6 mm, this requires approximately 6.5 cm of implant rods.

Risperidone implants within the following parameters are administered to humans:

drug load between about 30%-60%, inclusive.

PLA:PGA molar ratio between about 50:50 and 100:0, inclusive.

Rod-shaped.

SA:V ratio between 1.5 and 2.

Figure 13A:
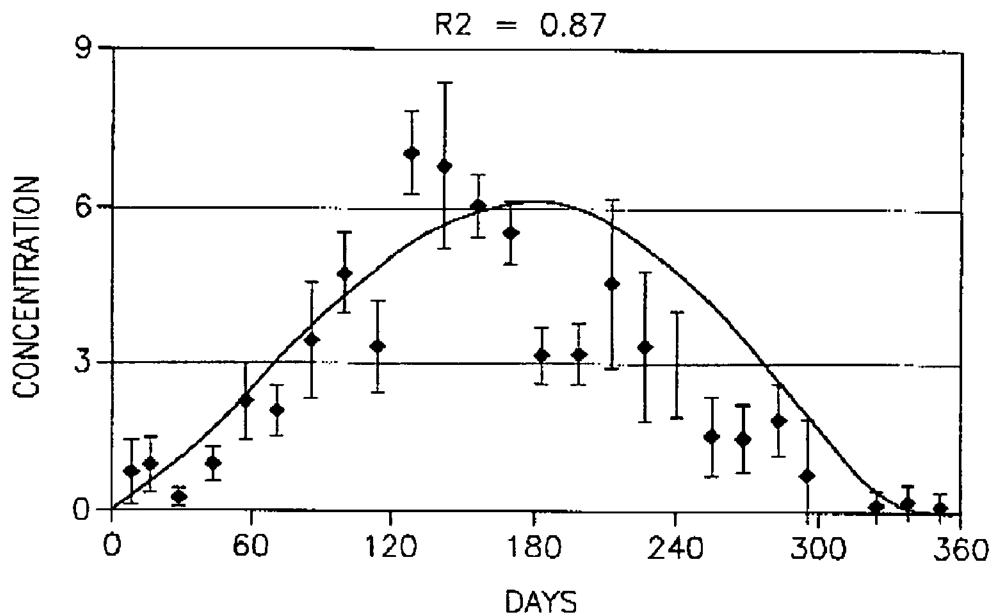
FIG. 13: Model for continuous delivery from biodegradable implants: A) Pattern of serum concentration that results from one or more single-polymer implants. Trendlines represent the drug release pattern. B) Superimposed profiles fox each of 4 implantations of the single-polymer implant system. Re-implantation for this polymer-drug combination is performed every 6 months. C) The total serum concentration that results from individual overlapping implantations (dashed lines) is shown with a sold line. Levels oscillate slightly, but remain within the target range for as long as implantations occur near the time of peak concentration for a given material. Arrows mark implantations in all panels.

For example, rod-shaped implants with length between about 3-5 mm, inclusive and diameter between 2 and 3.6 mm, inclusive, exhibit the target SA:V ratio. By administration of 1 or more implants, a substantially symmetrical concentration profile is achieved, as seen in Example 2, with peak levels reached at approximately 6 months and therapeutic risperidone levels achieved between 2 and 8 months post implantation (FIG. 13A).

Example 15

Figure 13B:
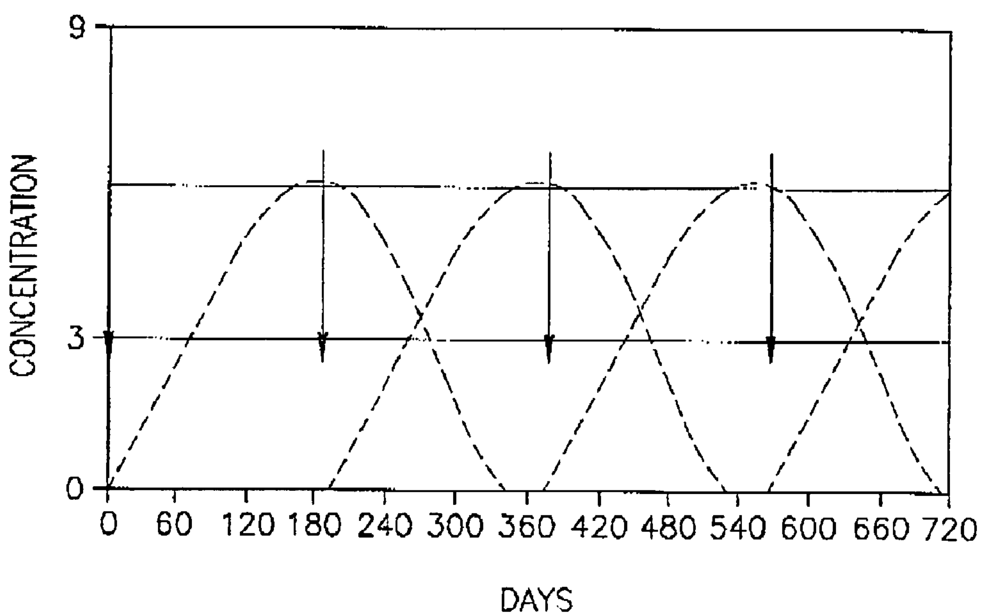
Figure 13C:
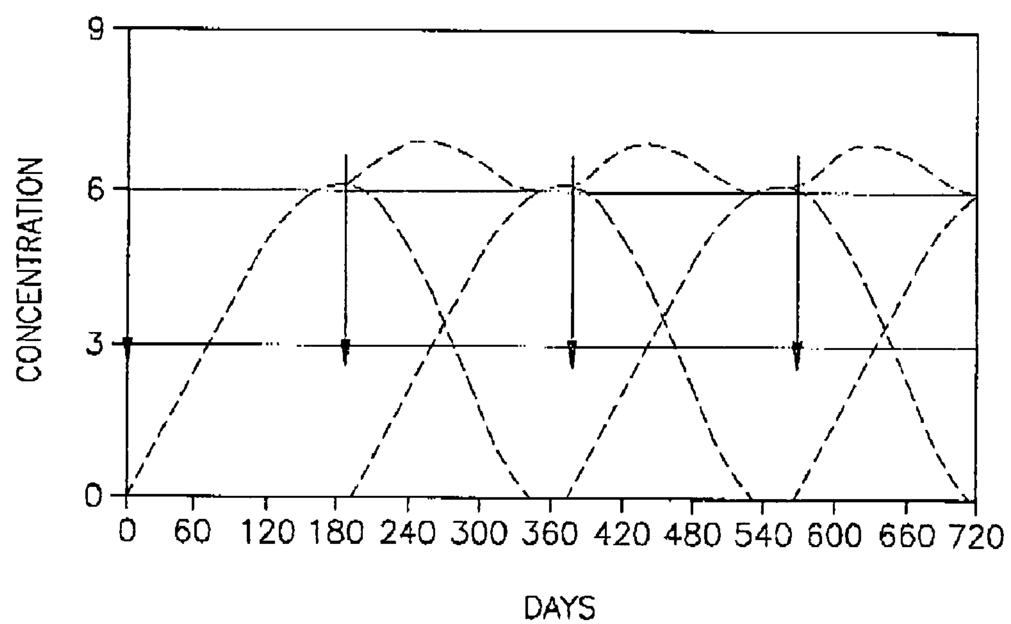

Cyclical Administration or Risperidone Implants Achieves Long-Term Therapeutic Risperidone Levels The symmetrical release profile described in Example 14 is used to provide long-term therapeutic drug levels by introducing a new set of implants approximately every 6 months (FIG. 13B). For example, two rods of 3.2 cm length with 100% PLA ale administered every 6 months. As depicted, each subsequent set of implants increases medication levels at the same rate that the contribution from the previous set is declining, such that the overall rate of release remains approximately constant (FIG. 13C).

Example 16

Improvement of Initial Drug Levels by Inclusion of Faster-Release Polymers in the Initial Implantation A limitation of a single-polymer system is a lag in reaching therapeutic levels following the initial implantation. Thus, additional implants that provide amore rapid time to peak concentration ale included in the initial implantation. One or more of the implants depicted in Table 3 is included. Release rates of the rapid-release implants in Table 3 arid resulting serum concentrations are derived from equations 8-10 by varying the parameters a1 and a4, which are related to drug content (total dose) and polymer degradation (PLGA ratio and inherent viscosity).

Table 3. Additional polymer implants utilized with initial implantation Implants contain between 40-60% risperidone load, inclusive, and exhibit a target delivery of 0.15 mg/day. Each rod has a 3.6 mm diameter with density of 1.2 grams per cubic centimeter (g/cc), yielding rods with approximately 125 mg/cm of implant.

| Polymer | Days to maximum concentration | Days to full release | mg implant mass 0%, 40%, 50%, 60% | total cm implant length 0%, 40%, 50%, 60% |
|---|---|---|---|---|
| 50:50 L | 20 | 40 | 60, 60, 48, 40 | 0.5, 0.5, 0.4, 0.3 |
| 50:50 H | 28 | 55 | 83, 83, 66, 55 | 0.6, 0.6, 0.5, 0.4 |
| 65:35 L | 45 | 90 | 135, 135, 108, 90 | 1.1, 1.1, 0.8, 0.7 |
| 65:35 H | 55 | 110 | 165, 165, 132, 110 | 1.1, 1.4, 1.1, 0.9 |
| 75:25 L | 60 | 120 | 180, 180, 144, 120 | 1.5, 1.5, 1.2, 1.0 |
| 75:25 H | 70 | 140 | 210, 210, 168, 140 | 1.7, 1.7, 1.3, 1.1 |
| 85:15 L | 75 | 150 | 225, 225, 180, 150 | 1.8, 1.8, 1.4, 1.2 |

-continued

| Polymer | Days to maximum concentration | Days to full release | mg implant mass 0%, 40%, 50%, 60% | total cm implant length 0%, 40%, 50%, 60% |
|---|---|---|---|---|
| 85:15 H | 90 | 180 | 270, 270, 216, 180 | 2.1, 2.1, 1.7, 1.4 |
| 100:0 L | 175 | 350 | 525, 525, 420, 350 | 4.2, 4.2, 3.4, 2.8 |
| 100:0 H | 190 | 380 | 570, 570, 456, 380 | 4.5, 4.5, 3.6, 3.0 |
| Positive Controls | | Days of exposure = 30, 60, 90, 120, 180, 360 | | |

Figure 14A:
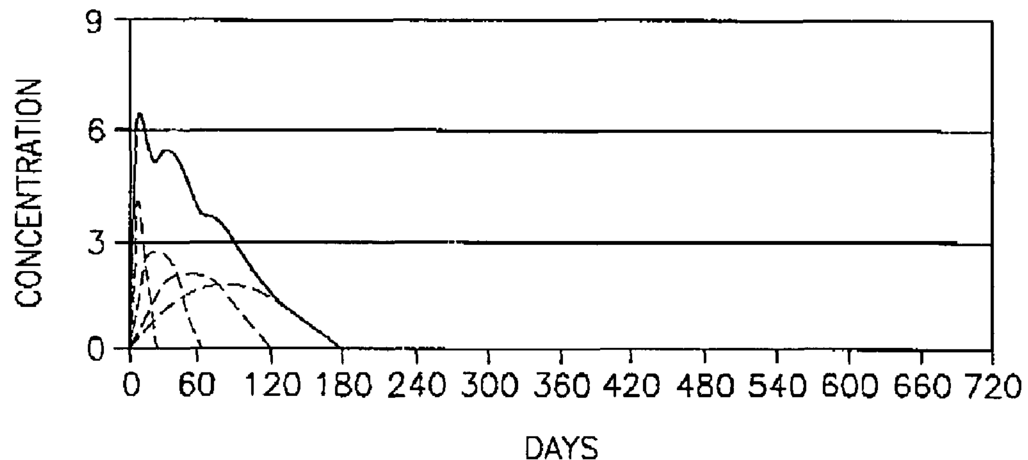
FIG. 14. Risperidone serum concentration resulting from a multiple-polymer risperidone implant system. A) Serum concentration resulting from a set of 4 rapid-release implants. B) Serum concentration resulting from a 5-polymer system, in which 4 rapidly degrading polymers ("starter set") are combined with 1 longer lasting polymer that is re-implanted every 6 months as a maintenance set Overall drug concentration is represented with the solid line, and release profiles from individual polymers ale represented by dashed lines. Target drug levels are attained in approximately 1 week, with small oscillations around the target concentration thereafter.
Figure 14B:
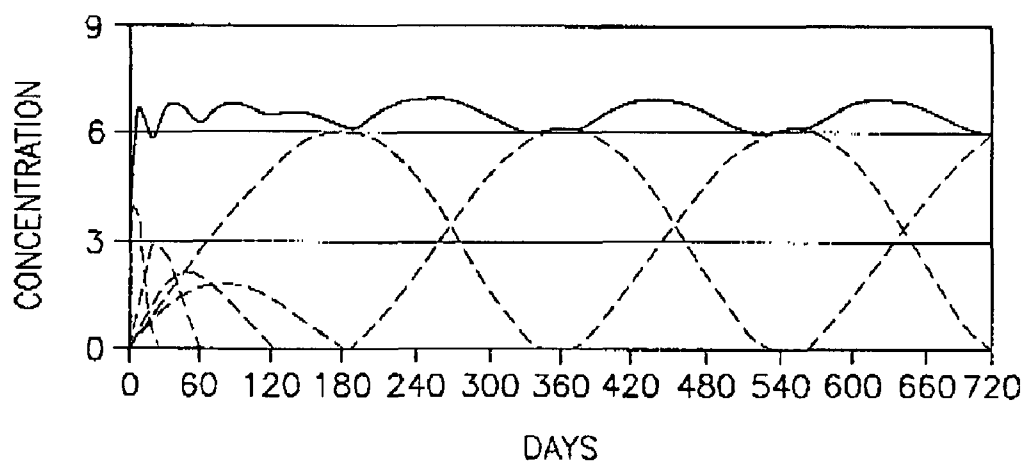

For example, FIG. 14A illustrates the drug release from foul rapid-release implants having half-lives of approximately 2, 4, 8 and 12 weeks and full release intervals of approximately 4, 8, 16 and 24 weeks, respectively. For example, a set of implants containing half of the first 6 months of medication includes 4 implants with an average length of 0.8 cm, composed of 50:50, 65:35, 75:25 and 85:15 PLGA respectively. This set is given in combination with the slower-release implants, which provides the other half of the medication. When this combination of implants is administered at the first implantation, therapeutic drug levels ale attained within a few days of implantation, and are sustained indefinitely via implantation of the slower-release implants at 6-month intervals thereafter (FIG. 14B).

What is claimed is:

1. A biodegradable implant comprising a therapeutic drug and a polymer, said polymer comprising polylactic acid (PLA) and polyglycolic acid (PGA) in a PLA:PGA molar ratio between 50:50 and 100:0, wherein said therapeutic drug is present in an amount of 10%-60% of the mass of said implant, and said polymer is present in an amount of 40%-90% of the mass of said implant, wherein said therapeutic drug in said implant is capable of exhibiting the time to maximum serum concentration ranging from about 20 days to about 190 days after implanting said implant in a subject, and wherein said therapeutic drug comprises risperidone, 9-OH-risperidone, or an active metabolite thereof.

2. The implant of claim 1, wherein said implant is removable.

3. The implant of claim 1, wherein said therapeutic drug further comprises haloperidol.

4. The implant of claim 1, wherein said implant has a surface area to volume ratio between 1 and 4 (millimeters $[mm])^2/mm^3$.

5. The implant of claim 1, wherein said implant has a length between 3-45 millimeters.

6. The implant of claim 1, wherein said implant has a diameter between 2-4 millimeters.

7. A method for releasing a therapeutic drug at a substantially linear rate for a period of at least 1 month into a body tissue of a subject, comprising administering to said subject the implant of claim 1, thereby releasing a therapeutic drug at a substantially linear rate for a period of at least 1 month into a body tissue of a subject.

8. A method for treating schizophrenia in a human, comprising administering the implant of claim 1 to said human, thereby treating schizophrenia in said human.

9. A method for treating bipolar disorder, agitation, impulse control, dementia, depression or delirium in a human, comprising administering the implant of claim 1 to said human, thereby treating bipolar disorder, agitation, impulse control, dementia, depression or delirium in said human.

10. A biodegradable implant comprising a therapeutic drug and a polymer, said polymer comprising polylactic acid (PLA) and polyglycolic acid (PGA) in a PLA:PGA molar ratio between 75:25 and 100:0, wherein said therapeutic drug is present in an amount of 20-50% of the mass of said implant, and said polymer is present in an amount of 50-80% of the mass of said implant, wherein said therapeutic drug in said implant is capable of exhibiting the time to maximum serum concentration ranging from about 20 days to about 190 days after implanting said implant in a subject, and wherein said therapeutic drug comprises risperidone, 9-OH-risperidone, or an active metabolite thereof.

* * * * *